United States Patent
Klimatcheva et al.

(10) Patent No.: US 11,981,730 B2
(45) Date of Patent: May 14, 2024

(54) ANTI-CXCL13 ANTIBODIES AND METHODS OF USING THE SAME

(71) Applicant: Vaccinex, Inc., Rochester, NY (US)

(72) Inventors: Ekaterina Klimatcheva, Webster, NY (US); Mark Paris, Mendon, NY (US); Ernest S. Smith, W. Henrietta, NY (US)

(73) Assignee: Vaccinex, Inc., Rochester, NY (US)

( * ) Notice: Subject to any disclaimer, the term of this patent is extended or adjusted under 35 U.S.C. 154(b) by 445 days.

(21) Appl. No.: 17/030,627

(22) Filed: Sep. 24, 2020

(65) Prior Publication Data

US 2021/0087263 A1   Mar. 25, 2021

Related U.S. Application Data

(62) Division of application No. 15/953,139, filed on Apr. 13, 2018, now Pat. No. 10,829,550, which is a division of application No. 13/820,278, filed as application No. PCT/US2011/050177 on Sep. 1, 2011, now Pat. No. 9,963,504.

(60) Provisional application No. 61/481,645, filed on May 2, 2011, provisional application No. 61/379,672, filed on Sep. 2, 2010.

(51) Int. Cl.
*C07K 16/24* (2006.01)
*A61K 39/00* (2006.01)

(52) U.S. Cl.
CPC ........ *C07K 16/24* (2013.01); *A61K 2039/505* (2013.01); *C07K 2317/24* (2013.01); *C07K 2317/33* (2013.01); *C07K 2317/34* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,474,893 A | 10/1984 | Reading |
| 4,683,195 A | 7/1987 | Mullis et al. |
| 4,714,681 A | 12/1987 | Reading |
| 4,741,900 A | 5/1988 | Alvarez et al. |
| 4,873,192 A | 10/1989 | Kunkel |
| 4,925,648 A | 5/1990 | Hansen et al. |
| 5,116,964 A | 5/1992 | Capon et al. |
| 5,122,464 A | 6/1992 | Wilson et al. |
| 5,225,538 A | 7/1993 | Capon et al. |
| 5,225,539 A | 7/1993 | Winter |
| 5,314,995 A | 5/1994 | Fell, Jr. et al. |
| 5,573,920 A | 11/1996 | Randle |
| 5,585,089 A | 12/1996 | Queen et al. |
| 5,601,819 A | 2/1997 | Wong et al. |
| 5,693,761 A | 12/1997 | Queen et al. |
| 5,693,762 A | 12/1997 | Queen et al. |
| 5,731,168 A | 3/1998 | Carter et al. |
| 5,807,706 A | 9/1998 | Carter et al. |
| 5,821,333 A | 10/1998 | Carter et al. |
| 5,859,205 A | 1/1999 | Adair et al. |
| 5,892,019 A | 4/1999 | Schlom et al. |
| 5,939,598 A | 8/1999 | Kucherlapati et al. |
| 6,180,370 B1 | 1/2001 | Queen et al. |
| 6,737,056 B1 | 5/2004 | Presta |
| 2002/0123057 A1 | 9/2002 | Zauderer et al. |
| 2002/0155537 A1 | 10/2002 | Carter et al. |
| 2003/0020734 A1 | 1/2003 | Yin et al. |
| 2004/0132101 A1 | 7/2004 | Lazar et al. |

FOREIGN PATENT DOCUMENTS

| | | |
|---|---|---|
| EP | 0075444 A2 | 3/1983 |
| EP | 396387 A2 | 11/1990 |
| WO | 1986005807 A1 | 10/1986 |
| WO | 1989001036 A1 | 2/1989 |
| WO | 1989012624 A2 | 12/1989 |
| WO | 1991000360 A1 | 1/1991 |
| WO | 1991014438 A1 | 10/1991 |
| WO | 1992005793 A1 | 4/1992 |
| WO | 1992008495 A1 | 5/1992 |
| WO | 1992008802 A1 | 5/1992 |
| WO | 1993017715 A1 | 9/1993 |
| WO | 2000044788 A1 | 8/2000 |
| WO | 2001027160 A1 | 4/2001 |
| WO | 2002096948 A2 | 12/2002 |

OTHER PUBLICATIONS

Cantrell et al. Gynecologic Oncology 2015 137:581-588.*
Szybalska and Szybalski, "Genetics of Human Cell Lines, IV. DNA-Mediated Heritable Transformation of a Biochemical Trait," PNAS Dec. 1, 1962 48 (12) 2026-2034.
Voller et al., "Enzyme immunoassays with special reference to ELISA techniques." J. Clin. Pathol. 31:507-520 (1978).
Verhoeyen et al., "Reshaping human antibodies: grafting an antilysozyme activity" Science 239:1534-1536 (1988).
Traunecker, A., "Highly efficient neutralization of HIV with recombinant CD4-immunoglobulin molecules." Nature 339, 68-70 (1989).
Zettmeissl et al., "A homing receptor-IgG chimera as a probe for adhesive ligands of lymph node high endothelial venules." DNA Cell Biol. USA 9:347-353 (1990).
Wu, G.Y., Wu, C.H. Delivery systems for gene therapy. Biotherapy 3, 87-95 (1991).
Byrn, R., Mordenti, J., Lucas, C. et al. Biological properties of a CD4 immunoadhesin. Nature 344, 667-670 (1990).
Capon, D., Chamow, S., Mordenti, J. et al. Designing CD4 immunoadhesins for AIDS therapy. Nature 337, 525-531 (1989).
Chapman, "PEGylated antigodies and antibody fragments for improved therapy: a review," Adv. in Drug Deliv. Rev. 54:531 (2002).
Cyrus Chothia, Arthur M. Lesk, "Canonical structures for the hypervariable regions of immunoglobulins" Journal of Molecular Biology, vol. 196, Issue 4, 1987, pp. 901-917.

(Continued)

*Primary Examiner* — Sharon X Wen
(74) *Attorney, Agent, or Firm* — KDW Firm PLLC

(57) ABSTRACT

Compositions and methods are provided for treating diseases associated with CXCL13 expression, including certain autoimmune diseases, inflammatory diseases, and cancers. In particular, anti-CXCL13 monoclonal antibodies have been developed to neutralize CXCL13.

12 Claims, 33 Drawing Sheets

Figure 2:
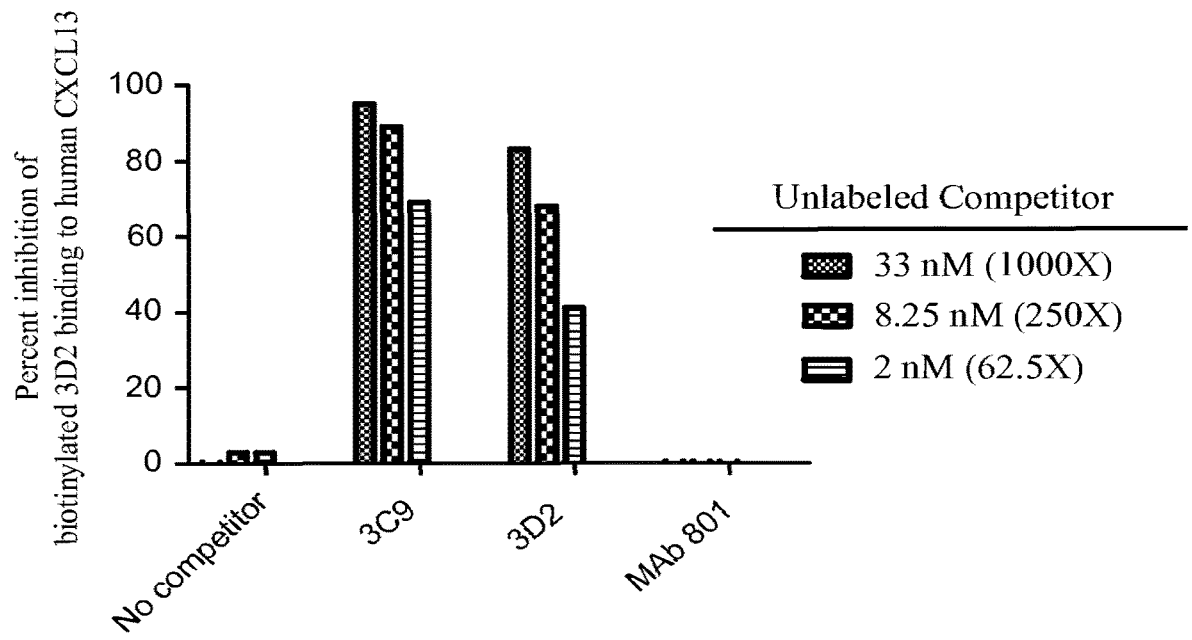

Specification includes a Sequence Listing.

(56) References Cited

OTHER PUBLICATIONS

Colbère-Garapin, F et al. "A new dominant hybrid selective marker for higher eukaryotic cells." Journal of molecular biology vol. 150,1 (1981): 1-14.
Cockett, M I et al. "High level expression of tissue inhibitor of metalloproteinases in Chinese hamster ovary cells using glutamine synthetase gene amplification." Bio/technology (Nature Publishing Company) vol. 8,7 (1990): 662-7.
Crouse et al., "Expression and amplification of engineered mouse dihydrofolate reductase minigenes" Mol. Cell. Biol. 3:257 (1983).
Dayhoff et al. (1978) in Atlas of Protein Sequence and Structure (Natl. Biomed. Res. Found., Washington, D.C.), pp. 345-352.
G Van Heeke, S M Schuster, "Expression of Human Asparagine Synthetase in *Escherichia coli*", Journal of Biological Chemistry, vol. 264, Issue 10, 1989, pp. 5503-5509.
Foecking, M K, and H Hofstetter. "Powerful and versatile enhancer-promoter unit for mammalian expression vectors." Gene vol. 45, 1 (1986): 101-5.
Gascoigne et al., "Secretion of a chimeric T-cell receptor-immunoglobulin protein" Proc. Natl. Acad. Sci. USA 84:2936-2940 (1987).
Gentz et al., "Bioassay for trans-activation using purified human immunodeficiency virus tat-encoded protein: trans-activation requires mRNA synthesis" Proc. Natl. Acad. Sci. USA 86:821-824 (1989).
Ian A. Wilson, et al., "The structure of an antigenic determinant in a protein", Cell, vol. 37, Issue 3, 1984, pp. 767-778.
Hamers-Casterman, C., Atarhouch, T., Muyldermans, S. et al. Naturally occurring antibodies devoid of light chains. Nature 363, 446-448 (1993).
Wigler et al., "Transformation of mammalian cells with an amplifiable dominant-acting gene" PNAS Jun. 1, 1980 77 (6) 3567-3570.
Inouye, S, and M Inouye. "Up-promoter mutations in the Ipp gene of *Escherichia coli*." Nucleic acids research vol. 13,9 (1985): 3101-10.
Jalkanen et al., "Cell surface proteoglycan of mouse mammary epithelial cells is shed by cleavage of its matrix-binding ectodomain from its membrane-associated domain." J. Cell Biol. 105:3087-3096 (1987).
Jalkanen, et al., "Heparan sulfate proteoglycans from mouse mammary epithelial cells: localization on the cell surface with a monoclonal antibody." J. Cell. Biol. 101:976-985 (1985).
Michael Wigler, "Transfer of purified herpes virus thymidine kinase gene to cultured mouse cells", Cell, vol. 11, Issue 1, 1977, pp. 223-232.
Jones, P., Dear, P., Foote, J. et al. Replacing the complementarity-determining regions in a human antibody with those from a mouse. Nature 321, 522-525 (1986).
Jones, E W. "Proteinase mutants of *Saccharomyces cerevisiae*." Genetics vol. 85,1 (1977): 23-33.
Alan J. Kingsman et al., "Replication in *Saccharomyces cerevisiae* of plasmid pBR313 carrying DNA from the yeast trpl region" Gene, vol. 7, Issue 2, 1979, pp. 141-152.
Kostelny et al., "Formation of a bispecific antibody by the use of leucine zippers." J. Immunol. 148: 1547-1553 (1992).
Thomas A. Kunkel, et al., "Rapid and efficient site-specific mutagenesis without phenotypic selection", Methods in Enzymology, Academic Press, vol. 154, 1987, pp. 367-382.
Kunkel, "Rapid and efficient site-specific mutagenesis without phenotypic selection" Proc. Natl. Acad. Sci. USA 82:488-492 (1985).
Tutt et al., "Trispecific F(ab')3 derivatives that use cooperative signaling via the TCR/CD3 complex and CD2 to activate and redirect resting cytotoxic T cells." J. Immunol. 147:60-69 (1991).

Steven R. Leong, et al., "Adapting Pharmacokinetic Properties of a Humanized Anti-Interleukin-8 Antibody for Therapeutic Applications Using Site-Spec" Cytokine, vol. 16, Issue 3, 2001, pp. 106-119.
Tschumper et al., "Sequence of a yeast DNA fragment containing a chromosomal replicator and the TRP1 gene" Gene, vol. 10. issue 2, Jul. 1980, pp. 157-166.
Linsley et al., "Binding of the B cell activation antigen B7 to CD28 costimulates T cell proliferation and interleukin 2 mRNA accumulation." J. Exp. Med. 173:721-730 (1991).
Linsley, P S et al. "CTLA-4 is a second receptor for the B cell activation antigen B7." The Journal of experimental medicine vol. 174,3 (1991): 561-9.
Israel Lowy, et al., "Isolation of transforming DNA: Cloning the hamster aprt gene", Cell, vol. 22, Issue 3, 1980, pp. 817-823.
Magliozzi, Roberta et al. "Meningeal B-cell follicles in secondary progressive multiple sclerosis associate with early onset of disease and severe cortical pathology." Brain : a journal of neurology vol. 130, Pt 4 (2007): 1089-104.
Morgan, R A, and W F Anderson. "Human gene therapy." Annual review of biochemistry vol. 62 (1993): 191-217. doi:10.1146/annurev.bi.62.070193.001203.
Mulligan, R C, and P Berg. "Selection for animal cells that express the *Escherichia coli* gene coding for xanthine-guanine phosphoribosyltransferase." Proceedings of the National Academy of Sciences of the United States of America vol. 78,4 (1981): 2072-6. doi:10.1073/pnas.78.4.2072.
Mulligan, R C. "The basic science of gene therapy." Science (New York, N.Y.) vol. 260,5110 (1993): 926-32. doi:10.1126/science.8493530.
OHare et al., "Transformation of mouse fibroblasts to methotrexate resistance by a recombinant plasmid expressing a prokaryotic dihydrofolate reductase" Proc. Natl. Acad. Sci. USA 78:1527 (1981).
Peppel et al., "A tumor necrosis factor (TNF) receptor-IgG heavy chain chimeric protein as a bivalent antagonist of TNF activity." J. Exp. Med. 174:1483-1489 (1991).
Watson, S., Fennie, C. & Lasky, L. Neutrophil influx into an inflammatory site inhibited by a soluble homing receptor-IgG chimaera. Nature 349, 164-167 (1991).
Rattan, S I et al. "Protein synthesis, posttranslational modifications, and aging." Annals of the New York Academy of Sciences vol. 663 (1992): 48-62. doi:10.1111/j.1749-6632.1992.tb38648.x.
Riechmann, L., Clark, M., Waldmann, H. et al. Reshaping human antibodies for therapy. Nature 332, 323-327 (1988). https://doi.org/10.1038/332323a0.
Watson et al., "A homing receptor-IgG chimera as a probe for adhesive ligands of lymph node high endothelial venules." J. Cell. Biol. 110:2221-2229 (1990).
Voller, A., "The Enzyme Linked Immunosorbent Assay (ELISA)" Microbiological Associates Quarterly Publication, Walkersville, Md. Diagnostic Horizons 2:1-7 (1978).
Riechmann, L., Clark, M., Waldmann, H. et al. Reshaping human antibodies for therapy. Nature 332, 323-327 (1988).
Roux et al., "Comparisons of the Ability of Human IgG3 Hinge Mutants, IgM, IgE, and IgA2, to Form Small Immune Complexes: A Role for Flexibility and Geometry" J. Immunol. 161:4083 (1998).
Ruther et al., "Easy identification of cDNA clones." EMBO J. 2:1791 (1983).
Robert F. Santerre, "Expression of prokaryotic genes for hygromycin B and G418 resistance as dominant-selection markers in mouse L cells", Gene, vol. 30, Issues 1-3, 1984, pp. 147-156.
Sam Seifter, Sasha Englard, "Analysis for protein modifications and nonprotein cofactors", Editor(s): Murray P. Deutscher, Methods in Enzymology, Academic Press, vol. 182, 1990, pp. 626-646.
Ivan Stamenkovic, et al., "The B lymphocyte adhesion molecule CD22 interacts with leukocyte common antigen CD45RO on T cells and α2-6 sialyltransferase, CD75", on B cells, Cell, vol. 66, Issue 6, 1991, pp. 1133-1144.

\* cited by examiner

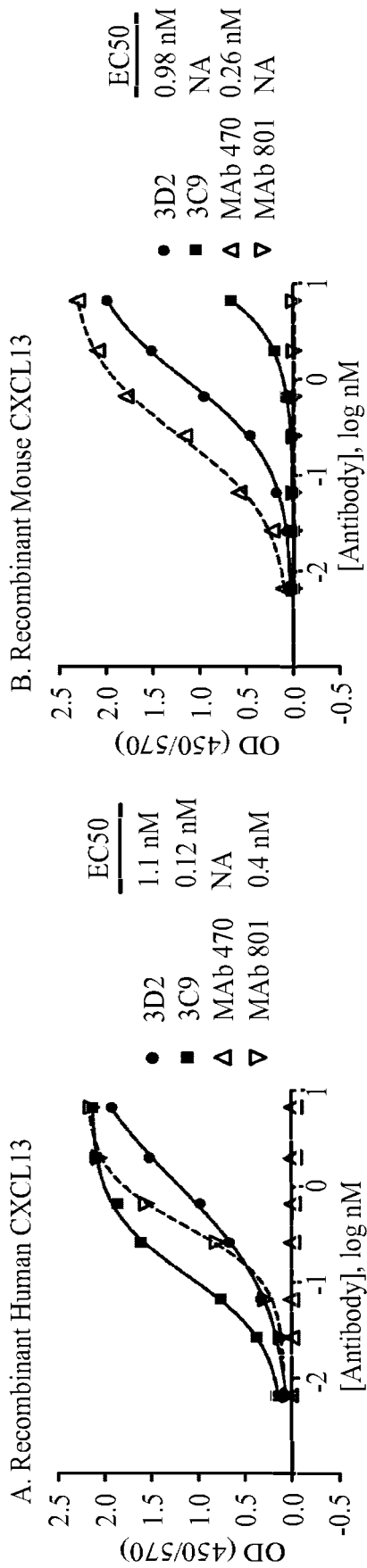
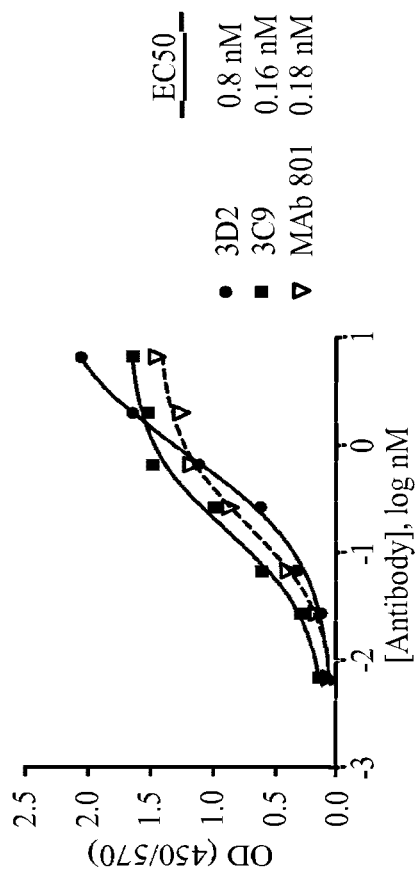
FIG. 1A
FIG. 1B
FIG. 1C

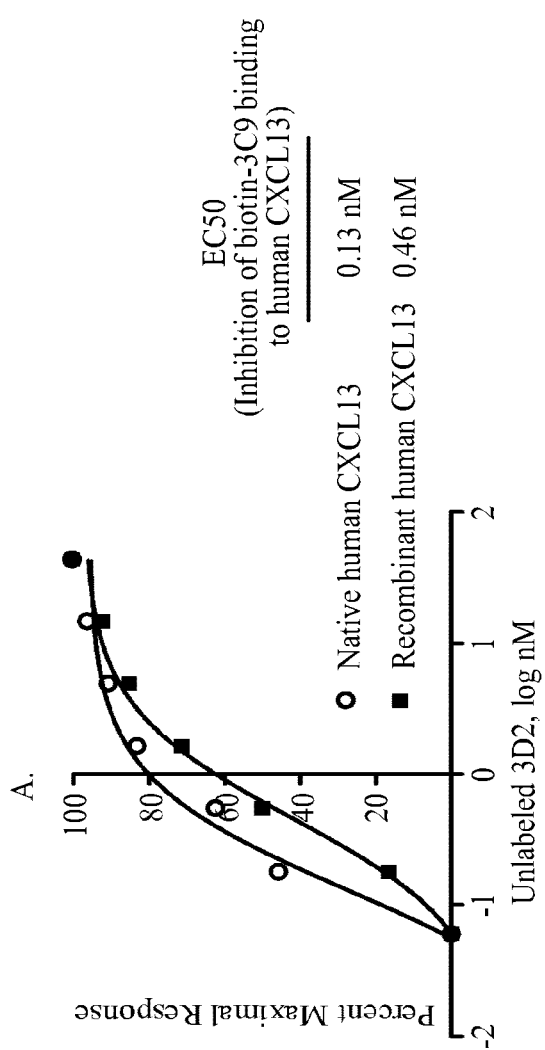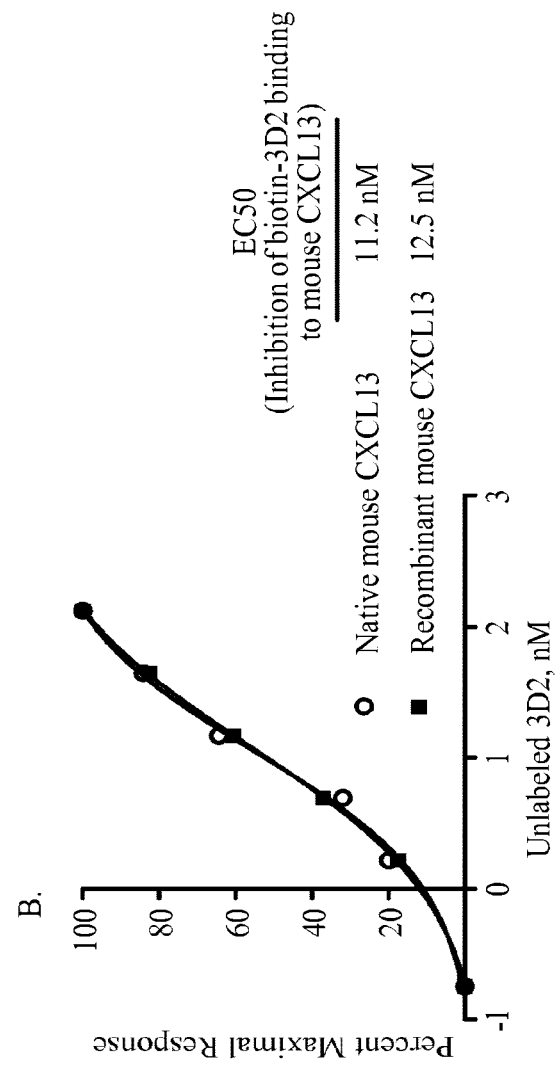
FIG. 3A
FIG. 3B

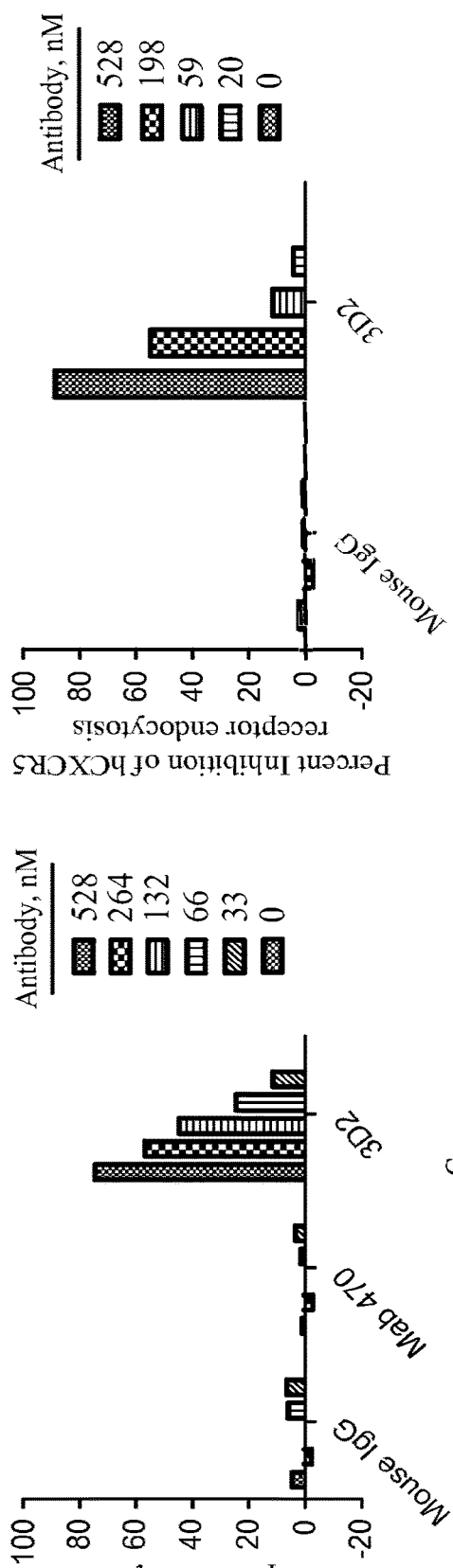
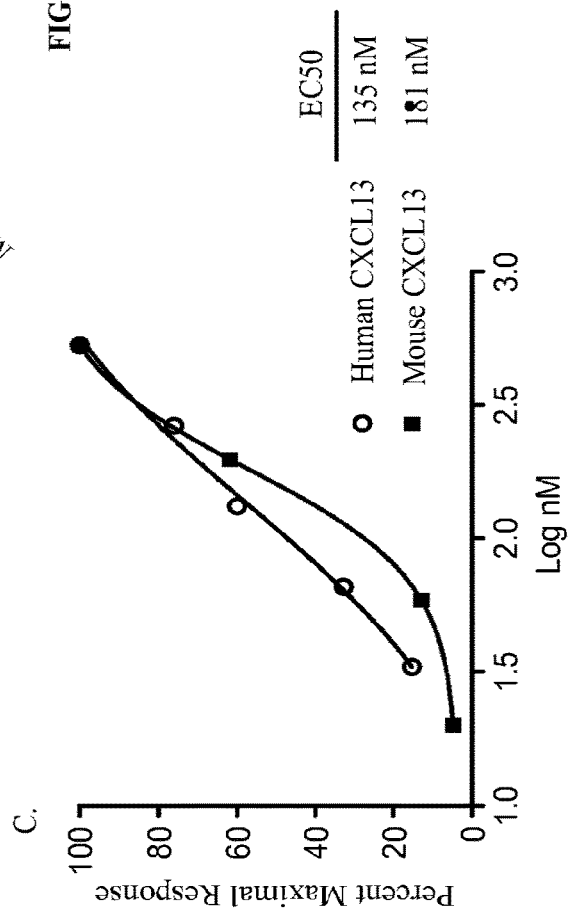
FIG. 6A
FIG. 6B
FIG. 6C

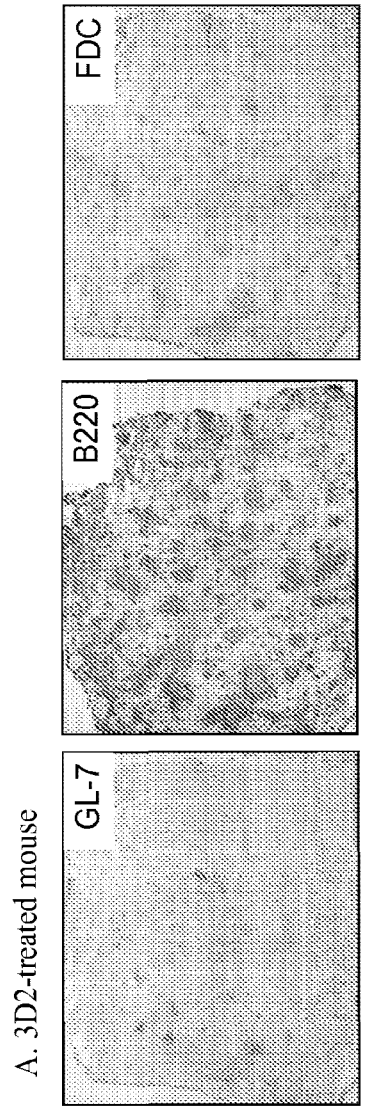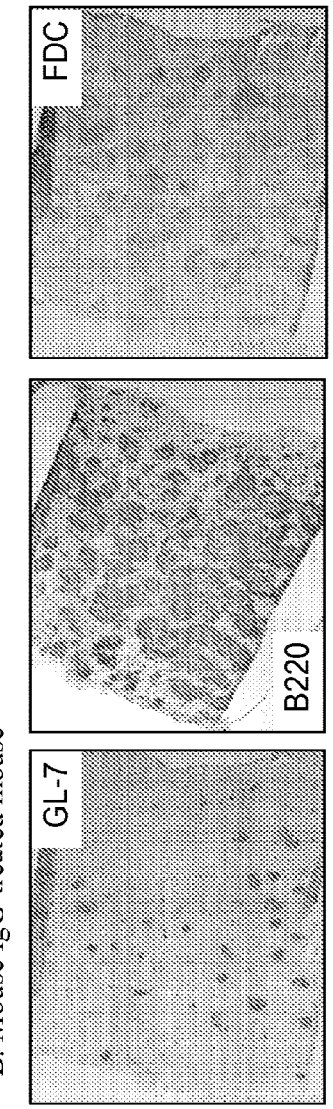
FIG. 11A
FIG. 11B
A. 3D2-treated mouse
B. Mouse IgG-treated mouse

H1609 DNA sequence:
GAGGTGCAGCTTCAGGAGTCTGGCCCTGGGATATTGCAGCCCTCCCAGACCCTCAATC
TGACTTGTTCTTTCTCTGGATTTCACTGAGCACTTTGGTATGGGTGTAGGCTGGATT
CGTCAGCCTTCAGGGAAGGGTCTGGAGTGGCTGGCACACATTTGGTGGGATGATGAT
AGGAGGTATAAACCCAGCCTGAAGAGTCGGCTCACAATCTCCAAGGAAACCTCCAAA
AACCAGGTGTTCCTCAAGATCGCCAATGTGGACACTGCAGATACTGCCACATACTACT
GTACTCGAATAGGCGGGTATTATGGTAGAGAGACTGGTTTGCTTACTGGGGCAAG
GGACCACGGTCACCGTCTCCTCA (SEQ ID NO: 2)

H1609 Amino Acid sequence:
EVQLQESGPGIL QPSQTLNLTCSFSGFSLSTFGMGVGWIRQPSGKGLEWLAHIWWDDDRR
YNPALKSRLTISKETSKNQVFLKIANVDTADTATYYCTRIAGYYGSRDWFAYWGQGTTV
TVSS (SEQ ID NO:3)

L0293: DNA sequence
GACATTGTGCTGACCCAGTCTCCAGCTTCTCTTTGGCTGTGTCTCTAGGGCAGAGGGCCA
CCATCTCCTGCAGAGCCAGCAGTGAAAGTGTTGATAATTCTGGCATTAGTTTTATGCACTG
GTACCAGCAGAAACCAGGACAGCCACCCAAACTCCTCATCTTTCGTGCATCCGACCTA
GAATCTGGGATCCCTGCCAGGTTCAGTGGCAGTGGGTCTAGGACAGATTCACCCTCA
CCGTTAATCCTGTGGAGACTGATGATGTGCAACCTATTTCTGTCAGCAAAGTAATAA
GGATCCGTGGACGTTCGGTGGAGGCACCAAGCTCGAGATCAAA (SEQ ID NO: 7)

L0293 Amino Acid sequence :
DIVLTQSPASLAVSLGQRATISCRASESVDNSGISFMHWYQQKPGQPPKLLIFRASDLESGI
PARFSGSGSRTDFTLTVNPVETDDVATYFCQQSNKDPWT FGGGTKLEIK (SEQ ID NO: 8)

H2177 DNA sequence:
CAGGTGCAGCTGCAGGAGAGCGGCCCAGGCCTGGTGAAGCCTAGCGAGACCCTGAGC
CTCACCTGCACCGTCAGCGGCTTTAGCCTGAGCACCTTTGGCATGGGCGTGGGCTGGA
TTAGACAGCCTCCAGGCAAGGGCCTGGAGTGGATTGCACACATTTGGTGGGATGATG
ATAGGAGATATAACCCAGCCCTGAAGAGCAGAGTGACCATCAGCAAGGACACCAGC
AAGAACCAGTTCAGCCTGAAGCTGAGCAGCGTGACCGCTGCCGACACCGCCGTGTAT
TACTGTGCCAGAATCGCCGGCTATTATGGCAGCAGAGACTGGTTTGCCTACTGGGGCC
AAGGCACCACGGTCAC CGTCTCCTCA (SEQ ID NO: 12)

H2177 Amino Acid sequence:
QVQLQESGPGLVKPSETLSLTCTVSGFSLS<u>TFGMGVG</u>WIRQPPGKGLEWIA<u>HIWWDDDRR
YNPALKSR</u>VTISKDTSKNQFSLKLSSVTAADTAVYYCAR<u>IAGYYGSRDWFAY</u>WGQGTTV
TVSS (SEQ ID NO: 13)

L5055: DNA sequence
GACATCCAGATGACCCAGTCTCCATCCTCCCTGTCTGCATCTGTGGGAGACAGAGTCA
CCATCACTTGCAGAGCCAGCGAAAGTGTTGATAATTCTGGCATTAGTTTTATGCACTG
GTATCAGCAGAAACCAGGGAAAGCCCCTAAGCTCCTGATCTTTAGAGCATCCGACCT
GGAATCTGGGGTCCCATCAGGGTTCAGTGGCAGTGGATCTAGGACAGATTTCACTCTC
ACCATCAGCAGTCTGCAACCTGAAGATTTTGCAACTTACTACTGTCAGCAAAGTAATA
AGGATCCCTGGACCTTCGGCCAAGGGACCAAGCTCGAGATCAAA (SEQ ID NO: 18)

L5055 Amino Acid sequence:
DIQMTQSPSSLSASVGDRVTITC<u>RASESVDNSGISFMH</u>WYQQKPGKAPKLLIF<u>RASDLESG</u>
VPSGFSGSGSRTDFTLTISSLQPEDFATYYC<u>QQSNKDPWT</u>FGQGTKLEIK(SEQ ID NO: 17)

L5140: DNA sequence
GACATCCAGATGACCCAGTCTCCATCCTCCCTGTCTGCATCTGTGGGAGACAGAGTCA
CCATCACTTGCAGAGCCAGCGAAAGTGTTGATAATATGGGCATTAGTTTTATGCACTG
GTATCAGCAGAAACCAGGGAAAGCCCCTAAGCTCCTGATCTTTAGAGCATCCGACCT
GGAATCTGGGGTCCCATCAAGGTTCAGTGGCAGTGGATCTGGGACAGATTTCACTCTC
ACCATCAGCAGTCTGCAACCTGAAGATTTTGCAACTTACTACTGTCAGCAAAGTAATA
AGGATCCCTGGACCTTCGGCCAAGGGACCAAGCTCGAGATCAAA (SEQ ID NO: 14)

L5140 Amino Acid sequence:
DIQMTQSPSSLSASVGDRVTITC<u>RASESVDNMGISFMH</u>WYQQKPGKAPKLLIF<u>RASDLESG</u>
VPSRFSGSGSGTDFTLTISSLQPEDFATYYC<u>QQSNKDPWT</u>FGQGTKLEIK(SEQ ID NO: 15)

FIG. 15

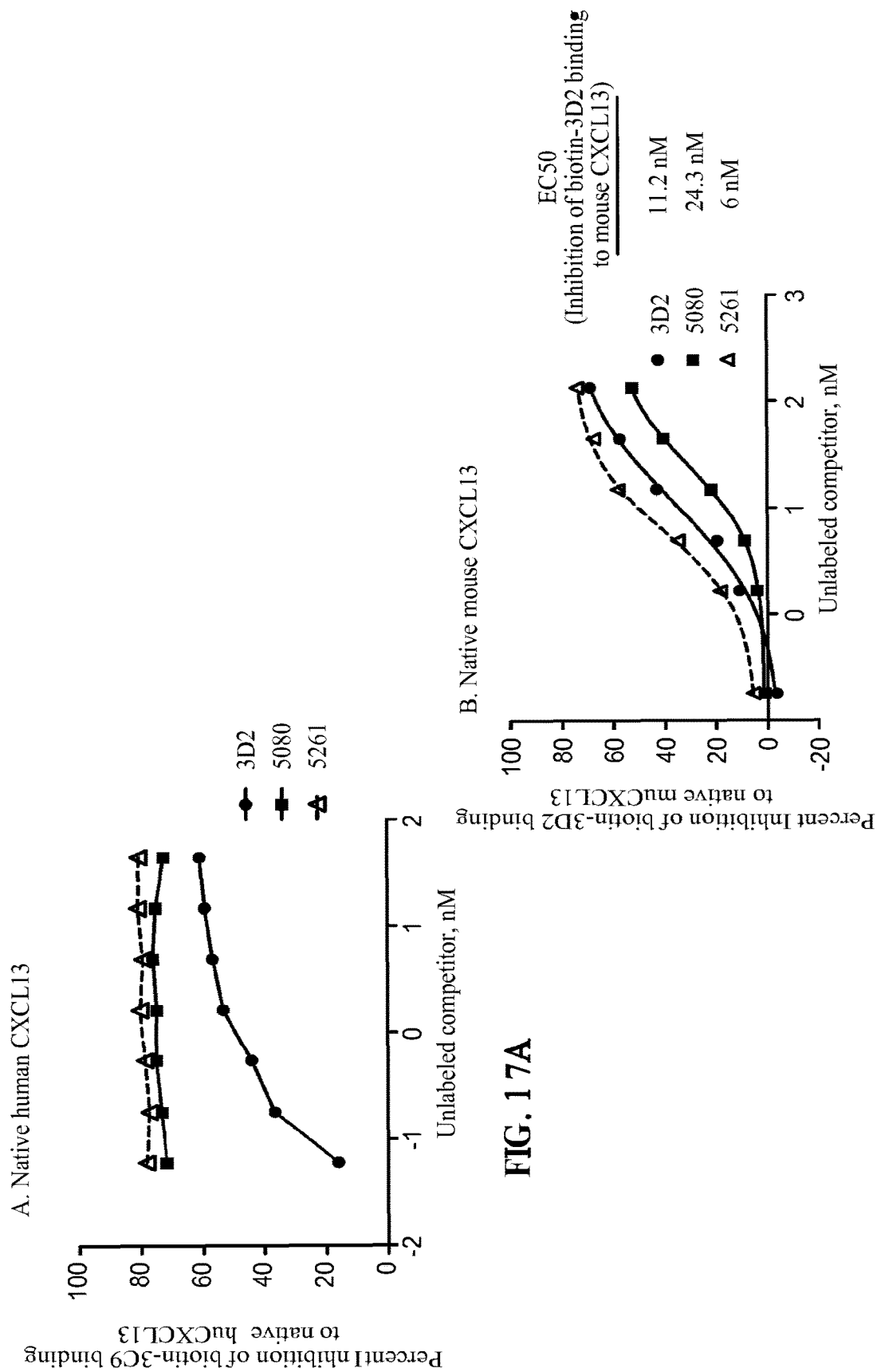

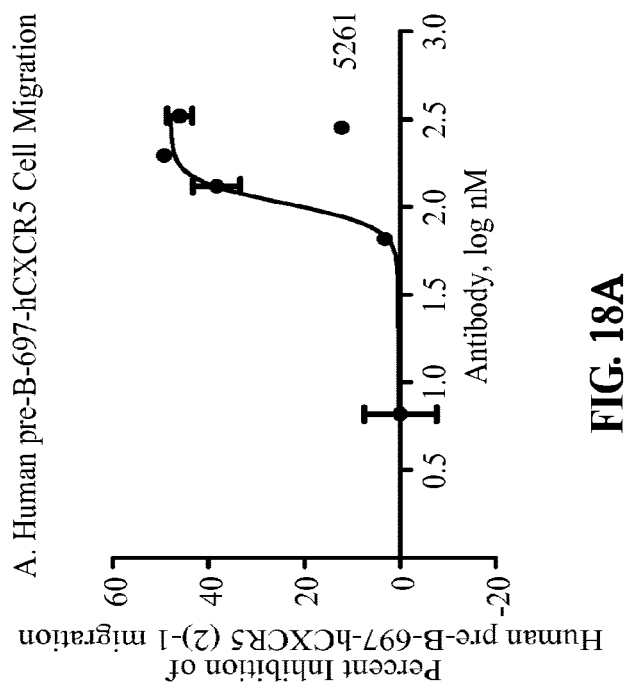
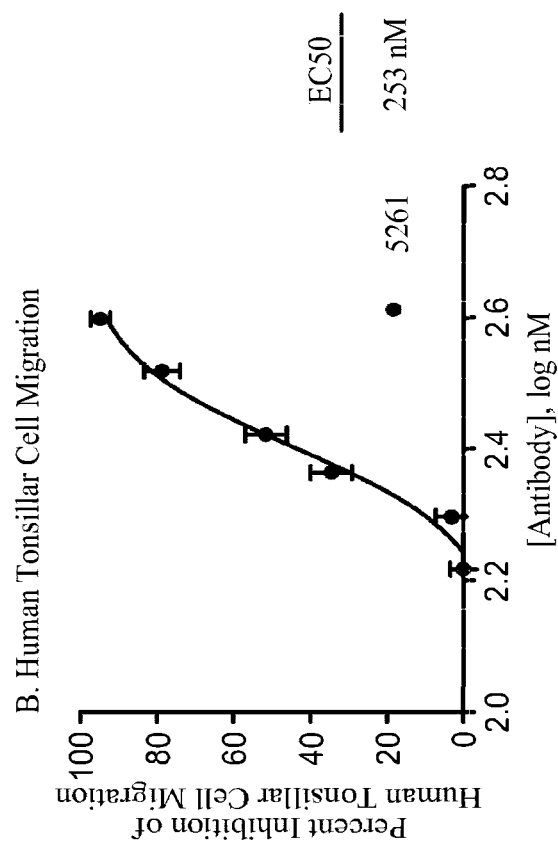
FIG. 18A
FIG. 18B

H5188 DNA sequence:
CAGGTGCAGCTGCAGGAGAGCGGCCCAGGCCTGGTGAAGCCTAGCGAGACCCTGAGC
CTCACCTGCACCGTCAGCGGCTTTAGCCTGAGCACCTTTGGCATGGGCGTGGGCTGGA
TTAGACAGCCTCCAGGCAAGGGCCTGGAGTGGATTGCACACATTTGGTGGGATGATG
ATAGGAGATATAACCCAGCCCTGAAGAGCAGAGTGACCATCAGCAAGGACACCAGC
AAGAACCAGTTCAGCCTGAAGCTGAGCAGCGTGACCGCTGCCGACACCGCCGTGTAT
TACTGTGCCAGAATCGCCGGCTATTATGGCAGCAGAGACTGGTTTGCCTACTGGGGCC
AAGGCACCACGGTCAC CGTCTCCTCA   (SEQ ID NO: 12)

H5188 Amino Acid sequence:
QVQLQESGPGLVKPSETLSLTCTVSGFSLS<u>TFGMGVG</u>WIRQPPGKGLEWIA<u>HIWWDDDRR
YNPALKS</u>RVTISKDTSKNQFSLKLSSVTAADTAVYYCAR<u>IAGYYGSRDWFAY</u>WGQGTTV
TVSS   (SEQ ID NO: 13)

L5153: DNA sequence
GACATCCAGATGACCCAGTCTCCATCCTCCCTGTCTGCATCTGTGGGAGACAGAGTCA
CCATCACTTGCAGAGCCAGCGAAAGTGTTGATAATATGGGCATTAGTTTTATGCACTG
GTATCAGCAGAAACCAGGGAAAGCCCCTAAGCTCCTGATCTTTAGAGCATCCGACCT
GGAATCTGGGGTCCCATCAAGGTTCAGTGGCAGTGGATCTGGGACAGATTTCACTCTC
ACCATCAGCAGTCTGCAACCTGAAGATTTTGCAACTTACTACTGTCAGCAAAGTAATA
AGGATCCCTGGACCTTCGGCCAAGGGACCAAGCTCGAGATCAAA   (SEQ ID NO: 14)

L5153 Amino Acid sequence:
DIQMTQSPSSLSASVGDRVTITC<u>RASESVDNMGISFMH</u>WYQQKPGKAPKLLIF<u>RASDLESG</u>
VPSRFSGSGSGTDFTLTISSLQPEDFATYYC<u>QQSNKDPWT</u>FGQGTKLEIK (SEQ ID NO: 15)

FIG. 21

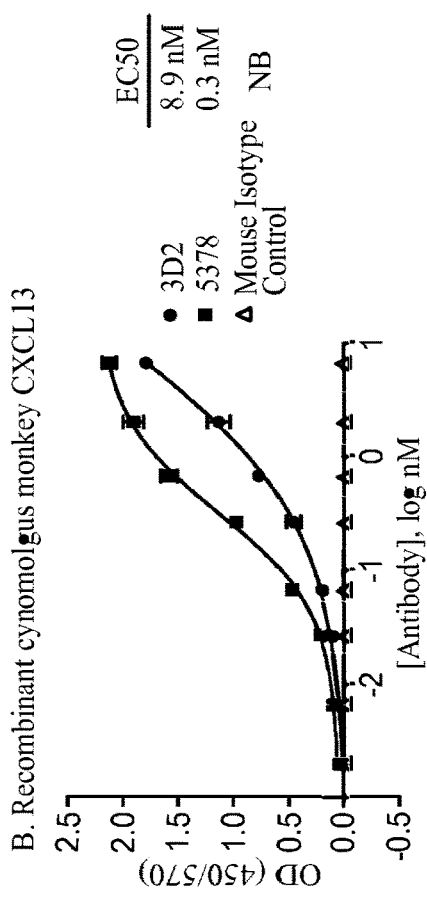
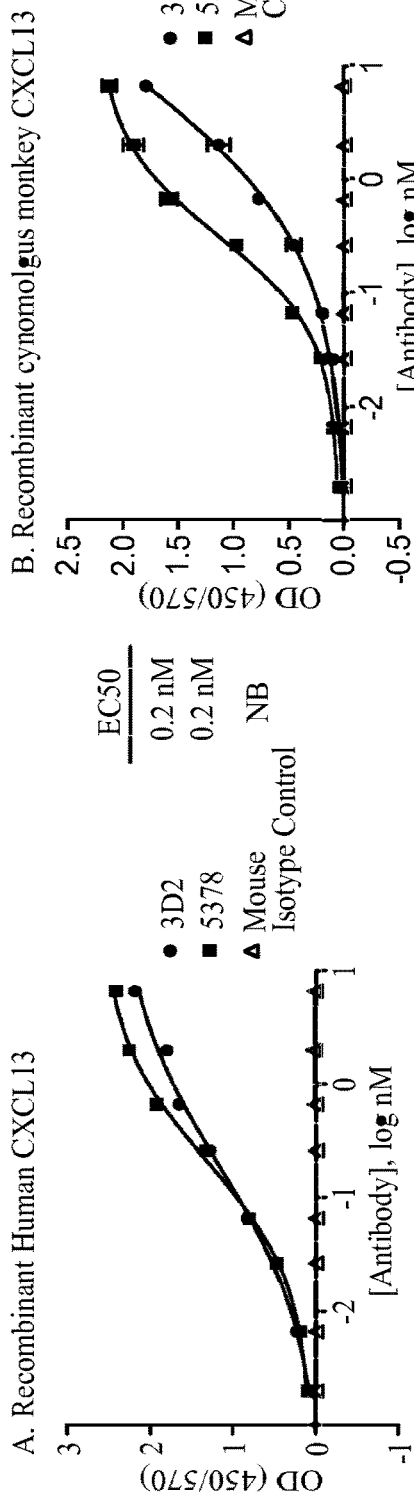
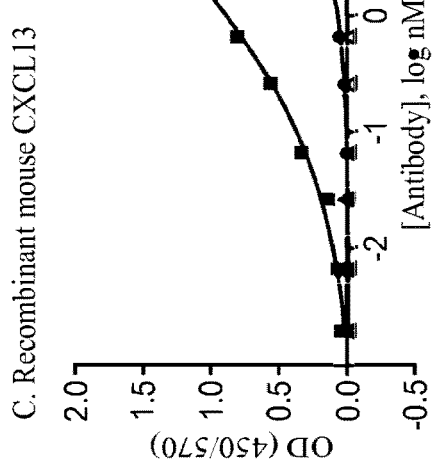
FIG 23 A
FIG. 23 B
FIG. 23C

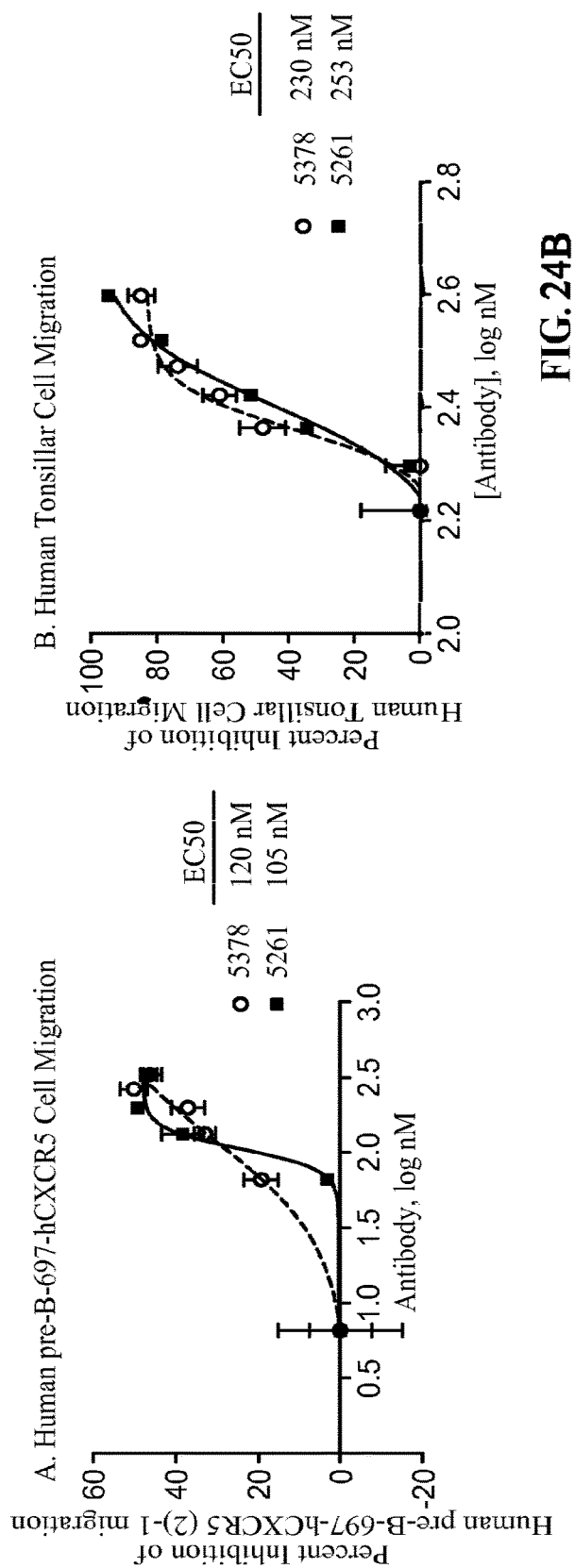
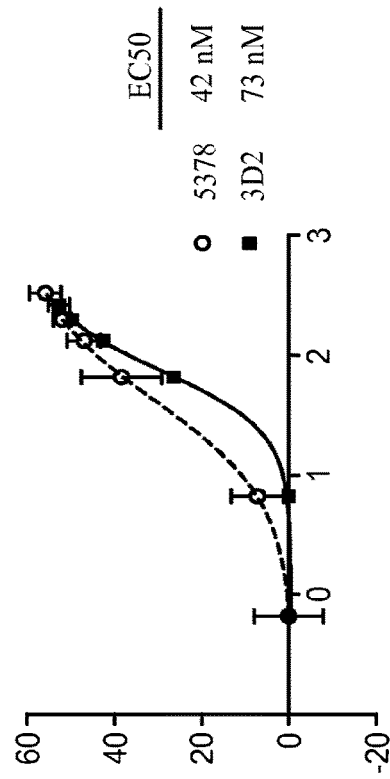
FIG. 24A
FIG. 24B
FIG. 24C

ANTI-CXCL13 ANTIBODIES AND METHODS OF USING THE SAME

CROSS-REFERENCE TO RELATED APPLICATIONS

This patent application is a divisional of U.S. patent application Ser. No. 15/953,139, filed Apr. 13, 2018, which is a divisional of U.S. patent application Ser. No. 13/820,278, filed Apr. 19, 2013, which is a National Phase of PCT Patent Application No.: PCT/US2011/050177, filed Sep. 1, 2011, and claims priority benefit of U.S. Provisional Patent Application No. 61/379,672, filed Sep. 2, 2010 and U.S. Provisional Patent Application No. 61/481,645, filed May 2, 2011, which are hereby incorporated by reference in their entireties.

REFERENCE TO SEQUENCE LISTING SUBMITTED ELECTRONICALLY

The content of the electronically submitted sequence listing in ASCII text file (Name: "sequencelisting_ascii.txt"; Size: 17,042 bytes; and Date of Creation: Apr. 13, 2018) filed with the application is incorporated herein by reference in its entirety.

BACKGROUND OF THE INVENTION

Homeostatic B Cell-Attracting chemokine 1 (BCA-1), otherwise known as CXCL13 (or ANGIE, BLC, BLR1L, ANGIE2, or Scyb13), is constitutively expressed in secondary lymphoid organs (e.g., spleen, lymph nodes, and Peyer's patches) by follicular dendritic cells (FDCs) and macrophages. See Gunn et al., *Nature* 391:799-803 (1998) and Carlsen et al., *Blood* 104(10):3021-3027 (2004). CXCL13 primarily acts through G-protein-coupled CXCR5 receptor (Burkitt's lymphoma receptor 1). CXCR5 is expressed, e.g., on mature B lymphocytes, CD4+ follicular helper T cells (Thf cells), a minor subset of CD8+ T cells, and activated tonsillar Treg cells. See Legler et al., *J. Exp. Med.* 187:655-660 (1998); Förster et al., *Blood* 84:830-840 (1994); Fazilleau et al., *Immunity* 30:324-335 (2009); Ansel et al., *J. Exp. Med.* 190:1123-1134 (1999); Lim et al., *J. Clin. Invest.* 114(11):1640-1649 (2004); and R. Förster, Chapter in Academic Press Cytokine Reference, August 2000.

Generation of B-cells having the potential for autoantibody (antibody against self-antigen) production is common under normal physiological conditions. However, such natural autoantibodies are low affinity IgM antibodies that exhibit wide-spectrum reactivity and strong a preference for soluble self antigens over cell surface antigens (see, e.g., Dichiero et al., *J. Immunol.* 134(2):765-771 (1985); Cote et al., *Proc. Natl. Acad. Sci* 83:2959-2963 (1986)). Autoreactive low-affininty B-cells undergo apoptosis and, therefore, are unlikely to present a danger to a healthy organism.

In the absence of infection and during a normal immune response, CXCL13 and its receptor CXCR5 are involved in the homing of B-cells and follicular B-helper T cells into primary follicles in lymph nodes and spleen; germinal center formation; and lymphoid organogenesis. See, e.g., Förster et al., *Cell* 87:1037-1047 (1996).

CXCL13 and CXCR5-deficient mice demonstrated impaired development of Peyer patches and lymph nodes due to the lack of organized follicles. See Ansel et al., *Nature* 406:309-314 (2000). Furthermore, immunization with T-cell-dependent antigen in the context of the CXCL13 knockout phenotype led to the formation of misplaced and abnormally small germinal centres in the lymph nodes and spleens (Ansel et al.).

In a chronically-inflamed environment, ectopic germinal centres form within affected (often non-lymphoid) tissues. CXCL13 over-expression in these germinal centres by follicular dendritic cells (FDCs), accompanied by disregulation in interactions among FDCs, B-cells and follicular Th cells, reduced elimination of autoreactive B-cells and subsequent, antigen-driven, generation of affinity-mature long-lived plasma cells and memory B-cells producing high affinity IgG autoantibodies, which can result in the development of autoimmune and inflammatory disorders. See, e.g., Vinuesa et al., *Immunology* 9:845-857 (2009). Furthermore, over-expression of CXCR5 receptor in certain cancers has been reported to promote CXCL13-dependent cell proliferation and metastasis.

High-level expression of CXCL13 (BCA-1) and its receptor, CXCR5, has been observed in *H. pylori*-induced gastric lymphoid follicles and mucosa-associated lymphoid tissue (MALT) lymphomas. See, e.g., Mazzucchelli et al., *J Clin Invest* 104:R49-R54 (1999). Furthermore, CXCL13 (BCA-1) expression was found in all samples of *H. pylori*-induced gastritis. Id. In the gastric mucosa of *H. heilmannii*-infected wild-type mice, the mRNA expression level of CXCL13, which is known to be involved in organogenesis of lymphatic tissues (including MALT), was significantly higher than that of uninfected mice. See Nobutani et al., *FEMS Immunol Med Microbiol* 60:156-164 (2010).

The need for therapies that target CXCL13-mediated signaling pathways has become increasingly apparent in the recent years. The mechanisms of action for such treatments would include, e.g., blockade of CXCL13 interaction with its receptor resulting in interference with B cell and follicular B-helper T cell migration into inflamed tissues and germinal center formation (e.g., in the case of autoimmune disease) and inhibition of cancer cell proliferation and ability to spread in oncological disorders.

FIELD OF THE INVENTION

The invention relates to CXCL13 neutralizing binding molecules, e.g., antibodies and antigen binding fragments thereof, e.g., humanized monoclonal antibodies, methods of using the binding molecules, and methods for treatment of conditions and diseases associated with CXCL13-expressing cells.

BRIEF SUMMARY OF THE INVENTION

One aspect the invention relates to an isolated antigen binding molecule which specifically binds to the same CXCL13 epitope as a reference monoclonal antibody selected from the group consisting of MAb 5261, MAb 5378, MAb 5080, MAb 1476, 3D2, and 3C9. In certain embodiments, the antigen binding molecule specifically binds to the same CXCL13 epitope as MAb 5261 and MAb 5378.

In another aspect, the invention relates to an isolated antigen binding molecule which specifically binds to CXCL13, wherein said binding molecule competitively inhibits a reference monoclonal antibody selected from the group consisting of MAb 5261, MAb 5378, MAb 5080, MAb 1476, 3D2, and 3C9 from specifically binding to CXCL13. In certain embodiments, the antigen binding molecule competitively inhibits MAb 5261 and MAb 5378. In another embodiment, the antibody or fragment thereof is selected from the group consisting of MAb 5261, MAb 5378, MAb 5080, MAb 1476, 3D2, and 3C9.

In one embodiment of the invention, the isolated antibody or antigen-binding fragment thereof specifically binds to CXCL13 and the heavy chain variable region (VH) of said antibody or fragment thereof comprises an amino acid sequence at least 90% identical to a sequence selected from the group consisting of SEQ ID NO: 13 and SEQ ID NO: 3. In another embodiment, the light chain variable region (VL) of the antibody or fragment thereof comprises an amino acid sequence at least 90% identical to a sequence selected from the group consisting of SEQ ID NO: 15, SEQ ID NO: 17, and SEQ ID NO: 8.

In another embodiment, the isolated antibody or antigen-binding fragment thereof specifically binds to CXCL13 and the VH of said antibody or fragment thereof comprises an amino acid sequence identical, except for 20 or fewer conservative amino acid substitutions, to a sequence selected from the group consisting of SEQ ID NO: 13 and SEQ ID NO: 3. In another embodiment, the VL of the antibody or fragment thereof comprises an amino acid sequence identical, except for 20 or fewer conservative amino acid substitutions, to a sequence selected from the group consisting of SEQ ID NO: 15, SEQ ID NO: 17, and SEQ ID NO: 8.

In certain embodiments, the isolated antibody or antigen-binding fragment thereof specifically binds to CXCL13 and the VH and VL of the antibody or fragment thereof comprise amino acid sequences at least 90% identical to VH and VL sequences selected from the group consisting of: (a) SEQ ID NO: 13 and SEQ ID NO: 15, respectively; (b) SEQ ID NO: 13 and SEQ ID NO: 17, respectively; and (c) SEQ ID NO: 3 and SEQ ID NO: 8, respectively. In yet another embodiment, the isolated antibody or antigen-binding fragment thereof specifically binds to CXCL13, wherein the VH and VL of said antibody or fragment thereof comprise amino acid sequences identical, except for 20 or fewer conservative amino acid substitutions each, to VH and VL sequences selected from the group consisting of: (a) SEQ ID NO: 13 and SEQ ID NO: 15, respectively; (b) SEQ ID NO: 13 and SEQ ID NO: 17, respectively; and (c) SEQ ID NO: 3 and SEQ ID NO: 8, respectively.

In one embodiment, the isolated antibody or antigen-binding fragment thereof specifically binds to CXCL13 and the VH of said antibody or fragment thereof comprises a Chothia-Kabat heavy chain complementarity determining region-1 (VH-CDR1) amino acid sequence identical, except for two or fewer amino acid substitutions, to SEQ ID NO: 4; a Kabat heavy chain complementarity determining region-2 (VH-CDR2) amino acid sequence identical, except for four or fewer amino acid substitutions, to SEQ ID NO: 5; a Kabat heavy chain complementarity determining region-3 (VH-CDR3) amino acid sequence identical, except for two or fewer amino acid substitutions, to SEQ ID NO: 6; a Kabat light chain complementarity determining region-1 (VL-CDR1) amino acid sequence identical, except for four or fewer amino acid substitutions, to SEQ ID NO: 16 or 9; a Kabat light chain complementarity determining region-2 (VL-CDR2) amino acid sequence identical, except for two or fewer amino acid substitutions, to SEQ ID NO: 10; or a Kabat light chain complementarity determining region-3 (VL-CDR3) amino acid sequence identical, except for two or fewer amino acid substitutions, to SEQ ID NO: 11.

In certain embodiments, the isolated antibody or antigen-binding fragment thereof specifically binds to CXCL13 and the VH of said antibody or fragment thereof comprises VH-CDR1, VH-CDR2, and VH-CDR3 amino acid sequences comprising SEQ ID NOs: 4, 5, and 6, respectively, except for four or fewer amino acid substitutions in one or more of said VH-CDRs. In another embodiment, the isolated antibody or antigen-binding fragment thereof specifically binds to CXCL13 and the VL of said antibody or fragment thereof comprises VL-CDR1, VL-CDR2, and VL-CDR3 amino acid sequences comprising SEQ ID NOs: 16 or 9, 10, and 11, respectively, except for four or fewer amino acid substitutions in one or more of said VL-CDRs.

In some embodiments, the antibody or fragment thereof of the invention inhibits CXCL13 from binding to a CXCL13 receptor. In certain embodiments, the CXCL13 receptor is CXCR5. In another embodiment, the antibody or fragment thereof of the invention is humanized, primatized or chimeric.

Another aspect of the invention is directed to a composition comprising the antibody or fragment thereof of the invention, and a carrier.

A further aspect of the invention is directed to an isolated polynucleotide comprising a nucleic acid encoding an antibody VH polypeptide, wherein the amino acid sequence of said VH polypeptide is at least 90% identical to a sequence selected from the group consisting of SEQ ID NO: 12 and SEQ ID NO: 2. In another aspect, the invention is directed to an isolated polynucleotide comprising a nucleic acid encodes an antibody VL polypeptide, wherein the amino acid sequence of said VL polypeptide is at least 90% identical to a sequence selected from the group consisting of SEQ ID NO: 7 and SEQ ID NO14; and wherein an antibody or antigen binding fragment thereof comprising said VL polypeptide specifically binds to CXCL13.

In one embodiment, the isolated polynucleotide comprises a nucleic acid encoding an antibody VH polypeptide, wherein the amino acid sequence of the VH polypeptide is identical, except for 20 or fewer conservative amino acid substitutions, to a sequence selected from the group consisting of SEQ ID NO: 2 and SEQ ID NO: 12. In another embodiment, the isolated polynucleotide comprises a nucleic acid encoding an antibody VL polypeptide, wherein the amino acid sequence of the VL polypeptide is identical, except for 20 or fewer conservative amino acid substitutions, to a sequence selected from the group consisting of SEQ ID NO: 7, SEQ ID NO: 14, and SEQ ID NO: 18; and wherein an antibody or antigen binding fragment thereof comprising said VL polypeptide specifically binds to CXCL13.

A further aspect of the invention is directed to a vector comprising the polynucleotide of the invention. Another aspect is directed to a host cell comprising a vector of the invention. The invention is also directed to methods of producing an antibody or fragment thereof which specifically binds CXCL13, comprising culturing a host cell of the invention, and recovering said antibody, or fragment thereof.

Another aspect of the invention is directed to methods for neutralizing CXCL13 in an animal, comprising administering to said animal a composition comprising: an isolated antibody or fragment thereof or a composition of the invention; and a pharmaceutically acceptable carrier.

Further embodiments of the invention are directed to methods for treating an autoimmune disease or an inflammatory disease or cancer in an animal in need of treatment, comprising administering to said animal a composition comprising: an isolated antibody or fragment thereof or a composition of the invention; and a pharmaceutically acceptable carrier. In some embodiments, the autoimmune disease or said inflammatory disease is multiple sclerosis, Systemic Lupus Erythematosis (SLE), or arthritis, e.g., rheumatoid arthritis.

A further aspect of the invention is directed to methods for reducing or inhibiting gastric lymphoid follicles in an animal, comprising administering to said animal a composition comprising an isolated antibody or fragment thereof of the invention and a pharmaceutically acceptable carrier. A further embodiment of the invention is directed to a method for preventing or treating mucosa-associated lymphoid tissue (MALT) lymphoma or a gastric or duodenal ulcer in an animal in need of prevention or treatment, comprising administering to said animal a composition comprising an isolated antibody or fragment thereof of the invention and a pharmaceutically acceptable carrier. In one embodiment, the animal has been infected with a *Heliobacter* bacterium. In one embodiment the *Heliobacter* bacterium is *H. pylori* or *H. heilmannii*.

BRIEF DESCRIPTION OF THE DRAWINGS/FIGURES

FIG. 1A-1C. Specificity ELISA results showing the binding of mouse anti-human CXCL13 antibodies (3D2 and 3C9) to recombinant human CXCL13 (FIG. 1A), recombinant mouse CXCL13 (FIG. 1B), and recombinant cynomolgus monkey CXCL13 (FIG. 1C) compared to antibody controls (mouse MAb 801 and/or rat MAb 470). EC50 values are shown and were obtained with four-parameter sigmoidal curve fit (curves are shown on the graph; the $R^2$ for the curves that produced EC50 values was 0.99).

FIG. 2. Epitope Competition ELISA results showing the percent inhibition of biotinylated 3D2 binding to human CXCL13 for mouse anti-human CXCL13 antibodies (3C9 and 3D2) compared to results with no competitor or MAb 801.

FIG. 3A-B. Capture Epitope Competition ELISA results showing 3D2 inhibition of biotin-3C9 binding to native or recombinant human CXCL13 (FIG. 3A) and biotin-3D2 binding to native or recombinant mouse CXCL13 (FIG. 3B). Curves were fitted using four-parameter sigmoidal curve fit (curves are shown on the graph; the $R^2=0.99$). The differences in EC50 values were analyzed by unpaired t-test and were found to be P>0.05.

Figure 4B:
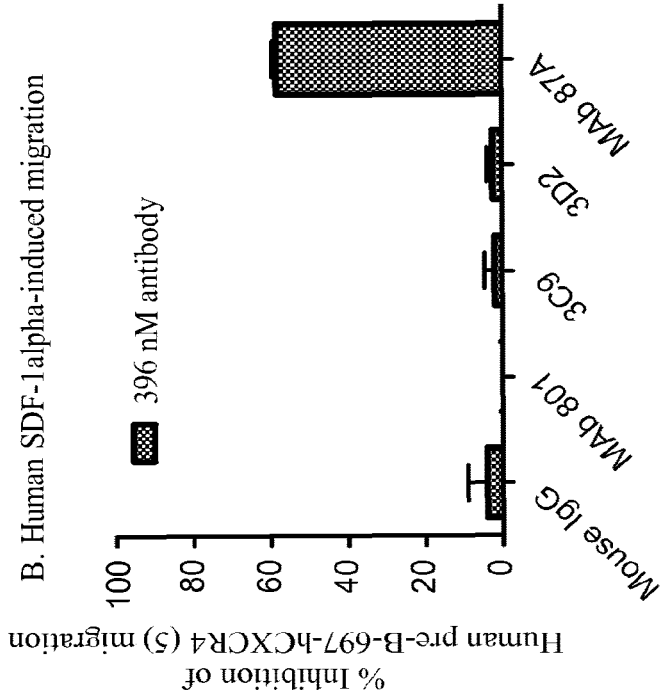
Figure 4A:
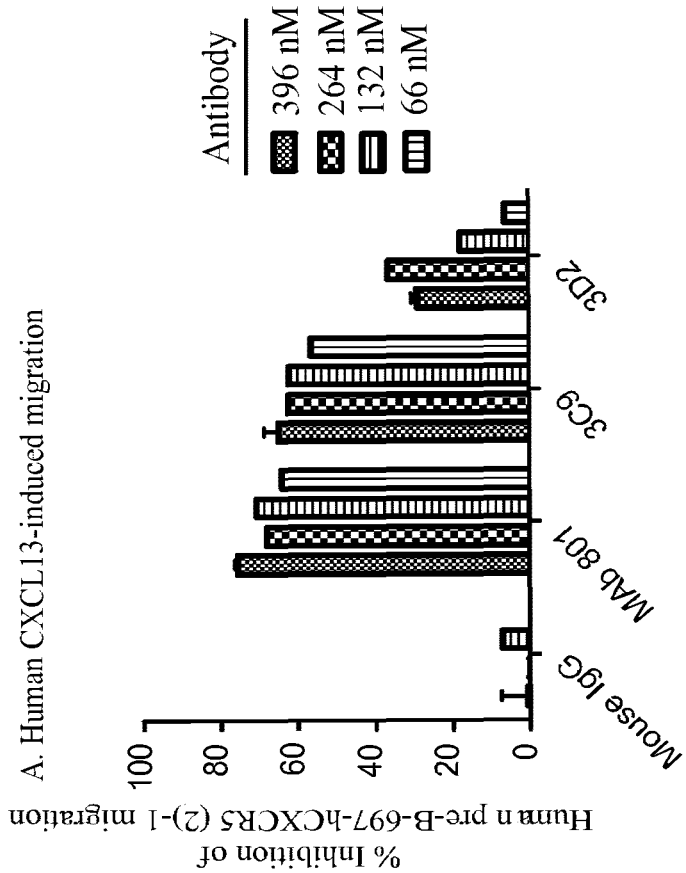

FIG. 4A-B. B-cell migration results showing the effect of 3D2 and 3C9 on human CXCL13 induced migration of human pre-B-697-hCXCR5 cells (FIG. 4A) and human SDF-1 alpha induced migration of pre-B-697-hCXCR4 cells (FIG. 4B). Mouse IgG was used as a negative control. MAb 801 was used as a positive control for inhibition of human CXCL13 migration, and MAb 87A was used as a positive control for inhibition of human SDF-1 alpha-induced migration.

Figure 5A:
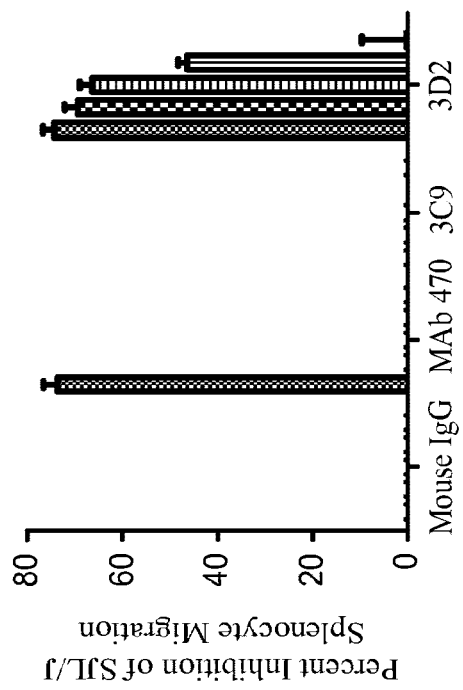
Figure 5B:
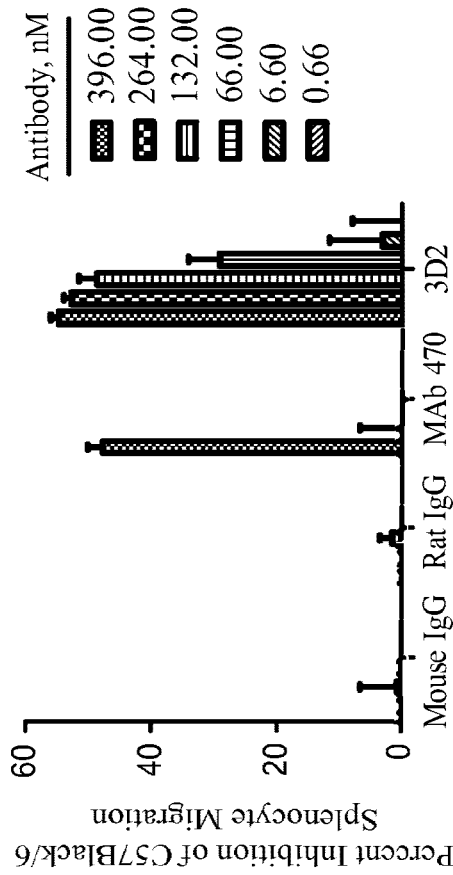
Figure 5C:
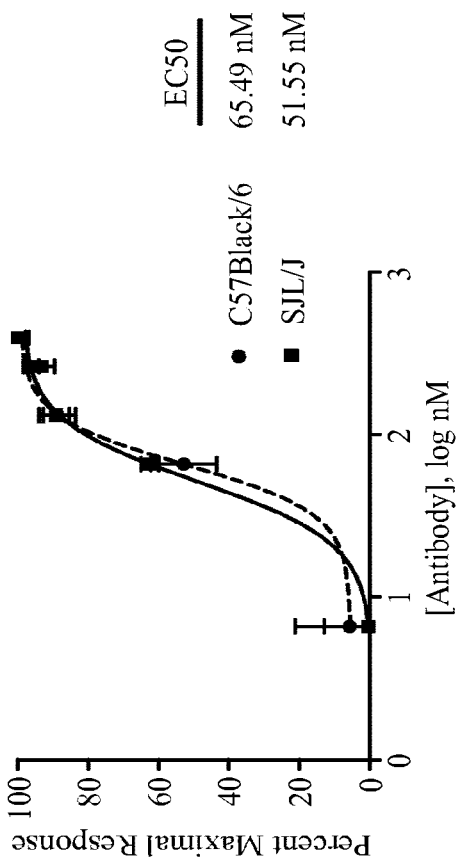

FIG. 5A-C. Percent inhibition of splenocyte migration in C57Black/6 by 3D2, MAb 470, Mouse IgG (control), or Rat IgG (control) (FIG. 5A) and in SJL/J by 3D2, 3C9, MAb 470, or Mouse IgG (control) (FIG. 5B). The results are presented as mean of two (C57Black/6 migration) independent experiments+/−SD and three (SJL/J migration) independent experiments+/−SEM. A comparison of the effect of 3D2 on C57Black/6 and SJL/J migration (FIG. 5C) was analyzed by unpaired t-test which produced P value >0.05. Curves were fitted using four-parameter sigmoidal curve fit (curves are shown on the graph; $R^2=0.99$).

FIG. 6A-C. CXCL13-mediated endocytosis results for human CXCL13-mediated endocytosis (FIG. 6A) and mouse CXCL13-mediated endocytosis (FIG. 6B) of human and mouse CXCR5 receptors by 3D2 or controls (MAb 470 and/or Mouse IgG). A comparison of human and mouse CXCL13-mediated endocytosis EC50 values was calculated from sigmoidal dose response curves with $R^2$ values equal to 1 (mouse endocytosis) and 0.994 (human endocytosis) is shown (FIG. 6C). The data comparing 3D2 effect on human and mouse receptor endocytosis was analyzed by unpaired t-test which produced P value >0.05.

Figure 7:
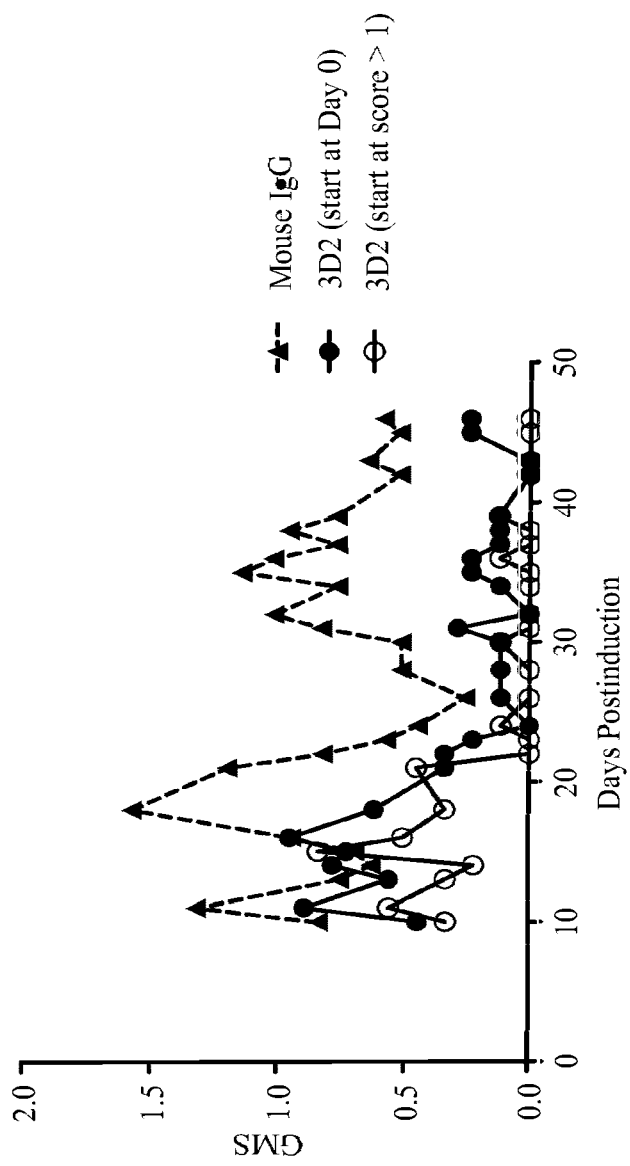

FIG. 7. EAE disease progression in mice treated with 3D2 (start at Day 0), 3D2 (start at Score >1), or Mouse IgG control (RR-EAE-1 Study). Each data point represents a mean of scores taken from 9 mice. Group means (GMS) were compared by using one-way ANOVA followed by Bonferroni's multiple comparison post test.

Figure 8:
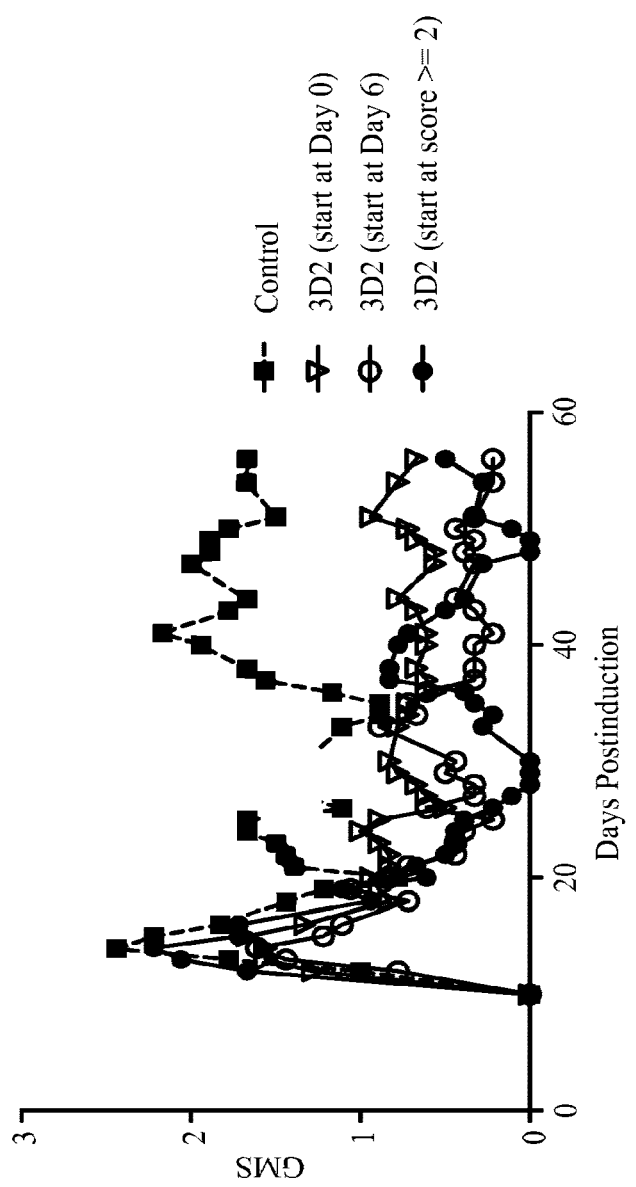

FIG. 8. EAE disease progression in mice treated with 3D2 (start at Day 0), 3D2 (start at Day 6), 3D2 (start at Day >2), or Mouse IgG control (RR-EAE-2 Study). Each data point represents a mean of scores taken from 9 mice. Group means (GMS) were compared by using one-way ANOVA followed by Bonferroni's multiple comparison post test.

Figures 9A, 9B:
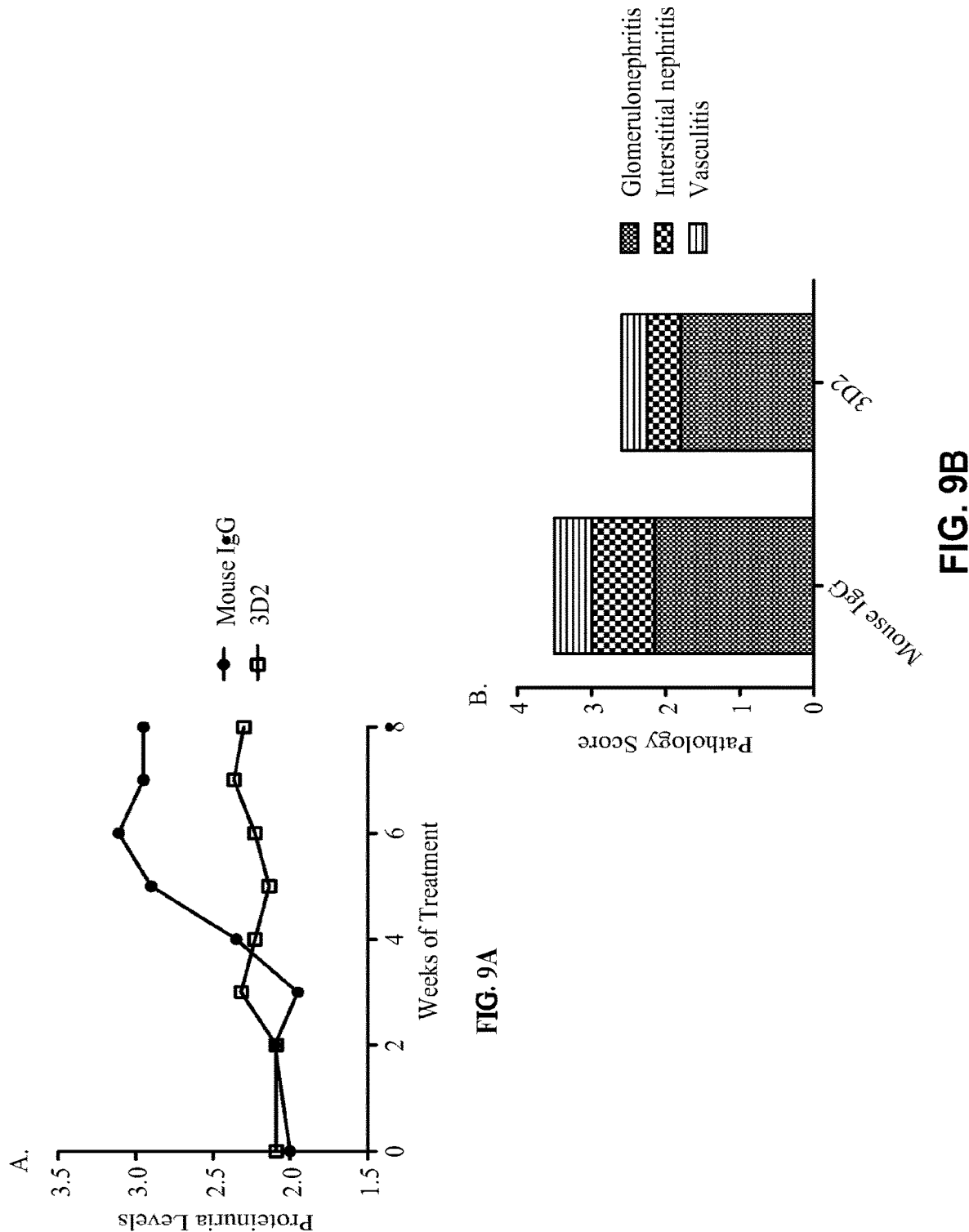

FIG. 9A-B. Kidney pathology in mice with advanced lupus nephritis after 3D2 or Mouse IgG (control) treatment (SLE-1 Study). For proteinurea scores (FIG. 9A) and kidney pathology scores for Glomerulonephritis, Interstitial nephritis, and Vasculitis (FIG. 9B), each data point represents mean of ten measurements.

Figures 10, 10A:
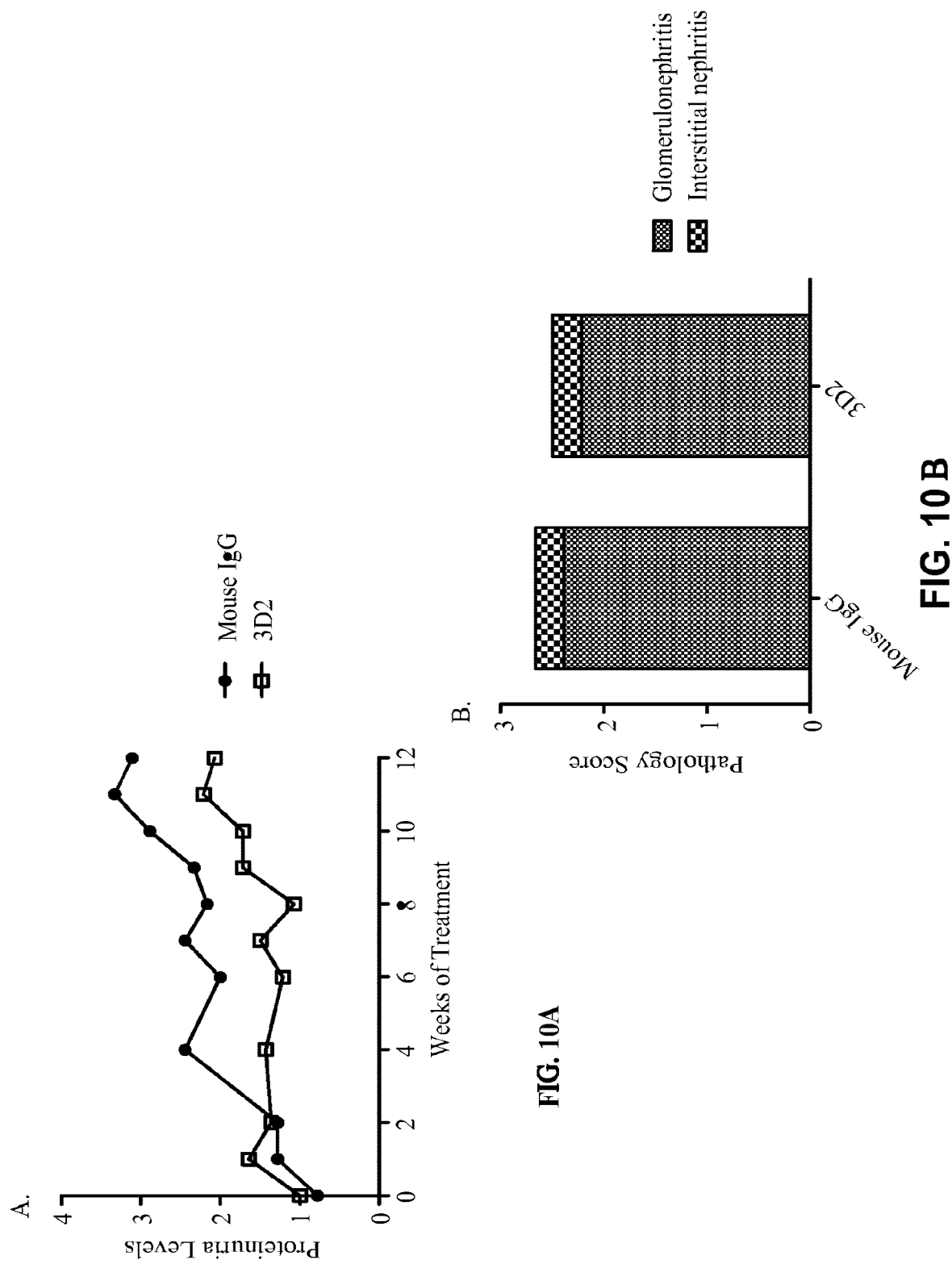

FIG. 10A-B. Kidney pathology in mice with early lupus disease after 3D2 and Mouse IgG (control) treatment (SLE-2 Study). For proteinurea scores (FIG. 10A) and kidney pathology scores for Glomerulonephritis and Interstitial nephritis (FIG. 10B) each data point represents 7 mice from 3D2-treated group and 9 mice from mouse IgG-treated group.

FIG. 11A-B. Histology sections showing the effect of 3D2 on the number of germinal centers (GCs) and primary follicles in lupus mouse spleen. Spleen sections were stained with GL-7 (GC stain), B220 antibody (B cell marker), or antibody against follicular dendritic cells (FDCs) from 3D2-treated (FIG. 11A) and mouse IgG-treated (FIG. 11B) NZB/NZWF1 mice.

Figures 12A, 12B:
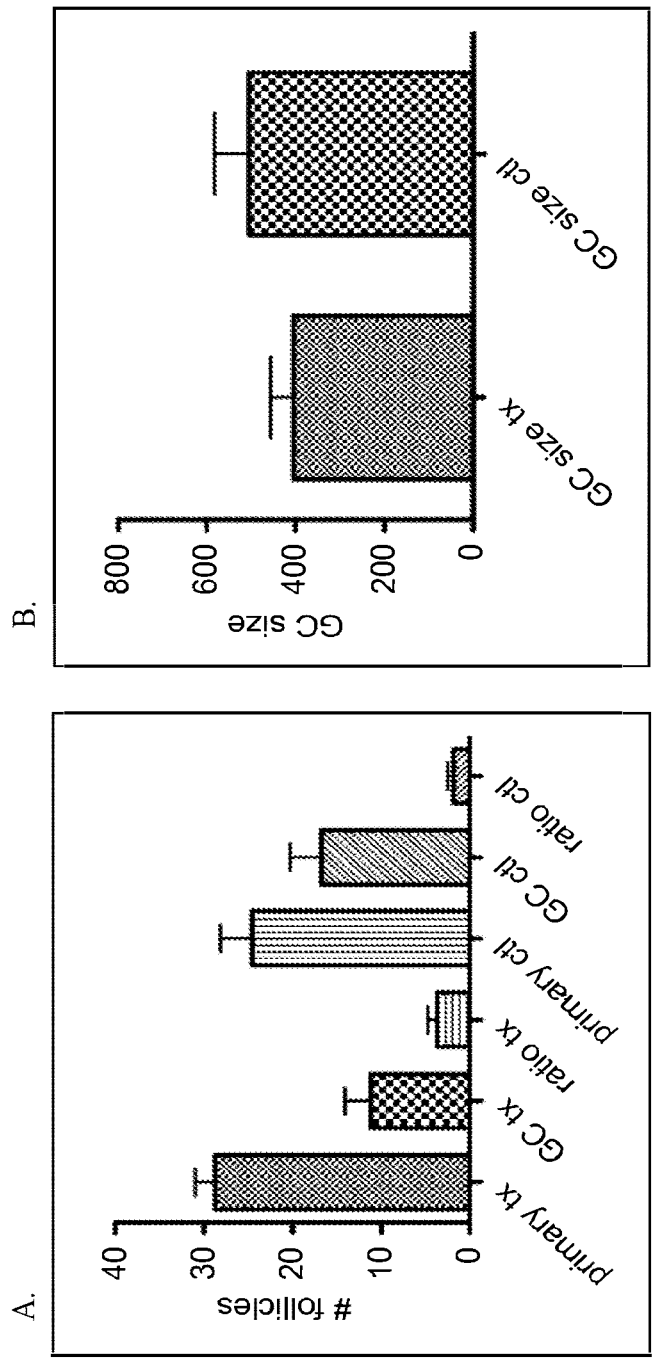

FIG. 12A-B. Primary follicles and GC size in spleen of lupus mice treated with 3D2. Values are shown as mean+/−SEM with 5 mice per group. Mice treated with 3D2 ("tx") showed a trend towards decreased numbers of GCs when expressed as a ratio of primary:secondary (GC) follicles (p=0.19) (FIG. 12A) and a significant decrease in GC size (p=0.03) (FIG. 12B).

FIG. 13. Polynucleotide and amino acid sequences of 3D2 Variable Heavy Chain (H1609) and Variable Light Chain (L0293). Complementarity determining regions (CDRs) are underlined.

Figures 14A, 14B:
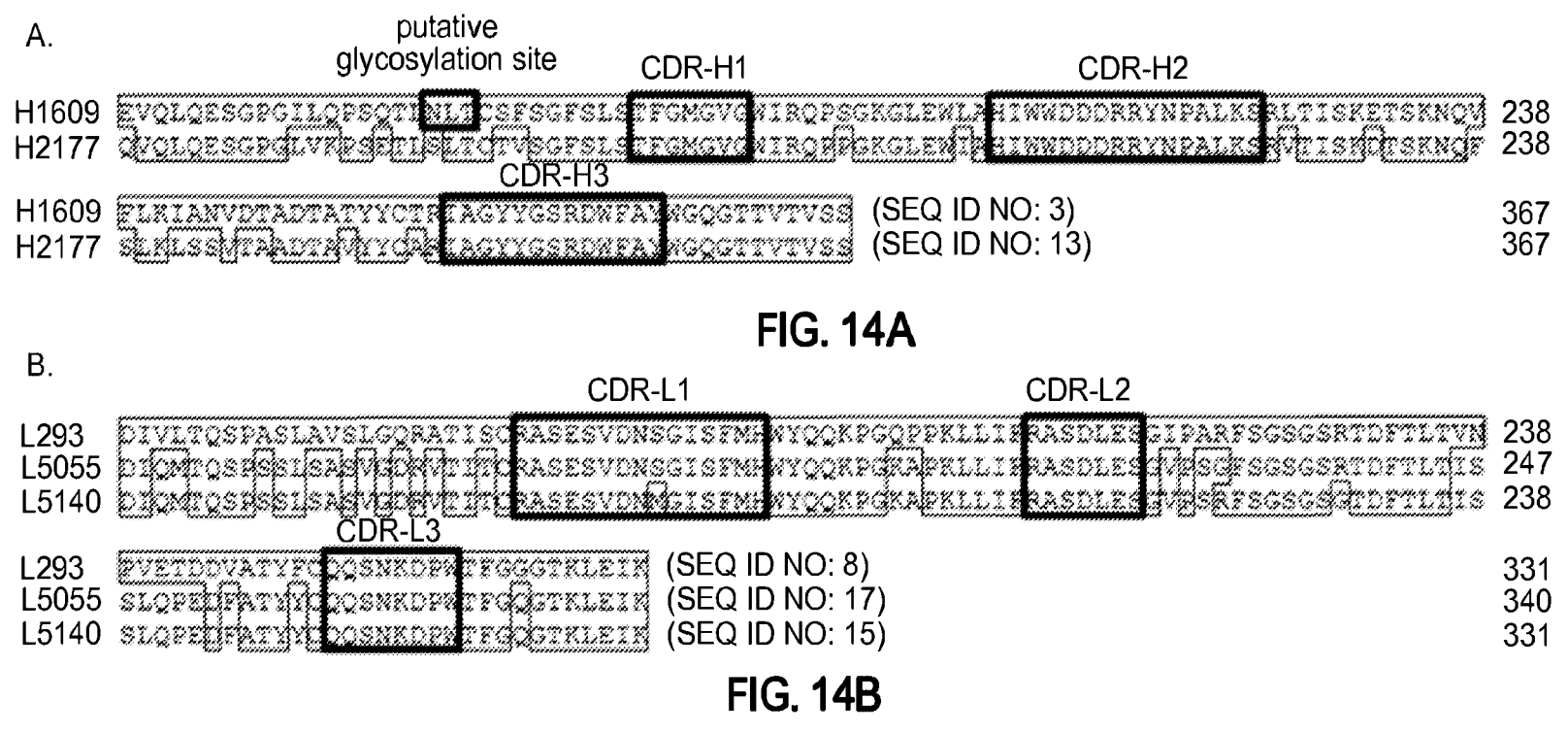

FIG. 14A-B. Amino acid sequences for humanization of chimeric 3D2 showing the modification of Variable Heavy Chain H1609 to H2177 (FIG. 14A) and Variable Light Chain L0293 to L5055 to L5140 (FIG. 14B). The putative glycosylation site and complementarity determining regions (CDRs) are boxed.

FIG. 15. Polynucleotide and amino acid sequences of MAb 5261 Variable Heavy and Light Chains (H2177/L5140) and MAb 5080 Variable Heavy and Light Chains (H2177/L5055). Complementarity determining regions (CDR) are underlined.

Figure 16B:
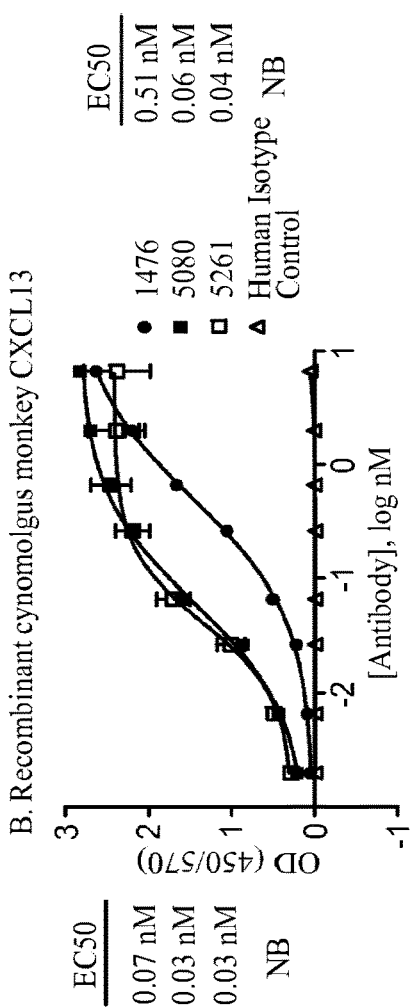
Figure 16A:
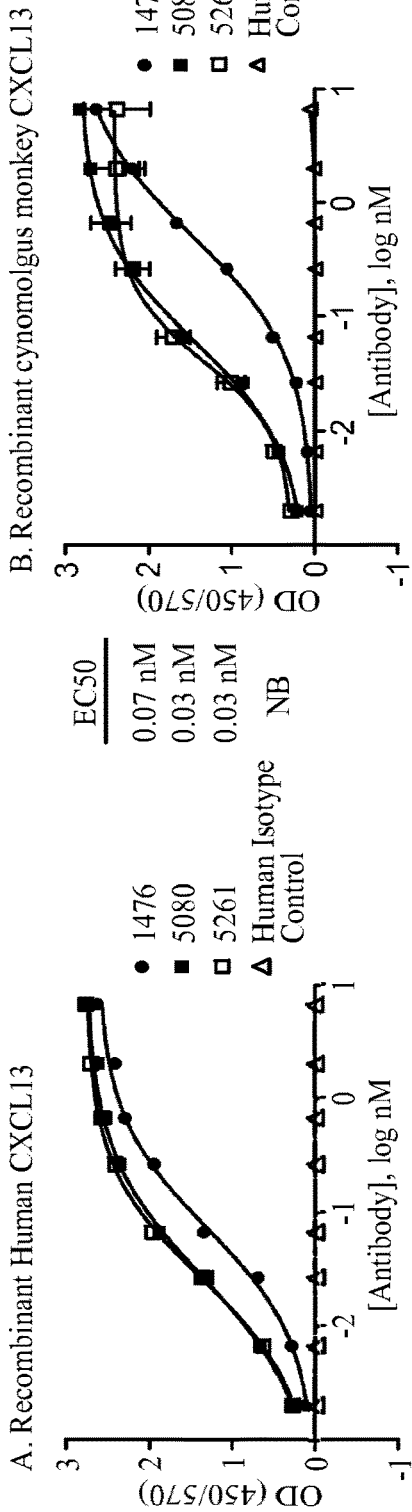
Figure 16C:
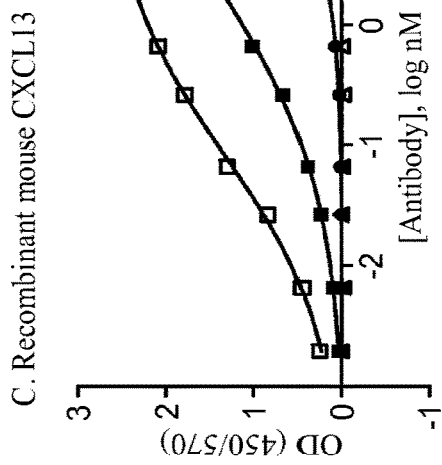

FIG. 16A-C. Specificity ELISA results for MAb 5261, MAb 5080, MAb 1476, and Human Isotype Control binding to recombinant human (FIG. 16A), cynomolgus monkey (FIG. 16B) and mouse (FIG. 16C) CXCL13. Each data point represents mean of triplicate measurements. EC50 values were calculated from four-parameter sigmoidal curve fit (curves are shown on the graph; $R^2$ for the curves that produced EC50 values were 0.99). NB=no binding.

FIG. 17A-B. Capture Epitope Competition ELISA results for MAb 5261, MAb 5080, and 3D2 binding to native human (FIG. 17A) and native mouse (FIG. 17B) CXCL13. Each data point represents an average of duplicate measurements from one of at least three independent experiments. Curves were fitted using four-parameter sigmoidal curve fit (curves are shown on the graph; $R^2$=0.99).

FIG. 18A-B. Percent Inhibition of human pre-B-697-hCXCR5 (FIG. 18A) and human tonsillar cell (FIG. 18B) migration by MAb 5261. Data represent an average of triplicate measurements+/–SEM from one of at least three experiments. Curves were fitted using four-parameter sigmoidal curve fit (curves are shown on the graph; $R^2$=0.98-0.99).

Figure 19:
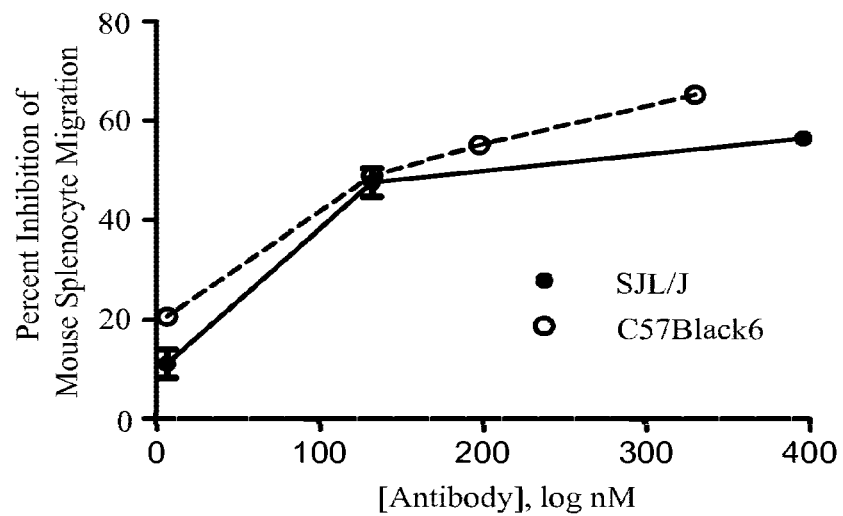

FIG. 19. Percent Inhibition of SJL/J and C57Black/6 Splenocyte Migration by MAb 5261. Data from representative experiments are shown as mean of duplicate measurements+/–SD.

Figure 20:
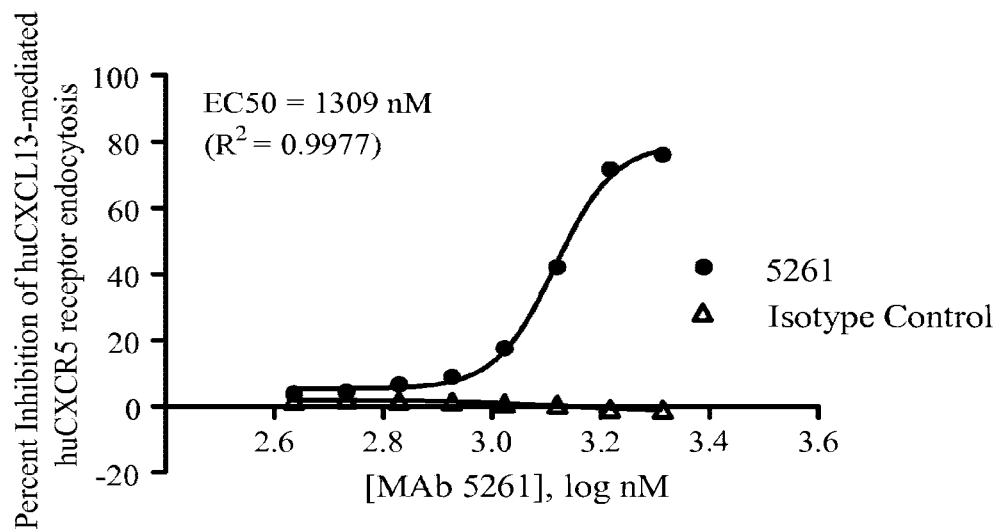

FIG. 20. Percent Inhibition of human CXCL13-mediated internalization of human CXCR5 receptor by MAb 5261 and Isotype Control. Data are average of triplicate measurements from one of at least three independent experiments. Curve was fitted using four-parameter sigmoidal curve fit (curves are shown on the graph; $R^2$=0.99).

FIG. 21. Polynucleotide and amino acid sequence of MAb 5378 Variable Heavy Chain (H5188) and Variable Light Chain (L5153). Complementarity determining regions (CDRs) are underlined.

Figure 22:
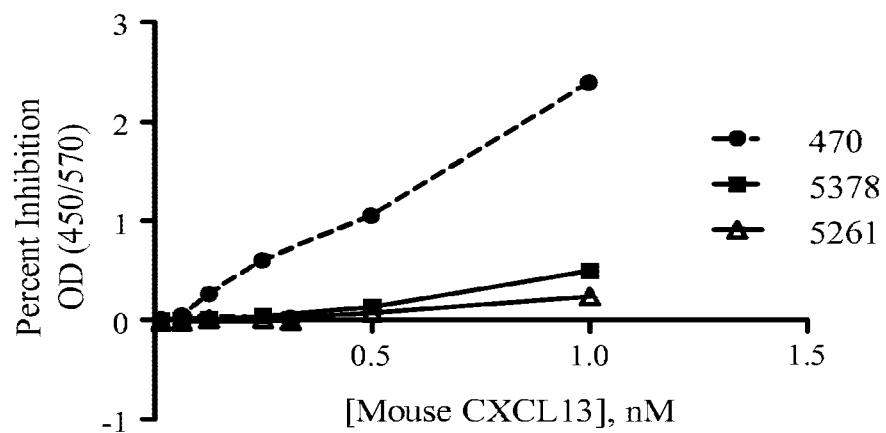

FIG. 22. Epitope Competition ELISA results for MAb 5378, MAb 5261, and MAb 470.

FIG. 23A-C. Specificity ELISA results for MAb 5378, 3D2, and Mouse Isotype Control binding to recombinant human (FIG. 23A), cynomolgus monkey (FIG. 23B) and mouse (FIG. 23C) CXCL13. Each data point represents mean of triplicate measurements. EC50 values were calculated from four-parameter sigmoidal curve fit (curves are shown on the graph; $R^2$ for the curves that produced EC50 values were 0.99).

FIG. 24A-C. Percent Inhibition of human pre-B-697-hCXCR5 (FIG. 24A), human tonsillar cells (FIG. 24B) and C57Black6 mouse spleenocyte (FIG. 24C) migration by MAb 5261 or MAb 5378 (FIG. 24A-B) and MAb 5378 or 3D2 (FIG. 24C). Data represent an average of triplicate measurements+/–SEM from one of at least three experiments. Curves were fitted using four-parameter sigmoidal curve fit (curves are shown on the graph; $R^2$=0.99).

Figure 25:
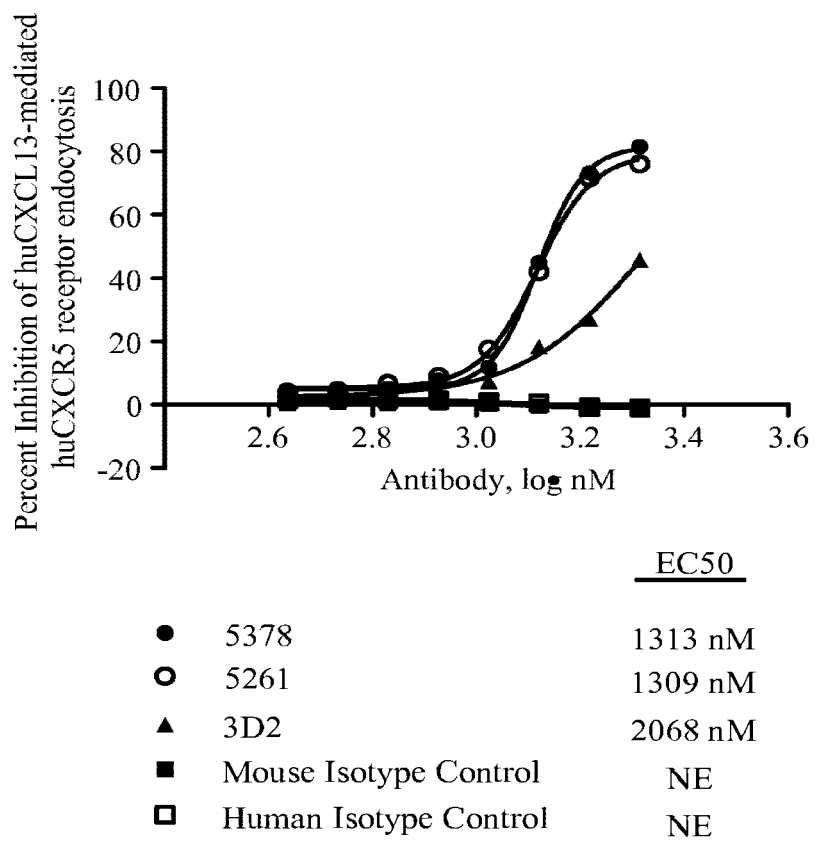

FIG. 25. Percent Inhibition of human CXCL13-mediated internalization of human CXCR5 receptor by MAb 5378, MAb 5261, 3D2, Mouse Isotype Control, or Human Isotype Control. Data points for 5261 and 5378 represent average of measurements from two independent experiments. Data points for 3D2 and Isotype Controls represent average of triplicate measurements from a single experiment. Curve was fitted using four-parameter sigmoidal curve fit (curves are shown on the graph; $R^2$=0.99). NE=no effect.

Figure 26:
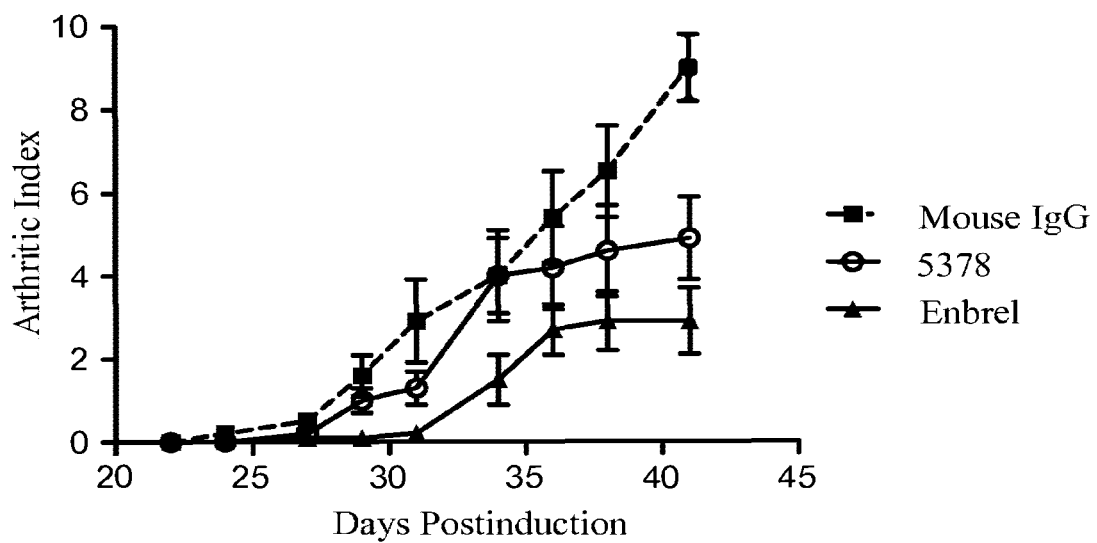

FIG. 26. Collagen-induced arthritis (CIA) disease progression in mice treated with MAb 5376, etanercept, or Mouse IgG (control) (CIA-1 Study). Each data point represents a mean of scores taken from 10 mice. Group means were compared by using one-way ANOVA followed by Bonferroni's multiple comparison post test.

Figure 27:
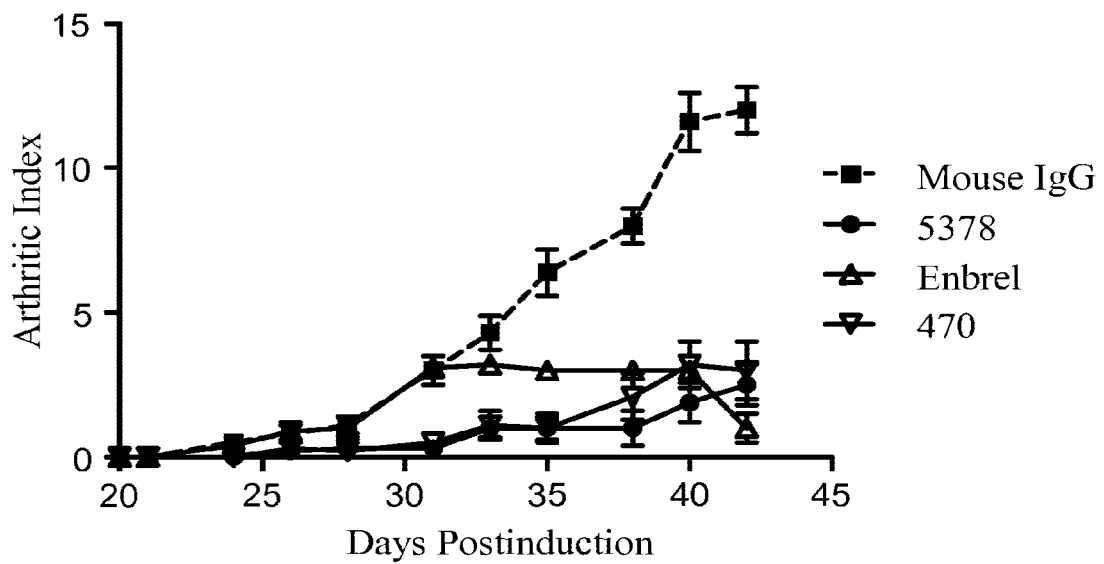

FIG. 27. Collagen-induced arthritis (CIA) disease progression in mice treated with MAb 5378, etanercept, MAb 470, or Mouse IgG (control) (CIA-2 Study). Each data point represents a mean of scores taken from 10 mice. Group means were compared by using one-way ANOVA followed by Bonferroni's multiple comparison post test.

Figure 28:
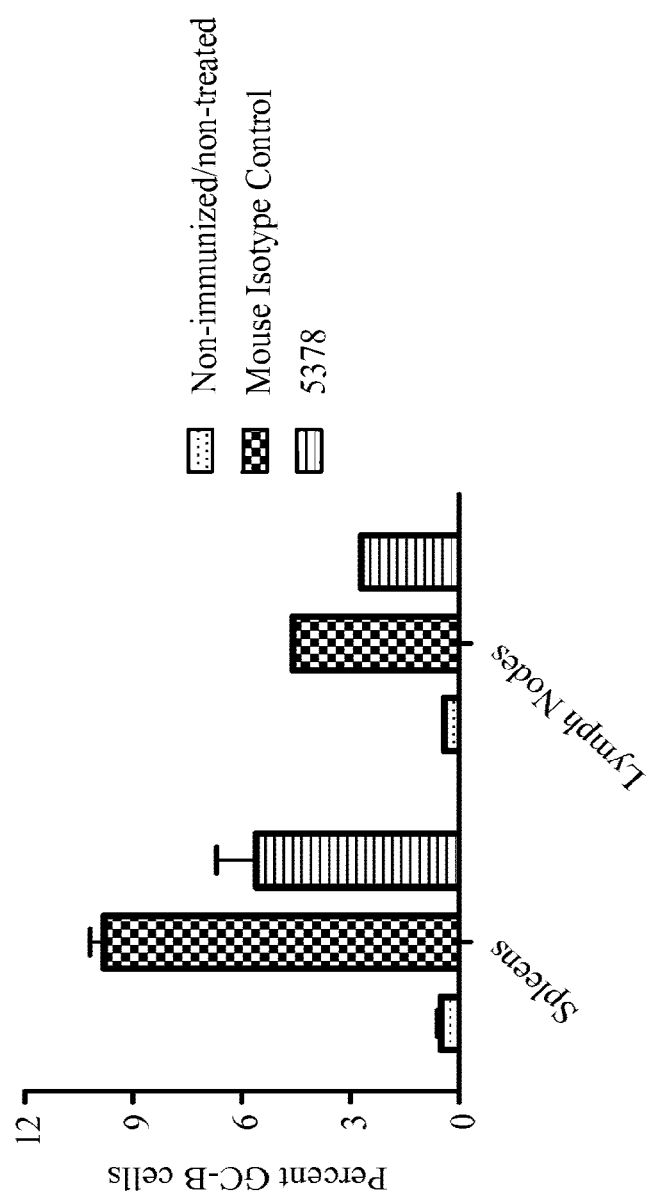

FIG. 28. Germinal center formation in NP-CGG immunized mice treated with MAb 5378, Mouse Isotype Control, or no treatment (GC-1 Study). Each spleen data point represents a mean of values measured from three mice. Each lymph node data point represents a single value obtained from pooled cells collected from three mice.

Figure 29:
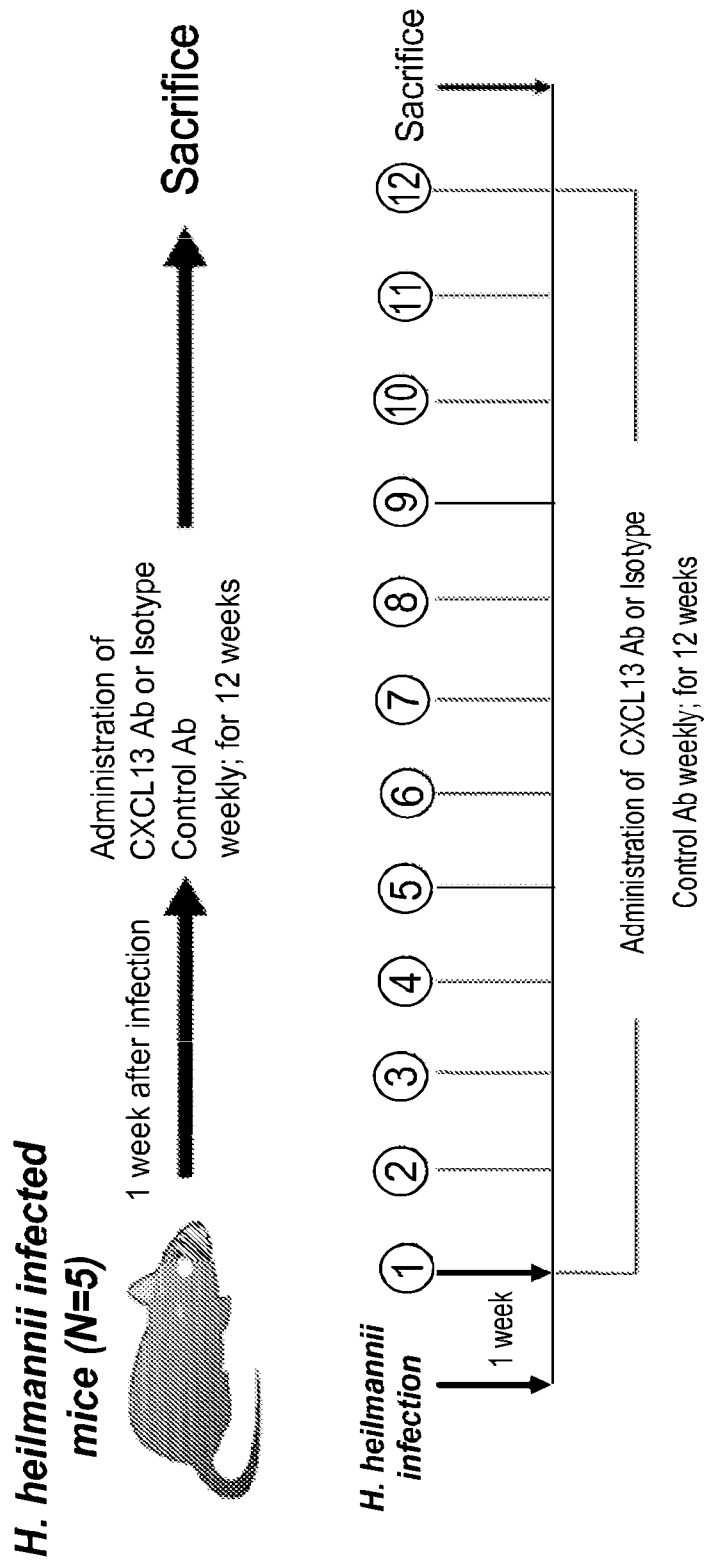

FIG. 29. Treatment schedule for *H. heilmannii* infection of mice and antibody administration.

Figure 30:
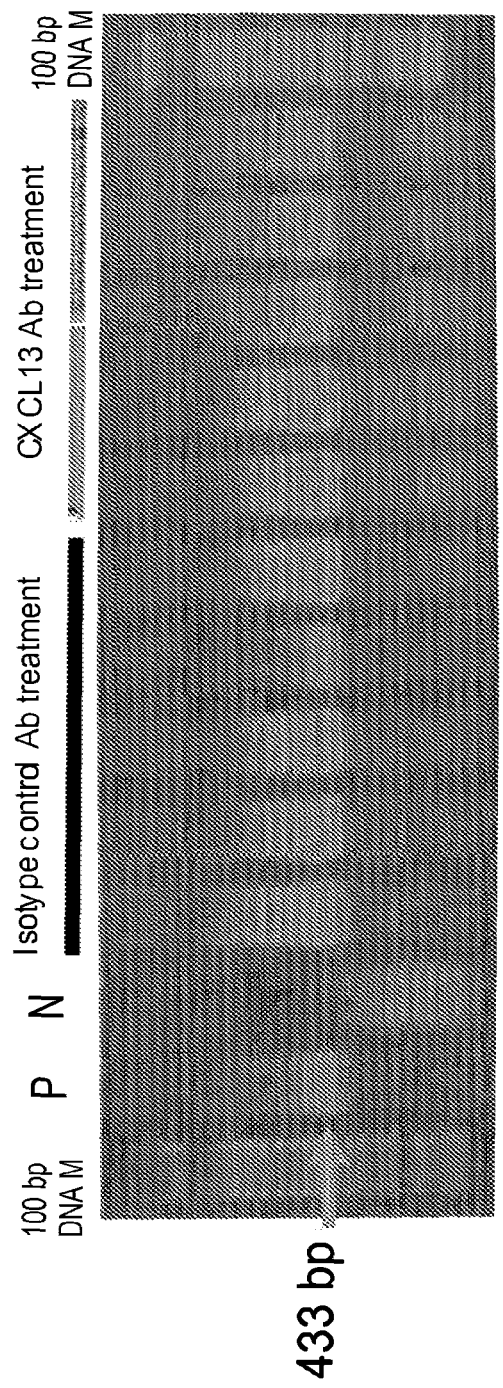

FIG. 30. *H. heilmannii* specific 16s rRNA genes were amplified in all gastric samples obtained from *H. heilmannii* infected mice including isotype control antibody treatment and anti-CXCL13 antibody treatment. Positive control (P) and negative control (N) are also shown.

Figures 31A, 31B:
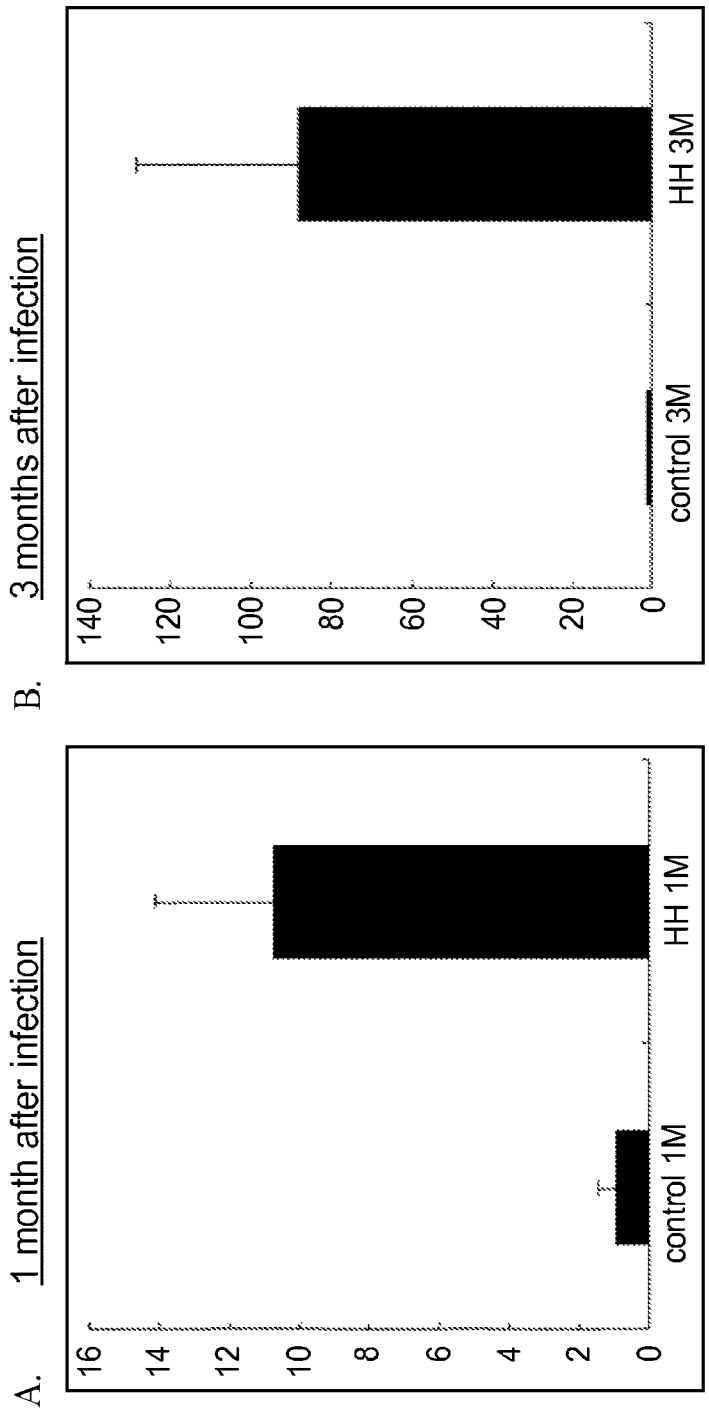

FIG. 31A-B. The mRNA expression level of CXCL13 in the gastric mucosa of *H. heilmannii* (HH) infected wild-type (WT) mice 1 month (FIG. 31A) and 3 months (FIG. 31B) after infection as determined by real-time quantitative PCR (values are normalized to mouse beta-actin expression levels in each sample).

Figure 32:
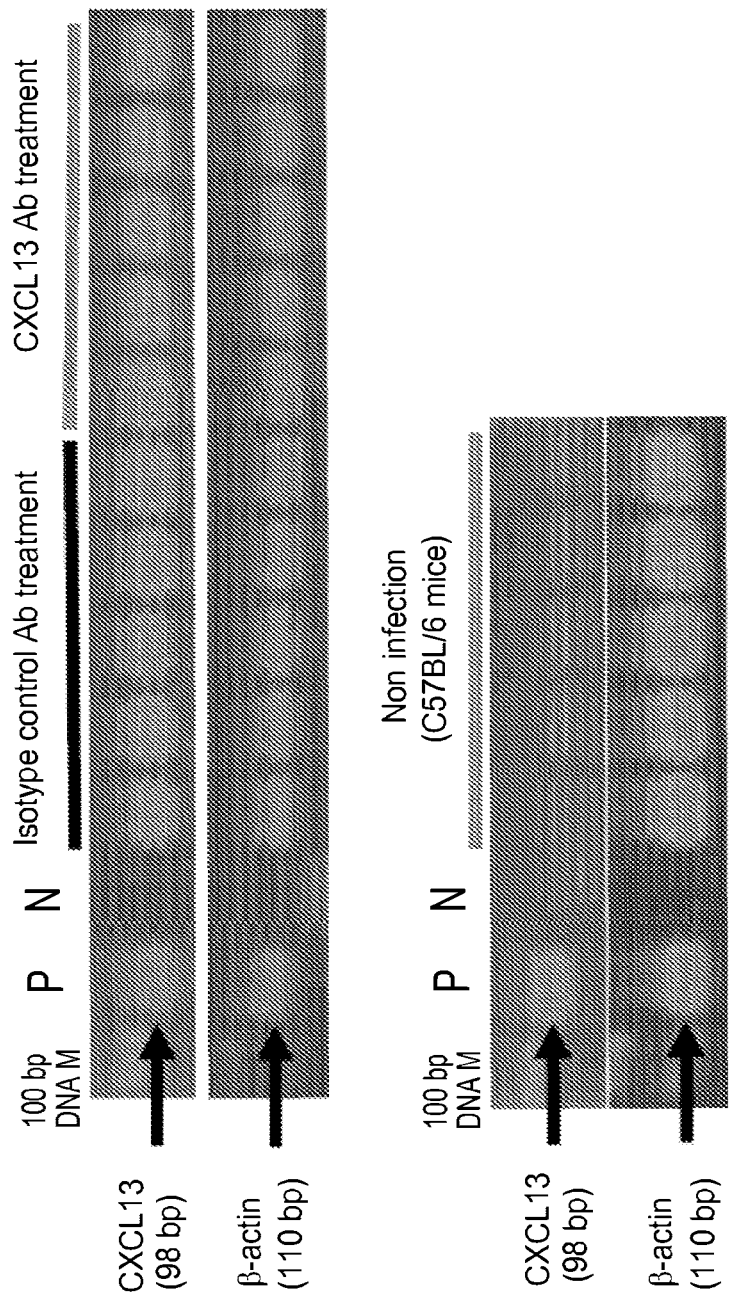

FIG. 32. The expression of CXCL13 mRNA and β-actin in the stomach of *H. heilmannii* infected mice after isotype control antibody or anti-CXCL13 antibody treatment (upper panel). The expression of CXCL13 mRNA and β-actin in the stomach of noninfected mice (lower panel). Positive control (P) and negative control (N) are also shown.

Figure 33:
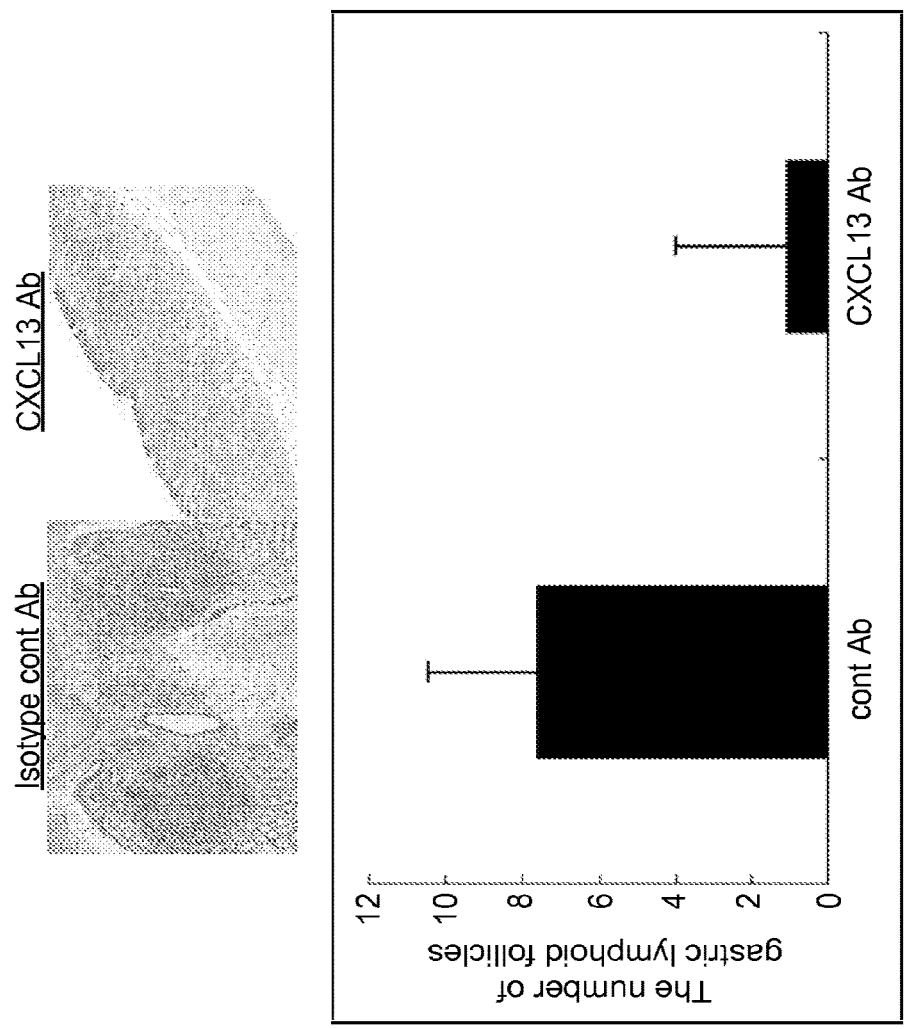

FIG. 33. Hematoxylin and eosin (H&E) stained stomach samples from isotype control antibody treated mouse (upper left panel) and anti-CXCL13 antibody treated mouse (upper right panel) three months after *H. heilmannii* infection. The lower panel shows the number of gastric lymphoid follicles identified in stomach samples from isotype control antibody and anti-CXCL13 antibody treated mice.

DETAILED DESCRIPTION OF THE INVENTION

Definitions

It is to be noted that the term "a" or "an" entity refers to one or more of that entity; for example, "an anti-CXCL13 antibody" is understood to represent one or more anti-CXCL13 antibodies. As such, the terms "a" (or "an"), "one or more," and "at least one" can be used interchangeably herein.

As used herein, the term "tumor" refers to all neoplastic cell growth and proliferation, whether malignant or benign, and all cancerous and pre-cancerous cells and tissues.

The terms, "cancer" and "cancerous" refer to or describe the physiological condition in mammals that is typically characterized by unregulated cell growth. Examples of cancer include but are not limited to carcinomas, lymphomas and leukemias.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides that do not possess a defined three-dimensional structure, but rather can adopt a large number of different conformations, are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purpose of the invention, as are native or recombinant polypeptides that have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative," and "analog" when referring to anti-CXCL13 antibodies or antibody polypeptides of the present invention include any polypeptides that retain at least some of the antigen-binding properties of the corresponding antibody or antibody polypeptide of the invention. Fragments of polypeptides of the present invention include proteolytic fragments, as well as deletion fragments, in addition to specific antibody fragments discussed elsewhere herein. Variants of anti-CXCL13 antibodies and antibody polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions, or additions. Variant polypeptides may also be referred to herein as "polypeptide analogs." As used herein a "derivative" of an anti-CXCL13 antibody or antibody polypeptide refers to a subject polypeptide having one or more residues chemically derivatized by reaction of a functional side group. Also included as "derivatives" are those peptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. Derivatives of anti-CXCL13 antibodies and antibody polypeptides of the present invention, may include polypeptides that have been altered so as to exhibit additional features not found on the reference antibody or antibody polypeptide of the invention.

The term "polynucleotide" is intended to encompass a singular nucleic acid as well as plural nucleic acids and refers to an isolated nucleic acid molecule or construct, e.g., messenger RNA (mRNA) or plasmid DNA (pDNA). A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, that has been removed from its native environment. For example, a recombinant polynucleotide encoding an anti-CXCL13 binding molecule, e.g., an antibody or antigen binding fragment thereof, contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

As used herein, a "coding region" is a portion of nucleic acid that consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding an anti-CXCL13 antibody or fragment, variant, or derivative thereof. Heterologous coding regions include without limitation specialized elements or motifs, such as a secretory signal peptide or a heterologous functional domain.

In certain embodiments, the polynucleotide or nucleic acid is DNA. In the case of DNA, a polynucleotide comprising a nucleic acid that encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. These include, without limitation, transcription control regions that function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to, ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions that encode secretory or signal peptides, which direct the secretion of a polypeptide encoded by a polynucleotide of the present invention. According to the signal hypothesis, proteins secreted by mammalian cells have a signal peptide or secretory leader sequence that is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

A "binding molecule" or "antigen binding molecule" of the present invention refers in its broadest sense to a molecule that specifically binds an antigenic determinant. In one embodiment, the binding molecule specifically binds to CXCL13 (also called BCA-1). In another embodiment, a binding molecule of the invention is an antibody or an antigen binding fragment thereof, e.g., an anti-CXCL13 antibody. In another embodiment, a binding molecule of the invention comprises at least one heavy or light chain CDR of an antibody molecule. In another embodiment, a binding molecule of the invention comprises at least two CDRs from one or more antibody molecules. In another embodiment, a binding molecule of the invention comprises at least three CDRs from one or more antibody molecules. In another embodiment, a binding molecule of the invention comprises at least four CDRs from one or more antibody molecules. In another embodiment, a binding molecule of the invention comprises at least five CDRs from one or more antibody molecules. In another embodiment, a binding molecule of the invention comprises at least six CDRs from one or more antibody molecules. In certain embodiments, one or more of the CDRs is from MAb 5261, MAb 5378, MAb 5080, MAb 1476, 3D2, or 3C9.

The present invention is directed to certain anti-CXCL13 antibodies, or antigen-binding fragments, variants, or derivatives thereof. Unless specifically referring to full-sized antibodies such as naturally occurring antibodies, the term "anti-CXCL13 antibodies" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No. 5,939,598 by Kucherlapati et al. "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s).

"Human" or "fully human" antibodies also include "human" or "fully human" antibodies, as described above, that comprise, consist essentially of, or consist of, variants (including derivatives) of antibody molecules (e.g., the VH regions and/or VL regions) described herein, which antibodies or fragments thereof immunospecifically bind to a CXCL13 polypeptide or fragment or variant thereof. Standard techniques known to those of skill in the art can be used to introduce mutations in the nucleotide sequence encoding a human anti-CXCL13 antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3.

In certain embodiments, the amino acid substitutions are conservative amino acid substitutions, discussed further below. Alternatively, mutations can be introduced randomly along all or part of the coding sequence, such as by saturation mutagenesis, and the resultant mutants can be screened for biological activity to identify mutants that retain activity (e.g., the ability to bind a CXCL13 polypeptide, e.g., human, murine, or both human and murine CXCL13). Such variants (or derivatives thereof) of "human" or "fully human" antibodies can also be referred to as human or fully human antibodies that are "optimized" or "optimized for antigen binding" and include antibodies that have improved affinity to antigen.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al. (1988) Antibodies: A Laboratory Manual (2nd ed.; Cold Spring Harbor Laboratory Press).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention. All immunoglobulin classes are clearly within the scope of the present invention, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda ($\kappa$, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B-cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL or VK) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated herein, the variable region allows the antibody to selectively recognize and specifically bind epitopes on antigens. That is, the VL domain and VH domain, or subset of the complementarity determining regions (CDRs) within these variable domains, of an antibody combine to form the variable region that defines a three-dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three-dimensional configuration in an aqueous environment. The remainder of the amino acids in the antigen binding domains, referred to as "framework" regions, show less inter-molecular variability. The framework regions largely adopt a $\beta$-sheet conformation and the CDRs form loops that connect, and in some cases form part of, the $\beta$-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see below).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk, J. Mol. Biol. 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in Table 1 as a comparison. The exact residue numbers that encompass a particular CDR will vary depending on the sequence and size of the CDR. Those skilled in the art can routinely determine which residues comprise a particular CDR given the variable region amino acid sequence of the antibody.

TABLE 1

| CDR Definitions[1] | | |
|---|---|---|
| | Kabat | Chothia |
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an anti-CXCL13 antibody or antigen-binding fragment, variant, or derivative thereof of the present invention are according to the Kabat numbering system.

Antibodies or antigen-binding fragments, variants, or derivatives thereof of the invention include, but are not limited to, polyclonal, monoclonal, multispecific, human, humanized, primatized, or chimeric antibodies, single-chain antibodies, epitope-binding fragments, e.g., Fab, Fab' and F(ab')2, Fd, Fvs, single-chain Fvs (scFv), disulfide-linked Fvs (sdFv), fragments comprising either a VL or VH domain, fragments produced by a Fab expression library, and anti-idiotypic (anti-Id) antibodies (including, e.g., anti-Id antibodies to anti-CXCL13 antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1, and IgA2, etc.), or subclass of immunoglobulin molecule.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. For example, a binding polypeptide for use in the invention may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the invention comprises a polypeptide chain comprising a CH3 domain. Further, a binding polypeptide for use in the invention may lack at least a portion of a CH2 domain (e.g., all or part of a CH2 domain). As set forth above, it will be understood by one of ordinary skill in the art that these domains (e.g., the heavy chain portions) may be modified such that they vary in amino acid sequence from the naturally occurring immunoglobulin molecule.

In certain anti-CXCL13 antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody.

The heavy chain portions of a binding molecule for use in the diagnostic and treatment methods disclosed herein may be derived from different immunoglobulin molecules. For example, a heavy chain portion of a polypeptide may comprise a $C_{H1}$ domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain, e.g., a kappa or lambda light chain. Preferably, the light chain portion comprises at least one of a VL or CL domain.

Anti-CXCL13 antibodies, or antigen-binding fragments, variants, or derivatives thereof disclosed herein may be described or specified in terms of the epitope(s) or portion(s) of an antigen, e.g., a target polypeptide disclosed herein (e.g., CXCL13) that they recognize or specifically bind. The portion of a target polypeptide that specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or may include non-polypeptide elements, e.g., an epitope may include a carbohydrate side chain.

The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. A peptide or polypeptide epitope recognized by anti-CXCL13 antibodies of the present invention may contain a sequence of at least 4, at least 5, at least 6, at least 7, more preferably at least 8, at least 9, at least 10, at least 15, at least 20, at least 25, or between about 15 to about 30 contiguous or non-contiguous amino acids of CXCL13.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an $K_D$ that is at least one order of magnitude less than the antibody's $K_D$ for the second epitope. In another non-limiting example, an antibody may be considered to bind a first epitope preferentially if it binds the first epitope with an $K_D$ that is at least two orders of magnitude less than the antibody's $K_D$ for the second epitope.

In another non-limiting example, an antibody may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an k(off) that is at least one order of magnitude less than the antibody's k(off) for the second epitope. In another non-limiting example, an antibody may be considered to bind a first epitope preferentially if it binds the first epitope with an k(off) that is at least two orders of magnitude less than the antibody's k(off) for the second epitope. An antibody or antigen-binding fragment, variant, or derivative disclosed herein may be said to bind a target polypeptide disclosed herein (e.g., CXCL13, e.g., human, murine, or both human and murine CXCL13) or a fragment or variant thereof with an off rate (k(off)) of less than or equal to $5 \times 10^{-2}$ sec$^{-1}$, $10^{-2}$ sec$^{-1}$, or $5 \times 10^{-3}$ sec$^{-1}$. In certain embodiments, the k(off) is less than or equal to about $3 \times 10^{-2}$, e.g., wherein the antibody is 3D2 and the CXCL13 is human or mouse. In another embodiment, the k(off) is less than or equal to about $3 \times 10^{-3}$, e.g., wherein the antibody is MAb 5261 and the CXCL13 is human or mouse. In another embodiment, the k(off) is less than or equal to about $4 \times 10^{-3}$, e.g., wherein the antibody is MAb 5378 and the CXCL13 is human or mouse. In one embodiment, an antibody of the invention may be said to bind a target polypeptide disclosed herein (e.g., CXCL13, e.g., human, murine, or both human and murine CXCL13) or a fragment or variant thereof with an off rate (k(off)) less than or equal to $5 \times 10^{-4}$ sec$^{-1}$, $10^{-4}$ sec$^{-1}$, $5 \times 10^{-5}$ sec$^{-1}$, or $10^{-5}$ sec$^{-1}$, $5 \times 10^{-6}$ sec$^{-1}$, $10^{-6}$ sec$^{-1}$, $5 \times 10^{-7}$ sec$^{-1}$ or $10^{-7}$ sec$^{-1}$.

An antibody or antigen-binding fragment, variant, or derivative disclosed herein may be said to bind a target polypeptide disclosed herein (e.g., CXCL13, e.g., human, murine, or both human and murine CXCL13) or a fragment or variant thereof with an on rate (k(on)) of greater than or equal to $10^3$ M$^{-1}$ sec$^{-1}$, $5 \times 10^3$ M$^{-1}$ sec$^{-1}$, $10^4$ M$^{-1}$ sec$^{-1}$, $5 \times 10^4$ M$^{-1}$ sec$^{-1}$, $10^5$ M$^{-1}$ sec$^{-1}$, $5 \times 10^5$ M$^{-1}$ sec$^{-1}$, $10^6$ M$^{-1}$ sec$^{-1}$ or $5 \times 10^6$ M$^{-1}$ sec$^{-1}$. In certain embodiments, the k(on) is greater than or equal to about $5 \times 10^5$, e.g., wherein the antibody is 3D2 and the CXCL13 is human; or the the k(on) is greater than or equal to about $1 \times 10^5$, e.g., wherein the antibody is 3D2 and the CXCL13 is mouse. In another embodiment, the k(on) is greater than or equal to about $1 \times 10^6$, e.g., wherein the antibody is MAb 5261 and the CXCL13 is human or mouse. In another embodiment, the k(on) is greater than or equal to about $1 \times 10^6$, e.g., wherein the antibody is MAb 5378 and the CXCL13 is human or mouse. In one embodiment, an antibody of the invention may be said to bind a target polypeptide disclosed herein (e.g., CXCL13, e.g., human, murine, or both human and murine CXCL13) or a fragment or variant thereof with an on rate (k(on)) greater than or equal to $10^5$ M$^{-1}$ sec$^{-1}$, $5 \times 10^5$ M$^{-1}$ sec$^{-1}$, $10^6$ M$^{-1}$ sec$^{-1}$, or $5 \times 10^6$ M$^{-1}$ sec$^{-1}$ or $10^7$ M$^{-1}$ sec$^{-1}$.

An antibody is said to competitively inhibit binding of a reference antibody, e.g., an anti-CXCL3 antibody disclosed herein, e.g., MAb 5261, MAb 5378, MAb 5080, MAb 1476, 3D2, or 3C9, to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al. (1988) Antibodies: A Laboratory Manual (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-CXCL13 antibodies or antigen-binding fragments, variants, or derivatives thereof of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross-reactive epitope generally contains many of the same complementary structural features as the inducing epitope, and in some cases, may actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody may be deemed "highly specific" for a certain epitope, if it does not bind any other analog, ortholog, or homolog of that epitope.

Anti-CXCL13 binding molecules, e.g., antibodies or antigen-binding fragments, variants or derivatives thereof, of the invention may also be described or specified in terms of their binding affinity to a polypeptide of the invention, e.g., CXCL13, e.g., human, murine, or both human and murine CXCL13. In certain embodiments, the binding affinities of the invention include those with a dissociation constant or Kd less than or no greater than $5\times10^{-2}$ M, $10^{-2}$ M, $5\times10^{-3}$ M, $10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M. In one embodiment, the anti-CXCL13 binding molecule, e.g., an antibody or antigen binding fragment thereof, of the invention binds human CXCL13 with a Kd of less than about $5\times10^{-9}$ M to about $5\times10^{-10}$ M, e.g., wherein the antibody is MAb 5261 and the Kd is less than or equal to about $5\times10^{-9}$ M. In another embodiment, the anti-CXCL13 binding molecule, e.g., an antibody or antigen binding fragment thereof, of the invention binds murine CXCL13 with a Kd of less than about $5\times10^{-7}$ M to about $9\times10^{-9}$ M, e.g., wherein the antibody is MAb 5261 and the Kd is less than or equal to about $8\times10^{-9}$ M.

Anti-CXCL13 antibodies or antigen-binding fragments, variants or derivatives thereof of the invention may be "multispecific," e.g., bispecific, trispecific, or of greater multispecificity, meaning that it recognizes and binds to two or more different epitopes present on one or more different antigens (e.g., proteins) at the same time. Thus, whether an anti-CXCL13 antibody is "monospecific" or "multispecific, " e.g., "bispecific," refers to the number of different epitopes with which a binding polypeptide reacts. Multispecific antibodies may be specific for different epitopes of a target polypeptide described herein or may be specific for a target polypeptide as well as for a heterologous epitope, such as a heterologous polypeptide or solid support material.

As used herein the term "valency" refers to the number of potential binding domains, e.g., antigen binding domains present in a binding polypeptide or CXCL13 binding molecule, e.g., an antibody or antigen binding fragment thereof. Each binding domain specifically binds one epitope. When a binding polypeptide or CXCL13 binding molecule comprises more than one binding domain, each binding domain may specifically bind the same epitope, for an antibody with two binding domains, termed "bivalent monospecific," or to different epitopes, for an antibody with two binding domains, termed "bivalent bispecific." An antibody or antigen binding fragment thereof may also be bispecific and bivalent for each specificity (termed "bispecific tetravalent antibodies"). In another embodiment, tetravalent minibodies or domain deleted antibodies can be made.

Bispecific bivalent antibodies, and methods of making them, are described, for instance in U.S. Pat. Nos. 5,731, 168; 5,807,706; 5,821,333; and U.S. Patent Appl. Publ. Nos. 2003/020734 and 2002/0155537, the disclosures of all of which are incorporated by reference herein. Bispecific tetravalent antibodies, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tuft et al., J. Immunol. 147:60-69 (1991); U.S. Pat. Nos. 4,474,893; 4,714,681; 4,925,648; 5,573,920; 5,601,819; Kostelny et al., J. Immunol. 148: 1547-1553 (1992).

As previously indicated, the subunit structures and three-dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat E A et al.). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al., J. Immunol. 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CL regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant invention) is obtained from a second species. In certain embodiments the target binding region or site will be from a non-human source (e.g., mouse or primate) and the constant region is human (for example, monoclonal antibody (MAb) 1476 described herein).

As used herein, the term "engineered antibody" refers to an antibody in which the variable domain in either the heavy or light chain or both is altered by at least partial replacement of one or more CDRs from an antibody of known specificity and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable domain to transfer the antigen binding capacity of one variable domain to another. Rather, it may only be necessary to transfer those residues that are necessary to maintain the activity of the target binding site. In certain embodiments, the humanized antibody comprises 1, 2, or 3 CDRs from a donor variable heavy domain. In another embodiment, the humanized antibody comprises 1, 2, or 3 CDRs from a donor variable light domain.

It is further recognized that the framework regions within the variable domain in a heavy or light chain, or both, of a humanized antibody may comprise solely residues of human origin, in which case these framework regions of the humanized antibody (for example, MAb 5080 or 5261) are referred to as "fully human framework regions." Alternatively, one or more residues of the framework region(s) of the donor variable domain can be engineered within the corresponding position of the human framework region(s) of a variable domain in a heavy or light chain, or both, of a humanized antibody if necessary to maintain proper binding or to enhance binding to the CXCL13 antigen. A human framework region that has been engineered in this manner would thus comprise a mixture of human and donor framework residues and is referred to herein as a "partially human framework region."

For example, humanization of an anti-CXCL13 antibody can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent or mutant rodent CDRs or CDR sequences for the corresponding sequences of a human anti-CXCL13 antibody. See also U.S. Pat. Nos. 5,225,539; 5,585,089; 5,693,761; 5,693,762; and 5,859,205; herein incorporated by reference. The resulting humanized anti-CXCL13 antibody would comprise at least one rodent or mutant rodent CDR within the fully human framework regions of the variable domain of the heavy and/or light chain of the humanized antibody. In some instances, residues within the framework regions of one or more variable domains of the humanized anti-CXCL13 antibody are replaced by corresponding non-human (for example, rodent) residues (see, for example, U.S. Pat. Nos. 5,585,089; 5,693,761; 5,693,762; and 6,180,370), in which case the resulting humanized anti-CXCL13 antibody would comprise partially human framework regions within the variable domain of the heavy and/or light chain.

Furthermore, humanized antibodies may comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., Nature 331:522-525 (1986); Riechmann et al., Nature 332:323-329 (1988); and Presta, Curr. Op. Struct. Biol. 2:593-596 (1992); herein incorporated by reference. Accordingly, such "humanized" antibodies may include antibodies wherein substantially less than an intact human variable domain has been substituted by the corresponding sequence from a non-human species. In practice, humanized antibodies are typically human antibodies in which some or all CDR residues and possibly some framework residues are substituted by residues from analogous sites in rodent antibodies. See, for example, U.S. Pat. Nos. 5,225,539; 5,585,089; 5,693,761; 5,693,762; and 5,859,205. See also U.S. Pat. No. 6,180,370, and International Publication No. WO 01/27160, where humanized antibodies and techniques for producing humanized antibodies having improved affinity for a predetermined antigen are disclosed.

As used herein, the terms "linked," "fused," or "fusion" are used interchangeably. These terms refer to the joining together of two more elements or components, by whatever means including chemical conjugation or recombinant means. An "in-frame fusion" refers to the joining of two or more polynucleotide open reading frames (ORFs) to form a continuous longer ORF, in a manner that maintains the correct translational reading frame of the original ORFs. Thus, a recombinant fusion protein is a single protein containing two or more segments that correspond to polypeptides encoded by the original ORFs (which segments are not normally so joined in nature). Although the reading frame is thus made continuous throughout the fused segments, the segments may be physically or spatially separated by, for example, in-frame linker sequence. For example, polynucleotides encoding the CDRs of an immunoglobulin variable region may be fused, in-frame, but be separated by a polynucleotide encoding at least one immunoglobulin framework region or additional CDR regions, as long as the "fused" CDRs are co-translated as part of a continuous polypeptide.

In the context of polypeptides, a "linear sequence" or a "sequence" is an order of amino acids in a polypeptide in an amino to carboxyl terminal direction in which residues that neighbor each other in the sequence are contiguous in the primary structure of the polypeptide.

The term "expression" as used herein refers to a process by which a gene produces a biochemical, for example, a polypeptide. The process includes any manifestation of the functional presence of the gene within the cell including, without limitation, gene knockdown as well as both transient expression and stable expression. It includes without limitation transcription of the gene into messenger RNA (mRNA), and the translation of such mRNA into polypeptide(s). If the final desired product is a biochemical, expression includes the creation of that biochemical and any precursors. Expression of a gene produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

As used herein, the terms "treat" or "treatment" refer to both therapeutic treatment and prophylactic or preventative measures, wherein the object is to prevent or slow down (lessen) an undesired physiological change or disorder, such as the progression of multiple sclerosis, lupus, arthritis, or cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cows, and so on.

As used herein, phrases such as "a subject that would benefit from administration of an anti-CXCL13 antibody" and "an animal in need of treatment" includes subjects, such as mammalian subjects, that would benefit from administration of an anti-CXCL13 antibody used, e.g., for detection of an anti-CXCL13 polypeptide (e.g., for a diagnostic procedure) and/or from treatment, i.e., palliation or prevention of a disease, with an anti-CXCL13 antibody. As described in more detail herein, an anti-CXCL13 antibody can be used in unconjugated form or can be conjugated, e.g., to a drug, prodrug, or an isotope.

Target Polypeptide Description

As used herein, the terms "CXCL13" and "CXCL13 polypeptide" are used interchangably. In certain embodiments, CXCL13 may include a full-sized CXCL13 or a fragment thereof, or a CXCL13 variant polypeptide, wherein the fragment of CXCL13 or CXCL13 variant polypeptide retains some or all functional properties of the full-sized CXCL13. The human CXCL13 polypeptide and polynucleotide sequences (SEQ ID NOs: 19 and 20, respectively) have been described, see, e.g., Legler, et. al., *J. Exp. Med.* 187(4):655-660 (1998). The mouse CXCL13 polypeptide and polynucleotide sequences (SEQ ID NOs: 21 and 22, respectively) have been described, see, e.g., Gunn, et. al., *Nature* 391(6669):799-803 (1998). Furthermore, the cynomolgus monkey CXCL13 polypeptide sequence has been described as shown in SEQ ID NO: 23.

Anti-CXCL13 Antibodies

Commercial antibodies that bind CXCL13 have been disclosed in the art, e.g., rat anti-mouse MAb 470 (R & D Systems) and mouse anti-human MAb 801 (R & D Systems). In addition, murine anti-CXCL13 antibodies are disclosed in U.S. Patent Application Publication No. 2008 0227704 A1.

The antibodies of the invention comprise anti-CXCL13 antibodies or antigen-binding fragments, variants, or derivatives thereof that bind to CXCL13, e.g., MAb 5261, MAb 5378, MAb 5080, MAb 1476, 3D2, or 3C9. In certain embodiments the anti-CXCL13 antibodies bind human, primate, murine, or both human and murine CXCL13. In certain embodiments, the anti-CXCL13 antibodies of the invention are humanized. In other embodiments, the anti-CXCL13 antibodies block CXCL13 binding to its receptor, e.g., CXCR5. In certain embodiments, the anti-CXCL13 antibodies of the invention are MAb 5261, MAb 5378, MAb 5080, MAb 1476, 3D2, 3C9, or antigen-binding fragments, variants, or derivatives thereof.

In one embodiment, the present invention provides an isolated binding molecule, e.g., an antibody or antigen binding fragments, variants, and derivatives thereof, which specifically binds to the same CXCL13 epitope as a reference antibody, e.g., MAb 5261, MAb 5378, MAb 5080, MAb 1476, 3D2, or 3C9. In another embodiment, the present invention provides an isolated binding molecule, e.g., an antibody or antigen binding fragment thereof, which specifically binds to CXCL13, and competitively inhibits a reference antibody, e.g., MAb 5261, MAb 5378, MAb 5080, MAb 1476, 3D2, or 3C9, from specifically binding to CXCL13, e.g., human, primate, murine, or both human and murine CXCL13.

In certain embodiments, the binding molecule of the invention has an amino acid sequence that has at least about 80%, about 85%, about 88%, about 89%, about 90%, about 91%, about 92%, about 93%, about 94%, or about 95% sequence identity of an amino acid sequence for the reference anti-CXCL13 antibody molecule. In a further embodiment, the binding molecule shares at least about 96%, about 97%, about 98%, about 99%, or 100% sequence identity to a reference antibody. In certain embodiments, the reference antibody is MAb 5261, MAb 5378, MAb 5080, MAb 1476, 3D2, or 3C9.

In another embodiment, the present invention provides an isolated antibody or antigen-binding fragment thereof comprising, consisting essentially of, or consisting of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to CDR1, CDR2 or CDR3 of SEQ ID NO: 3 or 13.

In another embodiment, the present invention provides an isolated antibody or antigen-binding fragment thereof comprising, consisting essentially of, or consisting of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to SEQ ID NO: 4, 5, or 6.

In another embodiment, the present invention provides an isolated antibody or antigen-binding fragment thereof comprising, consisting essentially of, or consisting of an immunoglobulin heavy chain variable domain (VH domain), where the VH domain has an amino acid sequence that is at least about 80%, about 85%, about 90%, about 95%, about 96%, about 97%, about 98%, about 99%, or identical to SEQ ID NO: 3 or 13.

In another embodiment, the present invention provides an isolated antibody or antigen-binding fragment thereof comprising, consisting essentially of, or consisting of an immunoglobulin heavy chain variable domain (VH domain), where at least one of the CDRs of the VH domain has an amino acid sequence identical, except for 1, 2, 3, 4, or 5 conservative amino acid substitutions, to CDR1, CDR2 or CDR3 of SEQ ID NO: 3 or 13.

In another embodiment, the present invention provides an isolated antibody or antigen-binding fragment thereof comprising, consisting essentially of, or consisting of an immunoglobulin heavy chain variable domain (VH domain), where at least one of the CDRs of the VH domain has an amino acid sequence identical, except for 1, 2, 3, 4, or 5 conservative amino acid substitutions, to SEQ ID NO: 4, 5, or 6.

In another embodiment, the present invention provides an isolated antibody or antigen-binding fragment thereof comprising, consisting essentially of, or consisting of a VH domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 3 or 13, wherein an anti-CXCL13 antibody comprising the encoded VH domain specifically or preferentially binds to CXCL13.

In another embodiment, the present invention provides an isolated antibody or antigen-binding fragment thereof comprising, consisting essentially of, or consisting of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to CDR1, CDR2 or CDR3 of SEQ ID NO: 8, 15, or 17.

In another embodiment, the present invention provides an isolated antibody or antigen-binding fragment thereof comprising, consisting essentially of, or consisting of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to SEQ ID NO: 9, 16, 10, or 11.

In another embodiment, the present invention provides an isolated antibody or antigen-binding fragment thereof comprising, consisting essentially of, or consisting of an immunoglobulin light chain variable domain (VL domain), where the VL domain has an amino acid sequence that is at least about 80%, about 85%, about 90%, about 95%, about 96%, about 97%, about 98%, about 99%, or identical to SEQ ID NO: 8, 15, or 17.

In another embodiment, the present invention provides an isolated antibody or antigen-binding fragment thereof comprising, consisting essentially of, or consisting of an immunoglobulin light chain variable domain (VL domain), where at least one of the CDRs of the VL domain has an amino acid sequence identical, except for 1, 2, 3, 4, or 5 conservative amino acid substitutions, to CDR1, CDR2 or CDR3 of SEQ ID NO: 8, 15, or 17.

In another embodiment, the present invention provides an isolated antibody or antigen-binding fragment thereof comprising, consisting essentially of, or consisting of an immunoglobulin light chain variable domain (VL domain), where at least one of the CDRs of the VL domain has an amino acid sequence identical, except for 1, 2, 3, 4, or 5 conservative amino acid substitutions, to SEQ ID NO: 9, 16, 10, or 11.

In a further embodiment, the present invention includes an isolated antibody or antigen-binding fragment thereof comprising, consisting essentially of, or consisting of a VL domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 8, 15, or 17, wherein an anti-CXCL13 antibody comprising the encoded VL domain specifically or preferentially binds to CXCL13.

Suitable biologically active variants of the anti-CXCL13 antibodies of the invention can be used in the methods of the present invention. Such variants will retain the desired binding properties of the parent anti-CXCL13 antibody. Methods for making antibody variants are generally available in the art.

Methods for mutagenesis and nucleotide sequence alterations are well known in the art. See, for example, Walker and Gaastra, eds. (1983) Techniques in Molecular Biology (MacMillan Publishing Company, New York); Kunkel, *Proc. Natl. Acad. Sci. USA* 82:488-492 (1985); Kunkel et al., *Methods Enzymol.* 154:367-382 (1987); Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in Atlas of Protein Sequence and Structure (Natl. Biomed. Res. Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. Conservative substitutions, such as exchanging one amino acid with another having similar properties, may be preferred. Examples of conservative amino acid substitutions as taught by the PAM 250 matrix of the Dayhoff et al. model include, but are not limited to, Gly↔Ala, Val↔Ile↔Leu, Asp↔Glu, Lys↔Arg, Asn↔Gln, and Phe↔Trp↔Tyr.

In constructing variants of the anti-CXCL13 binding molecule, e.g., an antibody or antigen-binding fragment thereof, polypeptides of interest, modifications are made such that variants continue to possess the desired properties, e.g., being capable of specifically binding to a CXCL13, e.g., human, primate, murine, or both human and murine CXCL13. Obviously, any mutations made in the DNA encoding the variant polypeptide must not place the sequence out of reading frame and preferably will not create complementary regions that could produce secondary mRNA structure. See, e.g., EP Pat. No. EP0075444 B1.

Methods for measuring anti-CXCL13 binding molecule, e.g., an antibody or antigen-binding fragment thereof, binding specificity include, but are not limited to, standard competitive binding assays, assays for monitoring immunoglobulin secretion by T cells or B cells, T cell proliferation assays, apoptosis assays, ELISA assays, and the like. See, for example, such assays disclosed in WO 93/14125; Shi et al., *Immunity* 13:633-642 (2000); Kumanogoh et al., *J Immunol* 169:1175-1181 (2002); Watanabe et al., *J Immunol* 167:4321-4328 (2001); Wang et al., *Blood* 97:3498-3504 (2001); and Giraudon et al., *J Immunol* 172(2):1246-1255 (2004), all of which are herein incorporated by reference.

When discussed herein whether any particular polypeptide, including the constant regions, CDRs, VH domains, or VL domains disclosed herein, is at least about 65%, about 70%, about 75%, about 80%, about 85%, about 90%, about 91%, about 92%, about 93%, about 94%, about 95%, about 96%, about 97%, about 98%, about 99%, or even about 100% identical to another polypeptide, the % identity can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) Adv. Appl. Math. 2:482-489, to find the best segment of homology between two sequences. When using BESTFIT or any other sequence alignment program to determine whether a particular sequence is, for example, 95% identical to a reference sequence according to the present invention, the parameters are set, of course, such that the percentage of identity is calculated over the full length of the reference polypeptide sequence and that gaps in homology of up to 5% of the total number of amino acids in the reference sequence are allowed.

For purposes of the present invention, percent sequence identity may be determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) Adv. Appl. Math. 2:482-489. A variant may, for example, differ from a reference anti-CXCL13 antibody (e.g., MAb 5261, MAb 5378, MAb 5080, MAb 1476, 3D2, or 3C9) by as few as 1 to 15 amino acid residues, as few as 1 to 10 amino acid residues, such as 6-10, as few as 5, as few as 4, 3, 2, or even 1 amino acid residue.

The precise chemical structure of a polypeptide capable of specifically binding CXCL13 and retaining the desired CXCL13 blocking activity depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of anti-CXCL13 antibodies as used herein. Further, the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of an anti-CXCL13 antibody used herein so long as the desired properties of the anti-CXCL13 antibody are not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy the desired properties (e.g., binding specificity for CXCL13, binding affinity, and/or CXCL13 blocking activity) do not remove the polypeptide sequence from the definition of anti-CXCL13 antibodies of interest as used herein.

The art provides substantial guidance regarding the preparation and use of polypeptide variants. In preparing the anti-CXCL13 binding molecule, e.g., an antibody or antigen-binding fragment thereof, variants, one of skill in the art can readily determine which modifications to the native protein's nucleotide or amino acid sequence will result in a variant that is suitable for use as a therapeutically active component of a pharmaceutical composition used in the methods of the present invention.

The constant region of an anti-CXCL13 antibody may be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

In certain anti-CXCL13 antibodies, the Fc portion may be mutated to decrease effector function using techniques known in the art. For example, the deletion or inactivation (through point mutations or other means) of a constant region domain may reduce Fc receptor binding of the circulating modified antibody thereby increasing tumor localization. In other cases it may be that constant region modifications consistent with the instant invention moderate complement binding and thus reduce the serum half life and nonspecific association of a conjugated cytotoxin. Yet other modifications of the constant region may be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, may easily be measured and quantified using well known immunological techniques without undue experimentation.

Anti-CXCL13 antibodies of the invention also include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., binding specificity for CXCL13, binding affinity, and/or CXCL13 blocking activity).

For example, it is possible to introduce mutations only in framework regions or only in CDR regions of an antibody molecule. Introduced mutations may be silent or neutral missense mutations, i.e., have no, or little, effect on an antibody's ability to bind antigen. These types of mutations may be useful to optimize codon usage, or improve a hybridoma's antibody production. Alternatively, non-neutral missense mutations may alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein may routinely be expressed and the functional and/or biological activity of the encoded protein, (e.g., ability to immunospecifically bind at least one epitope of a CXCL13 polypeptide) can be determined using techniques described herein or by routinely modifying techniques known in the art.

In certain embodiments, the anti-CXCL13 antibodies of the invention comprise at least one optimized complementarity-determining region (CDR). By "optimized CDR" is intended that the CDR has been modified and optimized sequences selected based on the sustained or improved binding affinity and/or anti-CXCL13 activity that is imparted to an anti-CXCL13 antibody comprising the optimized CDR. "Anti-CXCL13 activity" or "CXCL13 blocking activity" can include activity which modulates one or more of the following activities associated with CXCL13: blockade of CXCL13 interaction with its receptor resulting in interference with B cell and follicular B-helper T cell migration into inflamed tissues and germinal center formation (e.g., in the case of autoimmune diseases); inhibition of cancer cell proliferation and ability to spread in oncological disorders; or any other activity association with CXCL13-expressing cells. Anti-CXCL13 activity can also be attributed to a decrease in incidence or severity of diseases associated with CXCL13 expression, including, but not limited to, certain types of autoimmune diseases (e.g., Multiple sclerosis, arthritis (e.g., Rheumatoid arthritis), chronic gastritis, gastric lymphomas, transplant rejection, Sjogren syndrome (SS), Systemic Lupus Erythematosis (SLE), active mixed cryoglobulinemia (MC) vasculitis in Hepatitis C virus infection, Juvenile dermatomyositis, and Myastenia Gravis) and certain cancers (e.g., Burkitt's lymphoma, Non-Hodgkin Lymphoma, MALT lymphoma (e.g., gastric MALT lymphoma), Carcinoma (e.g., colon, prostate, breast, stomach, esophageal, and pancreatic), and Chronic lymphocytic leukemia (CLL)) as well as other inflammatory diseases such as *Helicobacter* infection induced inflammatory diseases, e.g., gastritis, ulcers, and gastric mucosal lesions.

Polynucleotides Encoding Anti-CXCL13 Antibodies

The present invention also provides for nucleic acid molecules encoding anti-CXCL13 antibodies of the invention, or antigen-binding fragments, variants, or derivatives thereof.

In one embodiment, the present invention provides an isolated polynucleotide comprising, consisting essentially of, or consisting of a nucleic acid encoding an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to a polynucleotide sequence selected from CDR1, CDR2 or CDR3 of SEQ ID NO: 2 or 12.

In other embodiments, the present invention provides an isolated polynucleotide comprising, consisting essentially of, or consisting of a nucleic acid encoding an immunoglobulin VH domain, where at least one of the CDRs of the VH domain is selected from the group consisting of: (a) a CDR1 comprising the amino acid sequence set forth in SEQ ID NO: 4; (b) a CDR2 comprising the amino acid sequence set forth in SEQ ID NO: 5; and (c) a CDR3 comprising the amino acid sequence set forth in SEQ ID NO: 6.

In a further embodiment, the present invention includes an isolated polynucleotide comprising, consisting essentially of, or consisting of a nucleic acid encoding a VH domain that has an amino acid sequence that is at least about 80%, about 85%, about 90%, about 91%, about 92%, about 93%, about 94%, about 95%, about 96%, about 97%, about 98%, about 99%, or 100% identical to a reference VH domain polypeptide sequence comprising SEQ ID NO: 3 or SEQ ID NO: 13, wherein an anti-CXCL13 antibody comprising the encoded VH domain specifically or preferentially binds to CXCL13.

In a further embodiment, the present invention includes an isolated polynucleotide comprising, consisting essentially of, or consisting of a nucleic acid encoding a VH domain, wherein the polynucleotide sequence is at least about 80%, about 85%, about 90%, about 91%, about 92%, about 93%, about 94%, about 95%, about 96%, about 97%, about 98%, about 99%, or 100% identical to a sequence comprising SEQ ID NO: 2 or SEQ ID NO: 12, wherein an anti-CXCL13 antibody comprising the encoded VH domain specifically or preferentially binds to CXCL13.

In one embodiment, the present invention provides an isolated polynucleotide comprising, consisting essentially of, or consisting of a nucleic acid encoding an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to a polynucleotide sequence of CDR1, CDR2 or CDR3 of SEQ ID NO: 8, SEQ ID NO: 15, or SEQ ID NO: 17.

In other embodiments, the present invention provides an isolated polynucleotide comprising, consisting essentially of, or consisting of a nucleic acid encoding an immunoglobulin VL domain, where at least one of the CDRs of the VL domain is selected from the group consisting of: (a) a CDR1 comprising the amino acid sequence set forth in SEQ ID NO: 9 or 16; (b) a CDR2 comprising the amino acid sequence set forth in SEQ ID NO: 10; and (c) a CDR3 comprising the amino acid sequence set forth in SEQ ID NO: 11.

In a further embodiment, the present invention includes an isolated polynucleotide comprising, consisting essentially of, or consisting of a nucleic acid encoding a VL domain that has an amino acid sequence that is at least about 80%, about 85%, about 90%, about 91%, about 92%, about 93%, about 94%, about 95%, about 96%, about 97%, about 98%, about 99%, or 100% identical to a reference VL domain polypeptide sequence comprising SEQ ID NO: 8, 15, or 17, wherein an anti-CXCL13 antibody comprising the encoded VL domain specifically or preferentially binds to CXCL13.

In a further embodiment, the present invention includes an isolated polynucleotide comprising, consisting essentially of, or consisting of a nucleic acid encoding a VL domain, wherein the polynucleotide sequence is at least about 80%, about 85%, about 90%, about 91%, about 92%, about 93%, about 94%, about 95%, about 96%, about 97%, about 98%, about 99%, or 100% identical to a sequence comprising SEQ ID NO: 7, SEQ ID NO: 14, or SEQ ID NO: 18, wherein an anti-CXCL13 antibody comprising the encoded VL domain specifically or preferentially binds to CXCL13.

Any of the polynucleotides described above may further include additional nucleic acids, encoding, e.g., a signal peptide to direct secretion of the encoded polypeptide, antibody constant regions as described herein, or other heterologous polypeptides as described herein. Also, as described in more detail elsewhere herein, the present invention includes compositions comprising one or more of the polynucleotides described above.

In one embodiment, the invention includes compositions comprising a first polynucleotide and second polynucleotide wherein said first polynucleotide encodes a VH domain as described herein and wherein said second polynucleotide encodes a VL domain as described herein. Specifically, a composition which comprises, consists essentially of, or consists of a VH domain-encoding polynucleotide, as set forth in SEQ ID NO: 2 or 12, and a VL domain-encoding polynucleotide, for example, a polynucleotide encoding the VL domain as set forth in SEQ ID NO: 7, 14, or 18.

The present invention also includes fragments of the polynucleotides of the invention, as described elsewhere. Additionally, polynucleotides that encode fusion polypolypeptides, Fab fragments, and other derivatives, as described herein, are also contemplated by the invention.

The polynucleotides may be produced or manufactured by any method known in the art. For example, if the nucleotide sequence of the antibody is known, a polynucleotide encoding the antibody may be assembled from chemically synthesized oligonucleotides (e.g., as described in Kutmeier et al., *Bio Techniques* 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an anti-CXCL13 antibody, or antigen-binding fragment, variant, or derivative thereof of the invention, may be generated from nucleic acid from a suitable source. If a clone containing a nucleic acid encoding a particular antibody is not available, but the sequence of the antibody molecule is known, a nucleic acid encoding the antibody may be chemically synthesized or obtained from a suitable source (e.g., an antibody cDNA library, or a cDNA library generated from, or nucleic acid, preferably poly A+RNA, isolated from, any tissue or cells expressing the antibody or other anti-CXCL13 antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody or other anti-CXCL13 antibody. Amplified nucleic acids generated by PCR may then be cloned into replicable cloning vectors using any method well known in the art.

Once the nucleotide sequence and corresponding amino acid sequence of the anti-CXCL13 antibody, or antigen-binding fragment, variant, or derivative thereof is determined, its nucleotide sequence may be manipulated using methods well known in the art for the manipulation of nucleotide sequences, e.g., recombinant DNA techniques, site directed mutagenesis, PCR, etc. (see, for example, the techniques described in Sambrook et al. (1990) Molecular Cloning, A Laboratory Manual (2nd ed.; Cold Spring Harbor Laboratory, Cold Spring Harbor, N.Y.) and Ausubel et al., eds. (1998) Current Protocols in Molecular Biology (John Wiley & Sons, NY), which are both incorporated by reference herein in their entireties), to generate antibodies having a different amino acid sequence, for example to create amino acid substitutions, deletions, and/or insertions.

A polynucleotide encoding an anti-CXCL13 binding molecule, e.g., an antibody, or antigen-binding fragment, variant, or derivative thereof, can be composed of any polyribonucleotide or polydeoxyribonucleotide, which may be unmodified RNA or DNA or modified RNA or DNA. For example, a polynucleotide encoding anti-CXCL13 antibody, or antigen-binding fragment, variant, or derivative thereof can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, a polynucleotide encoding an anti-CXCL13 binding molecule, e.g., an antibody, or antigen-binding fragment, variant, or derivative thereof can be composed of triple-stranded regions comprising RNA or DNA or both RNA and DNA. A polynucleotide encoding an anti-CXCL13 binding molecule, e.g., antibody, or antigen-binding fragment, variant, or derivative thereof, may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

An isolated polynucleotide encoding a non-natural variant of a polypeptide derived from an immunoglobulin (e.g., an immunoglobulin heavy chain portion or light chain portion) can be created by introducing one or more nucleotide substitutions, additions or deletions into the nucleotide sequence of the immunoglobulin such that one or more amino acid substitutions, additions or deletions are introduced into the encoded protein. Mutations may be introduced by standard techniques, such as site-directed mutagenesis and PCR-mediated mutagenesis. Preferably, conservative amino acid substitutions are made at one or more non-essential amino acid residues.

Fusion Proteins and Antibody Conjugates

As discussed in more detail elsewhere herein, anti-CXCL13 binding molecules, e.g., antibodies of the invention, or antigen-binding fragments, variants, or derivatives thereof, may further be recombinantly fused to a heterologous polypeptide at the N- or C-terminus or chemically conjugated (including covalent and non-covalent conjugations) to polypeptides or other compositions. For example, anti-CXCL13 antibodies may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

Anti-CXCL13 antibodies of the invention, or antigen-binding fragments, variants, or derivatives thereof, may include derivatives that are modified, i.e., by the covalent attachment of any type of molecule to the antibody such that covalent attachment does not prevent the antibody binding anti-CXCL13. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the derivative may contain one or more non-classical amino acids.

Anti-CXCL13 binding molecules, e.g., antibodies of the invention, or antigen-binding fragments, variants, or derivatives thereof, can be composed of amino acids joined to each other by peptide bonds or modified peptide bonds, i.e., peptide isosteres, and may contain amino acids other than the 20 gene-encoded amino acids. For example, anti-CXCL13 antibodies may be modified by natural processes, such as posttranslational processing, or by chemical modification techniques that are well known in the art. Such modifications are well described in basic texts and in more detailed monographs, as well as in a voluminous research literature. Modifications can occur anywhere in the anti-CXCL13 binding molecule, including the peptide backbone, the amino acid side-chains and the amino or carboxyl termini, or on moieties such as carbohydrates. It will be appreciated that the same type of modification may be present in the same or varying degrees at several sites in a given anti-CXCL13 binding molecule. Also, a given anti-CXCL13 binding molecule may contain many types of modifications. Anti-CXCL13 binding molecules may be branched, for example, as a result of ubiquitination, and they may be cyclic, with or without branching. Cyclic, branched, and branched cyclic anti-CXCL13 binding molecule may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure and Molecular Properties, T. E. Creighton, W. H. Freeman and Company, NY; 2nd ed. (1993); Johnson, ed. (1983) Post-translational Covalent Modification of Proteins (Academic Press, NY), pgs. 1-12; Seifter et al., *Meth. Enzymol.* 182: 626-646 (1990); Rattan et al., *Ann. NY Acad Sci.* 663:48-62 (1992)).

The present invention also provides for fusion proteins comprising an anti-CXCL13 antibody, or antigen-binding fragment, variant, or derivative thereof, and a heterologous polypeptide. The heterologous polypeptide to which the antibody is fused may be useful for function or is useful to target the anti-CXCL13 polypeptide expressing cells.

In one embodiment, a fusion protein of the invention comprises, consists essentially of, or consists of, a polypeptide having the amino acid sequence of any one or more of the VH domains of an antibody of the invention or the amino acid sequence of any one or more of the VL domains of an antibody of the invention or fragments or variants thereof, and a heterologous polypeptide sequence.

In another embodiment, a fusion protein for use in the diagnostic and treatment methods disclosed herein comprises, consists essentially of, or consists of a polypeptide having the amino acid sequence of any one, two, three of the CDRs of the VH domain of an anti-CXCL13 antibody, or fragments, variants, or derivatives thereof, and/or the amino acid sequence of any one, two, three of the CDRs of the VL domain an anti-CXCL13 antibody, or fragments, variants, or derivatives thereof, and a heterologous polypeptide sequence. In one embodiment, a fusion protein comprises a polypeptide having the amino acid sequence of at least one VH domain of an anti-CXCL13 antibody of the invention and the amino acid sequence of at least one VL domain of an anti-CXCL13 antibody of the invention or fragments, derivatives or variants thereof, and a heterologous polypeptide sequence. Preferably, the VH and VL domains of the fusion protein correspond to a single source antibody (or scFv or Fab fragment) that specifically binds at least one epitope of CXCL13. In yet another embodiment, a fusion protein for use in the diagnostic and treatment methods disclosed herein comprises a polypeptide having the amino acid sequence of any one, two, three or more of the CDRs of the VH domain of an anti-CXCL13 antibody and the amino acid sequence of any one, two, three or more of the CDRs of the VL domain of an anti-CXCL13 antibody, or fragments or variants thereof, and a heterologous polypeptide sequence. Preferably, two, three, four, five, six, or more of the CDR(s) of the VH domain or VL domain correspond to single source antibody (or scFv or Fab fragment) of the invention. Nucleic acid molecules encoding these fusion proteins are also encompassed by the invention.

Exemplary fusion proteins reported in the literature include fusions of the T cell receptor (Gascoigne et al., *Proc. Natl. Acad. Sci. USA* 84:2936-2940 (1987)); CD4 (Capon et al., *Nature* 337:525-531 (1989); Traunecker et al., *Nature* 339:68-70 (1989); Zettmeissl et al., *DNA Cell Biol. USA* 9:347-353 (1990); and Byrn et al., *Nature* 344:667-670 (1990)); L-selectin (homing receptor) (Watson et al., *J. Cell. Biol.* 110:2221-2229 (1990); and Watson et al., *Nature* 349:164-167 (1991)); CD44 (Aruffo et al., *Cell* 61:1303-1313 (1990)); CD28 and B7 (Linsley et al., *J. Exp. Med.* 173:721-730 (1991)); CTLA-4 (Lisley et al., *J. Exp. Med.* 174:561-569 (1991)); CD22 (Stamenkovic et al., *Cell* 66:1133-1144 (1991)); TNF receptor (Ashkenazi et al., *Proc. Natl. Acad. Sci. USA* 88:10535-10539 (1991); Lesslauer et al., *Eur. J. Immunol.* 27:2883-2886 (1991); and Peppel et al., *J. Exp. Med.* 174:1483-1489 (1991)); and IgE receptor a (Ridgway and Gorman, *J. Cell. Biol.* Vol. 115, Abstract No. 1448 (1991)).

As discussed elsewhere herein, anti-CXCL13 binding molecules, e.g., antibodies of the invention, or antigen-binding fragments, variants, or derivatives thereof, may be fused to heterologous polypeptides to increase the in vivo half life of the polypeptides or for use in immunoassays using methods known in the art. For example, in one embodiment, PEG can be conjugated to the anti-CXCL13 antibodies of the invention to increase their half-life in vivo. See Leong et al., *Cytokine* 16:106 (2001); Adv. in Drug Deliv. Rev. 54:531 (2002); or Weir et al., *Biochem. Soc. Transactions* 30:512 (2002).

Moreover, anti-CXCL13 binding molecules, e.g., antibodies of the invention, or antigen-binding fragments, variants, or derivatives thereof, can be fused to marker sequences, such as a peptide to facilitate their purification or detection. In certain embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984)) and the "flag" tag.

Fusion proteins can be prepared using methods that are well known in the art (see for example U.S. Pat. Nos. 5,116,964 and 5,225,538). The precise site at which the fusion is made may be selected empirically to optimize the secretion or binding characteristics of the fusion protein. DNA encoding the fusion protein is then transfected into a host cell for expression.

Anti-CXCL13 binding molecules, e.g., antibodies of the present invention, or antigen-binding fragments, variants, or derivatives thereof, may be used in non-conjugated form or may be conjugated to at least one of a variety of molecules, e.g., to improve the therapeutic properties of the molecule, to facilitate target detection, or for imaging or therapy of the patient. Anti-CXCL13 binding molecules, e.g., antibodies of the invention, or antigen-binding fragments, variants, or derivatives thereof, can be labeled or conjugated either before or after purification, or when purification is performed.

In particular, anti-CXCL13 antibodies of the invention, or antigen-binding fragments, variants, or derivatives thereof, may be conjugated to therapeutic agents, prodrugs, peptides, proteins, enzymes, viruses, lipids, biological response modifiers, pharmaceutical agents, or PEG.

Those skilled in the art will appreciate that conjugates may also be assembled using a variety of techniques depending on the selected agent to be conjugated. For example, conjugates with biotin are prepared, e.g., by reacting a binding polypeptide with an activated ester of biotin such as the biotin N-hydroxysuccinimide ester. Similarly, conjugates with a fluorescent marker may be prepared in the presence of a coupling agent, e.g., those listed herein, or by reaction with an isothiocyanate, preferably fluorescein-isothiocyanate. Conjugates of the anti-CXCL13 antibodies of the invention, or antigen-binding fragments, variants, or derivatives thereof, are prepared in an analogous manner.

The present invention further encompasses anti-CXCL13 binding molecules, e.g., antibodies of the invention, or antigen-binding fragments, variants, or derivatives thereof, conjugated to a diagnostic or therapeutic agent. The anti-CXCL13 antibodies, including antigen-binding fragments, variants, and derivatives thereof, can be used diagnostically to, for example, monitor the development or progression of a disease as part of a clinical testing procedure to, e.g., determine the efficacy of a given treatment and/or prevention regimen. For example, detection can be facilitated by coupling the anti-CXCL13 antibody, or antigen-binding fragment, variant, or derivative thereof, to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In, $^{90}$Y, or $^{99}$Tc.

An anti-CXCL13 binding molecule, e.g., an antibody, or antigen-binding fragment, variant, or derivative thereof, may be conjugated to a therapeutic moiety such as a cytotoxin, a therapeutic agent or a radioactive metal ion. A cytotoxin or cytotoxic agent includes any agent that is detrimental to cells.

An anti-CXCL13 binding molecule, e.g., an antibody, or antigen-binding fragment, variant, or derivative thereof, also can be detectably labeled by coupling it to a chemiluminescent compound. The presence of the chemiluminescent-tagged anti-CXCL13 binding molecule is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

One of the ways in which an anti-CXCL13 antibody, or antigen-binding fragment, variant, or derivative thereof, can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md.; Diagnostic Horizons 2:1-7 (1978); Voller et al., *J. Clin. Pathol.* 31:507-520 (1978); Butler, *Meth. Enzymol.* 73:482-523 (1981); Maggio, ed. (1980) Enzyme Immunoassay, CRC Press, Boca Raton, Fla.; Ishikawa et al., eds. (1981) Enzyme Immunoassay (Kgaku Shoin, Tokyo). The enzyme, which is bound to the anti-CXCL13 antibody will react with an appropriate substrate, e.g., a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. Additionally, the detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the anti-CXCL13 binding molecule, e.g., antibody, or antigen-binding fragment, variant, or derivative thereof, it is possible to detect the binding molecule through the use of a radioimmunoassay (RIA) (see, for example, Weintraub (March, 1986) Principles of Radioimmunoassays, Seventh Training Course on Radioligand Assay Techniques (The Endocrine Society), which is incorporated by reference herein). The radioactive isotope can be detected by means including, but not limited to, a gamma counter, a scintillation counter, or autoradiography.

An anti-CXCL13 binding molecule, e.g., antibody, or antigen-binding fragment, variant, or derivative thereof, can also be detectably labeled using fluorescence emitting metals such as 152Eu, or others of the lanthanide series. These metals can be attached to the binding molecule using such metal chelating groups as diethylenetriaminepentacetic acid (DTPA) or ethylenediaminetetraacetic acid (EDTA).

Techniques for conjugating various moieties to an antibody, e.g., an anti-CXCL13 antibody or antigen-binding fragment, variant, or derivative thereof, are well known, see, e.g., Amon et al. (1985) "Monoclonal Antibodies for Immunotargeting of Drugs in Cancer Therapy," in Monoclonal Antibodies and Cancer Therapy, ed. Reisfeld et al. (Alan R. Liss, Inc.), pp. 243-56; Hellstrom et al. (1987) "Antibodies for Drug Delivery," in Controlled Drug Delivery, ed. Robinson et al. (2nd ed.; Marcel Dekker, Inc.), pp. 623-53); Thorpe (1985) "Antibody Carriers of Cytotoxic Agents in Cancer Therapy: A Review," in Monoclonal Antibodies '84: Biological and Clinical Applications, ed. Pinchera et al., pp. 475-506; "Analysis, Results, and Future Prospective of the Therapeutic Use of Radiolabeled Antibody in Cancer Therapy," in Monoclonal Antibodies for Cancer Detection and Therapy, ed. Baldwin et al., Academic Press, pp. 303-16 (1985); and Thorpe et al., *Immunol. Rev.* 62:119-58 (1982).

Expression of Antibody Polypeptides

DNA sequences that encode the light and the heavy chains of the antibody may be made, either simultaneously or separately, using reverse transcriptase and DNA polymerase in accordance with well known methods. PCR may be initiated by consensus constant region primers or by more specific primers based on the published heavy and light chain DNA and amino acid sequences. As discussed above, PCR also may be used to isolate DNA clones encoding the antibody light and heavy chains. In this case the libraries may be screened by consensus primers or larger homologous probes, such as mouse constant region probes.

DNA, typically plasmid DNA, may be isolated from the cells using techniques known in the art, restriction mapped and sequenced in accordance with standard, well known techniques set forth in detail, e.g., in the foregoing references relating to recombinant DNA techniques. Of course, the DNA may be synthetic according to the present invention at any point during the isolation process or subsequent analysis.

Following manipulation of the isolated genetic material to provide anti-CXCL13 antibodies, or antigen-binding fragments, variants, or derivatives thereof, of the invention, the polynucleotides encoding the anti-CXCL13 antibodies are typically inserted in an expression vector for introduction into host cells that may be used to produce the desired quantity of anti-CXCL13 antibody.

Recombinant expression of an antibody, or fragment, derivative or analog thereof, e.g., a heavy or light chain of an antibody that binds to a target molecule described herein, e.g., CXCL13, requires construction of an expression vector containing one or more polynucleotides that encode the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods that are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The term "vector" or "expression vector" is used herein to mean vectors used in accordance with the present invention as a vehicle for introducing into and expressing a desired gene in a host cell. As known to those skilled in the art, such vectors may easily be selected from the group consisting of plasmids, phages, viruses and retroviruses. In general, vectors compatible with the instant invention will comprise a selection marker, appropriate restriction sites to facilitate cloning of the desired gene and the ability to enter and/or replicate in eukaryotic or prokaryotic cells.

For the purposes of this invention, numerous expression vector systems may be employed. For example, one class of vector utilizes DNA elements that are derived from animal viruses such as bovine papilloma virus, polyoma virus, adenovirus, vaccinia virus, baculovirus, retroviruses (RSV, MMTV or MOMLV) or SV40 virus. Others involve the use of polycistronic systems with internal ribosome binding sites. Additionally, cells that have integrated the DNA into their chromosomes may be selected by introducing one or more markers which allow selection of transfected host cells. The marker may provide for prototrophy to an auxotrophic host, biocide resistance (e.g., antibiotics) or resistance to heavy metals such as copper. The selectable marker gene can either be directly linked to the DNA sequences to be expressed, or introduced into the same cell by cotransformation. Additional elements may also be needed for optimal synthesis of mRNA. These elements may include signal sequences, splice signals, as well as transcriptional promoters, enhancers, and termination signals.

In certain embodiments the cloned variable region genes are inserted into an expression vector along with the heavy and light chain constant region genes (e.g., human) synthesized as discussed above. Of course, any expression vector that is capable of eliciting expression in eukaryotic cells may be used in the present invention. Examples of suitable vectors include, but are not limited to plasmids pcDNA3, pHCMV/Zeo, pCR3.1, pEF 1/His, pIND/GS, pRc/HCMV2, pSV40/Zeo2, pTRACER-HCMV, pUB6N5-His, pVAX1, and pZeoSV2 (available from Invitrogen, San Diego, Calif.), and plasmid pCI (available from Promega, Madison, Wis.). In general, screening large numbers of transformed cells for those that express suitably high levels if immunoglobulin heavy and light chains is routine experimentation that can be carried out, for example, by robotic systems.

More generally, once the vector or DNA sequence encoding a monomeric subunit of the anti-CXCL13 antibody has been prepared, the expression vector may be introduced into an appropriate host cell. Introduction of the plasmid into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway (1988) "Mammalian Expression Vectors" in Vectors, ed. Rodriguez and Denhardt (Butterworths, Boston, Mass.), Chapter 24.2, pp. 470-472. Typically, plasmid introduction into the host is via electroporation. The host cells harboring the expression construct are grown under conditions appropriate to the production of the light chains and heavy chains, and are assayed for heavy and/or light chain protein synthesis. Exemplary assay techniques include enzyme-linked immunosorbent assay (ELISA), radioimmunoassay (RIA), or fluorescence-activated cell sorter analysis (FACS), immunohistochemistry and the like.

The expression vector is transferred to a host cell by conventional techniques, and the transfected cells are then cultured by conventional techniques to produce an antibody for use in the methods described herein. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

As used herein, "host cells" refers to cells that harbor vectors constructed using recombinant DNA techniques and encoding at least one heterologous gene. In descriptions of processes for isolation of antibodies from recombinant hosts, the terms "cell" and "cell culture" are used interchangeably to denote the source of antibody unless it is clearly specified otherwise. In other words, recovery of polypeptide from the "cells" may mean either from spun down whole cells, or from the cell culture containing both the medium and the suspended cells.

A variety of host-expression vector systems may be utilized to express antibody molecules for use in the methods described herein. Such host-expression systems represent vehicles by which the coding sequences of interest may be produced and subsequently purified, but also represent cells that may, when transformed or transfected with the appropriate nucleotide coding sequences, express an antibody molecule of the invention in situ. These include, but are not limited to, microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BLK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In certain embodiments, bacterial cells such as *Escherichia coli*, and in further embodiments, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

The host cell line used for protein expression is often of mammalian origin; those skilled in the art are credited with ability to preferentially determine particular host cell lines that are best suited for the desired gene product to be expressed therein. Exemplary host cell lines include, but are not limited to, CHO (Chinese Hamster Ovary), DG44 and DUXB11 (Chinese Hamster Ovary lines, DHFR minus), HELA (human cervical carcinoma), CVI (monkey kidney line), COS (a derivative of CVI with SV40 T antigen), VERY, BHK (baby hamster kidney), MDCK, 293, WI38, R1610 (Chinese hamster fibroblast) BALBC/3T3 (mouse fibroblast), HAK (hamster kidney line), SP2/O (mouse myeloma), P3.times.63-Ag3.653 (mouse myeloma), BFA-1c1BPT (bovine endothelial cells), RAJI (human lymphocyte) and 293 (human kidney). Host cell lines are typically available from commercial services, the American Tissue Culture Collection or from published literature.

In addition, a host cell strain may be chosen that modulates the expression of the inserted sequences or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used.

For long-term, high-yield production of recombinant proteins, stable expression is preferred. For example, cell lines that stably express the antibody molecule may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which stably express the antibody molecule.

A number of selection systems may be used, including, but not limited to, the herpes simplex virus thymidine kinase (Wigler et al., *Cell* 11:223 (1977)), hypoxanthine-guanine phosphoribosyltransferase (Szybalska and Szybalski, *Proc. Natl. Acad. Sci. USA* 48:202 (1992)), and adenine phosphoribosyltransferase (Lowy et al., *Cell* 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad. Sci. USA* 78:1527 (1981)); gpt, which confers resistance to mycophenolic acid (Mulligan and Berg, *Proc. Natl. Acad. Sci. USA* 78:2072 (1981)); neo, which confers resistance to the aminoglycoside G-418 Clinical Pharmacy 12:488-505; Wu and Wu, *Biotherapy* 3:87-95 (1991); Tolstoshev, *Ann. Rev. Pharmacol. Toxicol.* 32:573-596 (1993); Mulligan, *Science* 260: 926-932 (1993); and Morgan and Anderson, *Ann. Rev. Biochem.* 62:191-217 (1993); TIB TECH 11(5):155-215 (May 1993); and hygro, which confers resistance to hygromycin (Santerre et al., *Gene* 30:147 (1984). Methods commonly known in the art of recombinant DNA technology which can be used are described in Ausubel et al. (1993) Current Protocols in Molecular Biology (John Wiley & Sons, NY); Kriegler (1990) "Gene Transfer and Expression" in A Laboratory Manual (Stockton Press, NY); Dracopoli et al. (eds) (1994) Current Protocols in Human Genetics (John Wiley & Sons, NY) Chapters 12 and 13; Colberre-Garapin et al. (1981) J. Mol. Biol. 150:1, which are incorporated by reference herein in their entireties.

The expression levels of an antibody molecule can be increased by vector amplification (for a review, see Bebbington and Hentschel (1987) "The Use of Vectors Based on Gene Amplification for the Expression of Cloned Genes in Mammalian Cells in DNA Cloning" (Academic Press, NY) Vol. 3. When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

In vitro production allows scale-up to give large amounts of the desired polypeptides. Techniques for mammalian cell cultivation under tissue culture conditions are known in the art and include homogeneous suspension culture, e.g. in an airlift reactor or in a continuous stirrer reactor, or immobilized or entrapped cell culture, e.g. in hollow fibers, microcapsules, on agarose microbeads or ceramic cartridges. If necessary and/or desired, the solutions of polypeptides can be purified by the customary chromatography methods, for example gel filtration, ion-exchange chromatography, chromatography over DEAE-cellulose or (immuno-)affinity chromatography, e.g., after preferential biosynthesis of a synthetic hinge region polypeptide or prior to or subsequent to the HIC chromatography step described herein.

Genes encoding anti-CXCL13 antibodies, or antigen-binding fragments, variants, or derivatives thereof of the invention can also be expressed in non-mammalian cells such as insect, bacteria or yeast or plant cells. Bacteria that readily take up nucleic acids include members of the enterobacteriaceae, such as strains of *Escherichia coli* or *Salmonella*; Bacillaceae, such as *Bacillus subtilis*; *Pneumococcus*; *Streptococcus*, and *Haemophilus influenzae*. It will further be appreciated that, when expressed in bacteria, the heterologous polypeptides typically become part of inclusion bodies. The heterologous polypeptides must be isolated, purified and then assembled into functional molecules. Where tetravalent forms of antibodies are desired, the subunits will then self-assemble into tetravalent antibodies (WO 02/096948A2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., *EMBO J.* 2:1791 (1983)), in which the antibody coding sequence may be ligated individually into the vector in frame with the lacZ coding region so that a fusion protein is produced; pIN vectors (Inouye and Inouye, *Nucleic Acids Res.* 13:3101-3109 (1985); Van Heeke and Schuster, *J. Biol. Chem.* 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In addition to prokaryotes, eukaryotic microbes may also be used. *Saccharomyces cerevisiae*, or common baker's yeast, is the most commonly used among eukaryotic microorganisms although a number of other strains are commonly available, e.g., *Pichia pastoris*.

For expression in *Saccharomyces*, the plasmid YRp7, for example, (Stinchcomb et al., *Nature* 282:39 (1979); Kingsman et al., *Gene* 7:141 (1979); Tschemper et al., *Gene* 10:157 (1980)) is commonly used. This plasmid already contains the TRP1 gene, which provides a selection marker for a mutant strain of yeast lacking the ability to grow in tryptophan, for example ATCC No. 44076 or PEP4-1 (Jones, *Genetics* 85:12 (1977)). The presence of the trp1 lesion as a characteristic of the yeast host cell genome then provides an effective environment for detecting transformation by growth in the absence of tryptophan.

In an insect system, *Autographa californica* nuclear polyhedrosis virus (AcNPV) is typically used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Alternatively, a method for increasing the affinity of antibodies of the invention is disclosed in U.S. Patent Application Publication No. 2002 0123057 A1.

Treatment Methods Using Therapeutic Anti-CXCL13 Antibodies

Lymphoid chemokine CXCL13 is expressed by follicular dendritic cells (FDCs) and macrophages. Through its receptor, CXCR5, which is found on a variety of immune cells (e.g., B cells, follicular helper T cells, and recently-activated T cells), CXCL13 induces intracellular changes necessary for maintenance of immune system homeostasis, lymphoid organogenesis, leukocyte trafficking and chemotactic migration as well as development of secondary lymphoid tissue (e.g. germinal centers). Overexpression of CXCL13 and its receptor CXCR5 have been implicated into a variety of autoimmune diseases (e.g., Multiple sclerosis (see, e.g., Corcione et al., *PNAS* 101(30):11064-11069 (2004); Serafini et al., *Brain Pathol.* 14:164-174 (2004); Magliozzi et al., *Brain* 130: 1089-1104 (2007)), arthritis (e.g., Rheumatoid arthritis (see, e.g., Rioja et al., *Arthritis & Rheumatism* 58(8):2257-2267 (2008); Shi et al., *J. Immun.* 166:650-655 (2001); Schmutz et al., *Arthritis Restearch and Therapy* 7:R217-R229 (2005); Hjelmström et al., *J. Leukocyte Bio.* 69:331-339 (2001)), chronic gastritis (see, e.g., Hjelmström et al.; Mazzucchelli et al., *Brain* 130:1089-1104 (2007)), gastric lymphomas (see, e.g., id.; Nobutani et al., *FEMS Immunol Med Microbiol* 60:156-164 (2010)), transplant rejection (see, e.g., Steinmetz et al., *Kidney International* 67:1616-1621 (2005)), Sjogren syndrome (SS) (see, e.g., Barone et al., *J. Immuno.* 180:5130-5140 (2008); Hjelmström et al.), Systemic Lupus Erythematosis (SLE) (see, e.g., Steinmetz et al., Lee et al., *J. Rheum.* 37(1):45-52 (2010); Schiffer et al., *J. Immun.* 171:489-497 (2003)), active mixed cryoglobulinemia (MC) vasculitis in Hepatitis C virus infection (see, e.g., Sansonno et al., *Blood* 112(5): 1620-1627 (2008)), Juvenile dermatomyositis (see, e.g., de Padilla et al., *Arthritis & Rheumatism* 60(4):1160-1172 (2009)), and Myastenia Gravis (see, e.g., Matsumoto et al., *J. Immuno.* 176:5100-5107 (2006); Meraouna et al., *Blood* 108(2):432-440 (2006); Saito et al., *J. Neuroimmunol* 170: 172-178 (2005)) and certain cancers (e.g., Burkitt's lymphoma (see, e.g., Førster et al., *Blood* 84:830-840 (1994); Førster et al., *Cell* 87:1037-1047 (1996)), Non-Hodgkin Lymphoma (see, e.g., Trentin et al., *Ann. Rev. Immunol.* 6:251-81 (1988); Gong et al., *J. Immunol.* 174: 817-826 (2005); Hamaguchi et al., *J. Immunol.* 174:4389-4399 (2005)), Carcinoma (e.g., colon and pancreatic) (see, e.g., Gunther et al., *Int. J. Cancer* 116:726-733 (2005); Meijer et al., *Cancer Res.* 66: 9576-9582 (2006)), breast cancer (see, e.g., Panse et al., *British Journal of Cancer* 99:930-938 (2008)), Chronic lymphocytic leukemia (CLL) (see, e.g., Bürkle et al., *Blood* 110:3316-3325 (2007)), and prostate cancer (see, e.g., Singh et al., *Cancer Letters* 283 (1):29-35 (2009)). Methods of the invention for inhibition of CXCL13 activity would be expected to have a therapeutic effect on the above-mentioned disorders.

Certain methods of the invention are directed to the use of anti-CXCL13 binding molecules, e.g., antibodies, including antigen-binding fragments, variants, and derivatives thereof, to treat patients having a disease associated with CXCL13-expressing cells, e.g., CXCL13-overexpressing cells. By "CXCL13-expressing cell" is intended normal and malignant cells expressing CXCL13 antigen. Methods for detecting CXCL13 expression in cells are well known in the art and include, but are not limited to, PCR techniques, immunohistochemistry, flow cytometry, Western blot, ELISA, and the like.

Although the following discussion refers to diagnostic methods and treatment of various diseases and disorders with an anti-CXCL13 antibody of the invention, the methods described herein are also applicable to the antigen-binding fragments, variants, and derivatives of these anti-CXCL13 antibodies that retain the desired properties of the anti-CXCL13 antibodies of the invention, e.g., capable of specifically binding CXCL13, e.g., human, primate, mouse, or human and mouse CXCL13, and having CXCL13 neutralizing activity.

In one embodiment, treatment includes the application or administration of an anti-CXCL13 binding molecule, e.g., an antibody or antigen binding fragment thereof, of the current invention to a patient, or application or administration of the anti-CXCL13 binding molecule to an isolated tissue or cell line from a patient, where the patient has a disease, a symptom of a disease, or a predisposition toward a disease. In another embodiment, treatment is also intended to include the application or administration of a pharmaceutical composition comprising the anti-CXCL13 binding molecule, e.g., an antibody or antigen binding fragment thereof, of the current invention to a patient, or application or administration of a pharmaceutical composition comprising the anti-CXCL13 binding molecule to an isolated tissue or cell line from a patient, who has a disease, a symptom of a disease, or a predisposition toward a disease.

The anti-CXCL13 binding molecules, e.g., antibodies or binding fragments thereof, of the present invention are useful for the treatment of various malignant and non-malignant tumors. By "anti-tumor activity" is intended a reduction in the rate of malignant CXCL13-expressing cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. For example, therapy with at least one anti-CXCL13 antibody causes a physiological response that is beneficial with respect to treatment of disease states associated with CXCL13-expressing cells in a human.

In one embodiment, the invention relates to anti-CXCL13 binding molecules, e.g., antibodies or binding fragments thereof, according to the present invention for use as a medicament, in particular for use in the treatment or prophylaxis of cancer or for use in a precancerous condition or lesion. In certain embodiments, an anti-CXCL13 binding molecule, e.g., an antibody or binding fragment thereof, e.g., MAb 5261, of the invention is used for the treatment of a CXCL13 over-expressing cancer. In certain embodiments, an anti-CXCL13 binding molecule, e.g., an antibody or binding fragment thereof, of the invention is used for the treatment of a CXCL13 expressing or over-expressing leukemia, lymphoma (e.g., MALT lymphoma), colon, pancreatic, stomach, esophageal, breast, or prostate cancer. In one embodiment, an anti-CXCL13 binding molecule, e.g., an antibody or binding fragment thereof, of the invention is used for the treatment of a carcinoma, e.g., colon or prostate carcinoma. In one embodiment, the an anti-CXCL13 binding molecule, e.g., an antibody or binding fragment thereof, of the invention is used for the treatment of a CXCR5 expressing or over-expressing cancer.

The effectiveness of an anti-CXCL13 binding molecule, e.g., an antibody or binding fragment thereof, for the treatment or prevention of cancer can be shown using animal models. For example, the effectiveness of an anti-CXCL13 binding molecule, e.g., an antibody or binding fragment thereof, of the invention for the treatment or prevention of prostate cancer can be shown using an animal model for prostate cancer, e.g., mice injected with PC3-luc human prostate carcinoma cells and treated with an anti-CXCL13 binding molecule of the invention. In another example, the effectiveness of an anti-CXCL13 binding molecule, e.g., an antibody or binding fragment thereof, of the invention for the treatment or prevention of colon cancer can be shown using an animal model for colon cancer, e.g., mice injected with CT26 colon carcinoma cells and treated with an anti-CXCL13 binding molecule of the invention. In another example, the effectiveness of an anti-CXCL13 binding molecule, e.g., an antibody or binding fragment thereof, of the invention for the treatment or prevention of MALT lymphoma can be shown using an animal model for gastric MALT lymphoma, e.g., mice infected with *Helicobacter* bacteria (see Nobutani et al. (2010)) and treated with an anti-CXCL13 binding molecule of the invention. The Nobutani et al. model may also be used to assess the effectiveness of an anti-CXCL13 binding molecule, e.g., an antibody or binding fragment thereof, of the invention for the reduction of gastric lymphoid follicles of *Helicobacter*-infected tissues.

In accordance with the methods of the present invention, at least one anti-CXCL13 binding molecule, e.g., an antibody or antigen binding fragment thereof, as defined elsewhere herein is used to promote a positive therapeutic response with respect to a malignant human cell. By "positive therapeutic response" with respect to cancer treatment is intended an improvement in the disease in association with the anti-tumor activity of these binding molecules, e.g., antibodies or fragments thereof, and/or an improvement in the symptoms associated with the disease. That is, an anti-proliferative effect, the prevention of further tumor outgrowths, a reduction in tumor size, a decrease in tumor vasculature, a reduction in the number of cancer cells, and/or a decrease in one or more symptoms associated with the disease can be observed. Thus, for example, an improvement in the disease may be characterized as a complete response. By "complete response" is intended an absence of clinically detectable disease with normalization of any previously abnormal radiographic studies, bone marrow, and cerebrospinal fluid (CSF). Such a response must persist for at least one month following treatment according to the methods of the invention. Alternatively, an improvement in the disease may be categorized as being a partial response. By "partial response" is intended at least about a 50% decrease in all measurable tumor burden (i.e., the number of tumor cells present in the subject) in the absence of new lesions and persisting for at least one month. Such a response is applicable to measurable tumors only.

Tumor response can be assessed for changes in tumor morphology (i.e., overall tumor burden, tumor cell count, and the like) using screening techniques such as bioluminescent imaging, for example, luciferase imaging, bone scan imaging, and tumor biopsy sampling including bone marrow aspiration (BMA). In addition to these positive therapeutic responses, the subject undergoing therapy with the anti-CXCL13 binding molecule, e.g., an antibody or antigen-binding fragment thereof, may experience the beneficial effect of an improvement in the symptoms associated with the disease. For example, the subject may experience a decrease in the so-called B symptoms, e.g., night sweats, fever, weight loss, and/or urticaria.

The anti-CXCL13 binding molecules, e.g., antibodies or antigen binding fragments thereof, described herein may also find use in the treatment or prevention of inflammatory diseases and deficiencies or disorders of the immune system that are associated with CXCL13 expressing cells. Inflammatory diseases are characterized by inflammation and tissue destruction, or a combination thereof. By "anti-inflammatory activity" is intended a reduction or prevention of inflammation. "Inflammatory disease" includes any inflammatory immune-mediated process where the initiating event or target of the immune response involves non-self antigen(s), including, for example, alloantigens, xenoantigens, viral antigens, bacterial antigens, unknown antigens, or allergens.

In one embodiment, the inflammatory disease is associated with a bacterial infection, e.g., a *Helicobacter* infection, e.g., a *H. pylori, H heilmannii, H. acinonychis, H. anseris, H. aurati, H. baculiformis, H. bilis, H. bizzozeronii, H. brantae, H. candadensis, H. canis, H. cholecystus, H. cinaedi, H. cynogastricus, H. equorum, H. fells, H. fenelliae, H. ganmani, H. hepaticus, H. mesocricetorum, H. marmotae, H. muridarum, H. mustelae, H. pametensis, H. pullorum, H. rappini, H. rodentium, H. salomonis, H. suis, H. trogontum, H. typhlonius,* and *H. winghamensis* infection. In certain embodiments, the *Helicobacter* infection is a *H. pylori* or a *H. heilmannii* infection. In a further embodiment, the *Helicobacter*-associated inflammatory disease is MALT lymphoma, a gastric cancer (e.g., esophageal or stomach cancer), a gastric or duodenal ulcer, gastritis (an inflammation of the stomach lining), or a gastric lesion (see, e.g., Chen et al., *J Clin Pathol* 55(2):133-7 (2002); Genta et al., *Hum Pathol* 24(6):577-83 (1993); Okiyama et al., *Pathol Int* 55(7):398-404 (2005)).

In one embodiment, the inflammatory disease is an inflammatory disorder of the peripheral or central nervous system.

Further, for purposes of the present invention, the term "inflammatory disease(s)" includes, but is not limited to, "autoimmune disease(s)." As used herein, the term "autoimmunity" is generally understood to encompass inflammatory immune-mediated processes involving "self" antigens. In autoimmune diseases, self antigen(s) trigger host immune responses.

In one embodiment, the anti-CXCL13 binding molecule, e.g., an antibody or antigen binding fragment, of the invention is used to treat or prevent multiple sclerosis (MS). MS, also known as disseminated sclerosis or encephalomyelitis disseminata, is an autoimmune condition in which the immune system attacks the central nervous system, leading to demyelination. The name "multiple sclerosis" refers to the scars (scleroses, also referred to as plaques or lesions) that form in the nervous system. MS lesions commonly involve white matter areas close to the ventricles of the cerebellum, brain stem, basal ganglia and spinal cord, and the optic nerve. MS results in destruction of oligodendrocytes, the cells responsible for creating and maintaining the myelin sheath. MS results in a thinning or complete loss of myelin and, as the disease advances, transection of axons.

Neurological symptoms can vary with MS, and the disease often progresses to physical and cognitive disability. MS takes several forms, with new symptoms occurring either in discrete attacks (relapsing forms) or slowly accumulating over time (progressive forms). Between attacks, symptoms may go away completely, but permanent neurological damage often results, especially as the disease advances.

Experimental Autoimmune Encephalomyelitis (EAE) is a widely accepted animal model of multiple sclerosis. EAE is a demyelinating disease of the CNS that progressively results in escalating degrees of ascending paralysis with inflammation primarily targeting the spinal cord. The disease can assume an acute, chronic or relapsing-remitting course that is dependent upon the method of induction and type of animal used. Bagaeva et al. has shown that follicles containing B-cells and CXCL13-expressing dendritic cells formed in inflamed meninges of mice with relapsing-remitting EAE with levels of CXCL13 expression rising steadily throughout the course of disease. CXCL13-deficient mice experienced mild disease with decreased relapse rate, and blockade of CXCL13 with anti-CXCL13 MAb led to the disease attenuation in passively induced EAE in B10.PL mice. Bagaeva et al., *J. Immuno.* 176:7676-7685 (2006).

Neutralization of CXCL13 using an anti-CXCL13 monoclonal antibody or antigen binding fragment thereof of the invention, e.g., MAb 5261, may be used to reduce the severity of MS through several different mechanisms, e.g., blockade of CXCL13 interaction with its receptor resulting, e.g., in interference with B and follicular B-helper T cell migration into inflamed tissues and germinal center formation.

In one embodiment, the anti-CXCL13 binding molecule, e.g., an antibody or antigen binding fragment, of the invention is used to treat or prevent systemic lupus erythematosus (SLE or lupus). SLE is an autoimmune disease that involves multiple organs and is characterized by the spontaneous formation of ectopic germinal centers and autoantibody production against a number of nuclear antigens. SLE most often affects the heart, joints, skin, lungs, blood vessels, liver, kidneys, and nervous system.

Activated T cells, B cells and their migration-promoting chemokine CXCL13 play critical roles in the formation of organized lymphoid tissue seen in inflamed ectopic sites of multiple autoimmune disorders including SLE. Lupus-prone New Zealand Black X New Zealand White F1 (NZB/NZWF1) mice spontaneously develop high-titer anti-dsDNA antibodies and severe proliferative glomerulonephritis caused by formation of immune complexes in glomeruli of the kidneys. The development of lupus-like symptoms in these mice is accompanied by increased expression of CXCL13 by dendritic cells in kidneys and thymus (Ishikawa et al., *J. Exp. Med.* 193(12):1393-1402 (2001); Schiffer et al., *J. Immun.* 171:489-497 (2003)).

Neutralization of CXCL13 using an anti-CXCL13 monoclonal antibody or antigen binding fragment thereof of the invention, e.g., MAb 5261, may be used to reduce the severity of SLE through several different mechanisms, e.g., blockade of CXCL13 interaction with its receptor resulting, e.g., in interference with B and follicular B-helper T cell migration into inflamed tissues and germinal center formation.

In one embodiment, the anti-CXCL13 binding molecule, e.g., an antibody or antigen binding fragment, of the invention is used to treat or prevent arthritis, e.g., Rheumatoid Arthritis. Rheumatoid arthritis (RA) is one of the most common autoimmune diseases which affect 2-4% of people in the United States. It is a chronic, progressive, systemic inflammatory disorder characterized by fusion of synovial joints, cartilage erosion and bone destruction. In RA, T-cells, B-cells, macrophages and dendritic cells (DCs) accumulate in the synovial layer forming pannus (invasive region of synovium that erodes into cartilage and bone). Moreover, T and B cells within the synovial lesions organize into lymphoid germinal center-like structures that support autoantibody (rheumatoid factor) production and, therefore, directly contribute to the disease pathogenesis (Takemura et al., *J. Immuno.* 167:1072-1080 (2001); Shi et al., *J. of Immuno.* 166:650-655 (2001)).

Lymphoid chemokine CXCL13, produced by synovial fibroblasts, selected endothelial cells, synovial antigen-primed T helper cells and FDCs (Takemura et al. (2001); Shi et al. (2001); Manzo et al., *Arthritis & Rheumatism* 58(11): 3377-3387 (2008)), plays a critical role in the germinal center formation in the synovial tissue, by directing CXCR5-positive lymphoid cell (primarily B cells and follicular T helper cells) migration into the inflamed synovium.

Clinically, plasma levels of CXCL13 in RA patients correlated with disease severity, as significantly higher levels of CXCL13 were found in plasma from the patients with active RA comparing to the controls and the patient with the quiescent disease (Rioja et al., *Arthritis & Rheumatism* 58(8):2257-2267 (2008)). In addition, CXCR5 receptor was upregulated in synovium of RA patients and present on infiltrating B and T cells and also on macrophages and endothelial cells (Schmutz et al., *Arthritis Research Therapy* 7:R217-R229 (2005)).

Collagen-induced arthritis (CIA) in mice and rats is a well-established model of human Rheumatoid arthritis (RA). The disease is typically induced by intradermal injection of bovine type II collagen emulsified in Complete Freund's Adjuvant (CFA) and is characterized by production of mouse collagen antibodies and, subsequently, progressive development of arthritis in the paws. Stannard et al. showed that CXCL13 neutralization with rat anti-murine CXCL13 antibodies led to significant reduction in arthritic score and the severity of joint destruction in arthritic DBA/1 mice. Stannard et al., "Neutralization of CXCL13 impacts B-cell trafficking and reduces severity of established experimental arthritis," Presented at American College of Rheumatology 2008 Annual Scientific Meeting (2008).

Neutralization of CXCL13 using an anti-CXCL13 monoclonal antibody or antigen binding fragment thereof of the invention, e.g., MAb 5261, may be used to reduce the severity of arthritis, e.g., Rheumatoid Arthritis, through several different mechanisms, e.g., blockade of CXCL13 interaction with its receptor resulting, e.g., in interference with B and follicular B-helper T cell migration into inflamed tissues and germinal center formation. In addition, an anti-CXCL13 monoclonal antibody or antigen binding fragment thereof of the invention, e.g., MAb 5261, may be used to reduce RANKL expression and bone loss, e.g., in a subject with RANKL overexpression.

In accordance with the methods of the present invention, at least one anti-CXCL13 binding molecule, e.g., an antibody or antigen binding fragment thereof, as defined elsewhere herein is used to promote a positive therapeutic response with respect to treatment or prevention of an autoimmune disease and/or inflammatory disease. By "positive therapeutic response" with respect to an autoimmune disease and/or inflammatory disease is intended an improvement in the disease in association with the anti-inflammatory activity, anti-angiogenic activity, anti-apoptotic activity, or the like, of these antibodies, and/or an improvement in the symptoms associated with the disease. That is, an anti-proliferative effect, the prevention of further proliferation of the CXCL13-expressing cell, a reduction in the inflammatory response including but not limited to reduced secretion of inflammatory cytokines, adhesion molecules, proteases, immunoglobulins (in instances where the CXCL13 bearing cell is a B cell), combinations thereof, and the like, increased production of anti-inflammatory proteins, a reduction in the number of autoreactive cells, an increase in immune tolerance, inhibition of autoreactive cell survival, reduction in apoptosis, reduction in endothelial cell migration, increase in spontaneous monocyte migration, reduction in and/or a decrease in one or more symptoms mediated by stimulation of CXCL13-expressing cells can be observed. Such positive therapeutic responses are not limited to the route of administration and may comprise administration to the donor, the donor tissue (such as for example organ perfusion), the host, any combination thereof, and the like.

Clinical response can be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with the anti-CXCL13 binding molecule, e.g., an antibody or antigen-binding fragment thereof, may experience the beneficial effect of an improvement in the symptoms associated with the disease.

A further embodiment of the invention is the use of an anti-CXCL13 binding molecule, e.g., antibodies or antigen binding fragments thereof, for diagnostic monitoring of protein levels in tissue as part of a clinical testing procedure, e.g., to determine the efficacy of a given treatment regimen. For example, detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, 13-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{35}$S, or $^{3}$H.

Pharmaceutical Compositions and Administration Methods

Methods of preparing and administering the anti-CXCL13 binding molecule, e.g., antibodies, or antigen-binding fragments, variants, or derivatives thereof, of the invention to a subject in need thereof are well known to or are readily determined by those skilled in the art. The route of administration of the anti-CXCL13 binding molecule, e.g, antibody, or antigen-binding fragment, variant, or derivative thereof, may be, for example, oral, parenteral, by inhalation or topical. The term parenteral as used herein includes, e.g., intravenous, intraarterial, intraperitoneal, intramuscular, subcutaneous, rectal, or vaginal administration. While all these forms of administration are clearly contemplated as being within the scope of the invention, an example of a form for administration would be a solution for injection, in particular for intravenous or intraarterial injection or drip. Usually, a suitable pharmaceutical composition for injection may comprise a buffer (e.g. acetate, phosphate or citrate buffer), a surfactant (e.g. polysorbate), optionally a stabilizer agent (e.g. human albumin), etc. However, in other methods compatible with the teachings herein, anti-CXCL13 binding molecules, e.g., antibodies, or antigen-binding fragments, variants, or derivatives thereof, of the invention can be delivered directly to the site of the adverse cellular population thereby increasing the exposure of the diseased tissue to the therapeutic agent.

As discussed herein, anti-CXCL13 binding molecules, e.g., antibodies, or antigen-binding fragments, variants, or derivatives thereof, of the invention may be administered in a pharmaceutically effective amount for the in vivo treatment of CXCL13-expressing cell-mediated diseases such as certain types of cancers, autoimmune diseases, and inflammatory diseases including central nervous system (CNS) and peripheral nervous system (PNS) inflammatory diseases. In this regard, it will be appreciated that the disclosed binding molecules of the invention will be formulated so as to facilitate administration and promote stability of the active agent. In certain embodiments, pharmaceutical compositions in accordance with the present invention comprise a pharmaceutically acceptable, non-toxic, sterile carrier such as physiological saline, non-toxic buffers, preservatives and the like. For the purposes of the instant application, a pharmaceutically effective amount of an anti-CXCL13 binding molecule, e.g., an antibody, or antigen-binding fragment, variant, or derivative thereof, conjugated or unconjugated, shall be held to mean an amount sufficient to achieve effective binding to a target and to achieve a benefit, e.g., to ameliorate symptoms of a disease or disorder or to detect a substance or a cell.

The pharmaceutical compositions used in this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. In the subject invention, pharmaceutically acceptable carriers include, but are not limited to, 0.01-0.1 M, e.g., 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Suitable formulations for use in the therapeutic methods disclosed herein are described in Remington's Pharmaceutical Sciences (Mack Publishing Co.) 16th ed. (1980).

Prevention of the action of microorganisms can be achieved by various antibacterial and antifungal agents, for example, parabens, chlorobutanol, phenol, ascorbic acid, thimerosal and the like. In certain cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an anti-CXCL13 antibody, or antigen-binding fragment, variant, or derivative thereof, by itself or in combination with other active agents) in the required amount in an appropriate solvent with one or a combination of ingredients enumerated herein, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yields a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations may be packaged and sold in the form of a kit such as those described in U.S. patent application Ser. No. 09/259,337. Such articles of manufacture will preferably have labels or package inserts indicating that the associated compositions are useful for treating a subject suffering from, or predisposed to, a disease or disorder.

Parenteral formulations may be a single bolus dose, an infusion or a loading bolus dose followed with a maintenance dose. These compositions may be administered at specific fixed or variable intervals, e.g., once a day, or on an "as needed" basis.

Certain pharmaceutical compositions used in this invention may be orally administered in an acceptable dosage form including, e.g., capsules, tablets, aqueous suspensions or solutions. Certain pharmaceutical compositions also may be administered by nasal aerosol or inhalation. Such compositions may be prepared as solutions in saline, employing benzyl alcohol or other suitable preservatives, absorption promoters to enhance bioavailability, and/or other conventional solubilizing or dispersing agents.

The amount of an anti-CXCL13 binding molecule, e.g., antibody, or fragment, variant, or derivative thereof, that may be combined with the carrier materials to produce a single dosage form will vary depending upon the host treated and the particular mode of administration. The composition may be administered as a single dose, multiple doses or over an established period of time in an infusion. Dosage regimens also may be adjusted to provide the optimum desired response (e.g., a therapeutic or prophylactic response).

In keeping with the scope of the present disclosure, anti-CXCL13 antibodies, or antigen-binding fragments, variants, or derivatives thereof of the invention may be administered to a human or other animal in accordance with the aforementioned methods of treatment in an amount sufficient to produce a therapeutic effect. The anti-CXCL13 antibodies, or antigen-binding fragments, variants, or derivatives thereof of the invention can be administered to such human or other animal in a conventional dosage form prepared by combining an antibody of the invention, e.g., MAb 5261, with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of anti-CXCL13 binding molecules, e.g., antibodies, or antigen-binding fragments, variants, or derivatives thereof, of the invention may prove to be particularly effective.

By "therapeutically effective dose or amount" or "effective amount" is intended an amount of anti-CXCL13 binding molecule, e.g., antibody or antigen binding fragment thereof, that when administered brings about a positive therapeutic response with respect to treatment of a patient with a disease to be treated.

Therapeutically effective doses of the compositions of the present invention, for treatment of CXCL13-expressing cell-mediated diseases such as certain types of cancers, e.g., leukemia, lymphoma (e.g., MALT lymphoma), colon, breast, esophageal, stomach, and prostate cancer; autoimmune diseases, e.g., lupus, arthritis, multiple sclerosis, and inflammatory diseases including central nervous system (CNS) and peripheral nervous system (PNS) inflammatory diseases, vary depending upon many different factors, including means of administration, target site, physiological state of the patient, whether the patient is human or an animal, other medications administered, and whether treatment is prophylactic or therapeutic. Usually, the patient is a human, but non-human mammals including transgenic mammals can also be treated. Treatment dosages may be titrated using routine methods known to those of skill in the art to optimize safety and efficacy.

The amount of at least one anti-CXCL13 binding molecule, e.g., antibody or binding fragment thereof, to be administered is readily determined by one of ordinary skill in the art without undue experimentation given the disclosure of the present invention. Factors influencing the mode of administration and the respective amount of at least one anti-CXCL13 binding molecule, e.g., antibody, antigen-binding fragment, variant or derivative thereof include, but are not limited to, the severity of the disease, the history of the disease, and the age, height, weight, health, and physical condition of the individual undergoing therapy. Similarly, the amount of anti-CXCL13 binding molecule, e.g., antibody, or fragment, variant, or derivative thereof, to be administered will be dependent upon the mode of administration and whether the subject will undergo a single dose or multiple doses of this agent.

The present invention also provides for the use of an anti-CXCL13 binding molecule, e.g., an antibody or antigen-binding fragment, variant, or derivative thereof, in the manufacture of a medicament for treating an autoimmune disease and/or inflammatory disease, including, e.g., MS, arthritis, lupus, gastritis, an ulcer, or a cancer.

Diagnostics

The invention further provides a diagnostic method useful during diagnosis of CXCL13-expressing cell-mediated diseases such as certain types of cancers and inflammatory diseases including autoimmune diseases, which involves measuring the expression level of CXCL13 protein or transcript in tissue or other cells or body fluid from an individual and comparing the measured expression level with a standard CXCL13 expression level in normal tissue or body fluid, whereby an increase in the expression level compared to the standard is indicative of a disorder. In certain embodiments, the anti-CXCL13 antibodies of the invention or antigen-binding fragments, variants, and derivatives thereof, e.g., MAb 5261, MAb 5378, MAb 5080, MAb 1476, 3D2, or 3C9, are used in diagnosis of cancer, multiple sclerosis, arthritis, or lupus.

The anti-CXCL13 antibodies of the invention and antigen-binding fragments, variants, and derivatives thereof, can be used to assay CXCL13 protein levels in a biological sample using classical immunohistological methods known to those of skill in the art (e.g., see Jalkanen, et al., *J. Cell. Biol.* 101:976-985 (1985); Jalkanen et al., *J. Cell Biol.* 105:3087-3096 (1987)). Other antibody-based methods useful for detecting CXCL13 protein expression include immunoassays, such as the enzyme linked immunosorbent assay (ELISA), immunoprecipitation, or Western blotting. Suitable assays are described in more detail elsewhere herein.

By "assaying the expression level of CXCL13 polypeptide" is intended qualitatively or quantitatively measuring or estimating the level of CXCL13 polypeptide in a first biological sample either directly (e.g., by determining or estimating absolute protein level) or relatively (e.g., by comparing to the disease associated polypeptide level in a second biological sample). In one embodiment, the CXCL13 polypeptide expression level in the first biological sample is measured or estimated and compared to a standard CXCL13 polypeptide level, the standard being taken from a second biological sample obtained from an individual not having the disorder or being determined by averaging levels from a population of individuals not having the disorder. As will be appreciated in the art, once the "standard" CXCL13 polypeptide level is known, it can be used repeatedly as a standard for comparison.

By "biological sample" is intended any biological sample obtained from an individual, cell line, tissue culture, or other source of cells potentially expressing CXCL13. Methods for obtaining tissue biopsies and body fluids from mammals are well known in the art.

Immunoassays

Anti-CXCL13 antibodies, or antigen-binding fragments, variants, or derivatives thereof of the invention may be assayed for immunospecific binding by any method known in the art. The immunoassays that can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, (1994) Current Protocols in Molecular Biology (John Wiley & Sons, Inc., NY) Vol. 1, which is incorporated by reference herein in its entirety).

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., $^3$H or $^{125}$I) in the presence of increasing amounts of an unlabeled second antibody.

The binding activity of a given lot of anti-CXCL13 antibody, or antigen-binding fragment, variant, or derivative thereof may be determined according to well known methods. Those skilled in the art will be able to determine operative and optimal assay conditions for each determination by employing routine experimentation.

There are a variety of methods available for measuring the affinity of an antibody-antigen interaction, but relatively few for determining rate constants. Most of the methods rely on either labeling antibody or antigen, which inevitably complicates routine measurements and introduces uncertainties in the measured quantities.

Surface plasmon reasonance (SPR) as performed on BIACORE® offers a number of advantages over conventional methods of measuring the affinity of antibody-antigen interactions: (i) no requirement to label either antibody or antigen; (ii) antibodies do not need to be purified in advance, cell culture supernatant can be used directly; (iii) real-time measurements, allowing rapid semi-quantitative comparison of different monoclonal antibody interactions, are enabled and are sufficient for many evaluation purposes; (iv) biospecific surface can be regenerated so that a series of different monoclonal antibodies can easily be compared under identical conditions; (v) analytical procedures are fully automated, and extensive series of measurements can be performed without user intervention. BIAapplications Handbook, version AB (reprinted 1998), BIACORE® code No. BR-1001-86; BIAtechnology Handbook, version AB (reprinted 1998), BIACORE® code No. BR-1001-84. SPR based binding studies require that one member of a binding pair be immobilized on a sensor surface. The binding partner immobilized is referred to as the ligand. The binding partner in solution is referred to as the analyte. In some cases, the ligand is attached indirectly to the surface through binding to another immobilized molecule, which is referred as the capturing molecule. SPR response reflects a change in mass concentration at the detector surface as analytes bind or dissociate.

Based on SPR, real-time BIACORE® measurements monitor interactions directly as they happen. The technique is well suited to determination of kinetic parameters. Comparative affinity ranking is simple to perform, and both kinetic and affinity constants can be derived from the sensorgram data.

When analyte is injected in a discrete pulse across a ligand surface, the resulting sensorgram can be divided into three essential phases: (i) Association of analyte with ligand during sample injection; (ii) Equilibrium or steady state during sample injection, where the rate of analyte binding is balanced by dissociation from the complex; (iii) Dissociation of analyte from the surface during buffer flow.

The association and dissociation phases provide information on the kinetics of analyte-ligand interaction ($k_a$ and $k_d$, the rates of complex formation and dissociation, $k_d/k_a=K_D$). The equilibrium phase provides information on the affinity of the analyte-ligand interaction ($K_D$).

BIAevaluation software provides comprehensive facilities for curve fitting using both numerical integration and global fitting algorithms. With suitable analysis of the data, separate rate and affinity constants for interaction can be obtained from simple BIACORE® investigations. The range of affinities measurable by this technique is very broad ranging from mM to pM.

Epitope specificity is an important characteristic of a monoclonal antibody. Epitope mapping with BIACORE®, in contrast to conventional techniques using radioimmunoassay, ELISA or other surface adsorption methods, does not require labeling or purified antibodies, and allows multi-site specificity tests using a sequence of several monoclonal antibodies. Additionally, large numbers of analyses can be processed automatically.

Pair-wise binding experiments test the ability of two MAbs to bind simultaneously to the same antigen. MAbs directed against separate epitopes will bind independently, whereas MAbs directed against identical or closely related epitopes will interfere with each other's binding. These binding experiments with BIACORE® are straightforward to carry out.

For example, one can use a capture molecule to bind the first Mab, followed by addition of antigen and second MAb sequentially. The sensorgrams will reveal: (1) how much of the antigen binds to first Mab, (2) to what extent the second MAb binds to the surface-attached antigen, (3) if the second MAb does not bind, whether reversing the order of the pair-wise test alters the results.

Peptide inhibition is another technique used for epitope mapping. This method can complement pair-wise antibody binding studies and can relate functional epitopes to structural features when the primary sequence of the antigen is known. Peptides or antigen fragments are tested for inhibition of binding of different MAbs to immobilized antigen. Peptides which interfere with binding of a given MAb are assumed to be structurally related to the epitope defined by that MAb.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hal12003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Example 1

Selection and Characterization of Mouse Antibodies Specific for Human CXCL13

Hybridoma generation. Swiss Webster mice were immunized with Keyhole limpet hemocyanin (KLH)-conjugated human CXCL13. After three immunizations, spleen was harvested from the mouse with the highest anti-CXCL13 titer and hybridomas were generated by fusion of spleen cells with SP2/0 myeloma cells using standard procedures.

Hybridoma clones were screened by ELISA for binding to human and mouse CXCL13 protein. ELISA plates were coated with about 100 nM of human (Peprotech: #300-47) or mouse (Peprotech: #250-24) CXCL13 protein overnight at room temperature (RT). After the plates were washed and blocked, dilutions of standard anti-CXCL13 antibodies (R&D Systems: rat anti-mouse MAb 470 and mouse anti-human MAb 801) or hybridoma supernatant were added and incubated for 1 hour at RT. The plates were washed and secondary antibodies (goat anti-mouse IgG-HRP for hybridoma supernatant and MAb 801; donkey anti-rat IgG-HRP for MAb 470) were added and incubated for 1 hour at RT. The plates were washed and developed with tetramethylbenzidine (TMB) substrate reagents A and B (BD Biosciences: #555214) mixed at equal volumes for 15 minutes in the dark and read at 450/570 wavelengths. Two positive hybridoma clones, labelled "3D2" and "3C9", both mouse IgG1 antibodies, were selected for further characterization.

Specificity of the hybridoma-produced mouse anti-human antibodies, 3D2 and 3C9, was assessed by ELISA (as described above) on a panel that included recombinant chemokines (Peprotech: mouse and human CXCL13, human IL-8/CXCL8 (#200-08), human IP-10/CXCL10 (#200-10), human MIG/CXCL9 (#300-26), human SDF-1alpha/CXCL12 (#300-28A) and cynomolgus monkey CXCL13) as well as several non-specific control antigens (recombinant human C35, streptavidin (Thermo: #21122), bovine serum albumin (BSA) (SeraCore: #AP-4510-01)), human serum albumin (HAS) (Sigma: #A8763), insulin (Gibco: #12585-014), and hemoglobin (Sigma: #H7379). Commercial antibodies MAb 470 and MAb 801 (R&D Systems) were used as positive controls for mouse and human/cynomolgus monkey CXCL13 binding, respectively.

3D2 and 3C9 were shown to specifically bind CXCL13. Both 3D2 and 3C9 clones demonstrated multi-species CXCL13 specificity as they bound to recombinant human, mouse and cynomolgus monkey CXCL13 (FIGS. 1A-1C). FIG. 1 shows results from duplicate measurements for at least three experiments. 3D2 antibody was shown to have strong binding to recombinant human, mouse and monkey CXCL13. In particular, 3D2 had stronger binding to recombinant mouse CXCL13 compared to 3C9 and MAb 801. 3D2 was further characterized in vitro and in vivo (results shown below). The 3D2 antibody was also used as a prototype for generation of a chimeric and humanized CXCL13 antibodies (results shown below). 3C9 antibody was shown to have the strongest binding to recombinant human CXCL13 compared to 3D2, MAb 470, and MAb 801. 3C9 and 3D2 were used as reagents in Bioassay development (e.g., Epitope Competition ELISA, described below).

3D2 affinity measurements by BIACORE®. The affinity of 3D2, 3C9, MAb 801 and MAb 470 for recombinant human and mouse CXCL13 was measured by BIACORE®. Chemokines were immobilized on a Cl chip in Acetate buffer (pH=5) with human CXCL13 at 1 µg/ml, mouse CXCL13 at 0.3 µg/ml, and negative control SDF-1α at 0.5 µg/ml. 3D2 and 3C9 were diluted in HBS-EP buffer by two-fold from 100 nM to 0.78 nM and from 38 nM to 0.594 nm. MAb 801 and MAB 470 were diluted by two-fold from 50 nM to 0.78 nM and from 19 nM to 0.594 nm. The results showed that the affinity measurement (nM) for 3D2 on human and mouse CXCL13 was significantly lower than that of commercial antibodies MAb 801 and MAb 470, respectively. The results are shown in Table 2.

TABLE 2

Affinity Measurements[1]

| Antibody | Fc | Affinity, nM | |
| --- | --- | --- | --- |
| | | Human CXCL13 | Mouse CXCL13 |
| 3D2 | Mouse IgG1 | 12.9 | 159.3 |
| 3C9 | Mouse IgG1 | 2.5 | NB |
| MAb 801 | Mouse IgG1 | 1.3 | NB |
| MAb 470 | Rat IgG2a | NB | 5.4 |

[1]affinities are for recombinant human and mouse CXCL13;
NB = no binding

3D2 epitope mapping. An epitope mapping study was conducted using Epitope Competition ELISA. Plates were coated with 100 nM recombinant human CXCL13 and incubated with 0.033 nM biotinylated 3D2 prior to addition of competing unlabeled antibodies at various concentrations in excess of the amount of 3D2. The results from a representative experiment are shown in FIG. 2. The results show that 3C9 competes with 3D2 for binding to human CXCL13, but MAb 801 did not compete with 3D2 for binding to human CXCL13.

3D2 binding to native CXCL13. Capture Epitope Competition ELISA was used to assess 3D2 binding to native human and mouse CXCL13. In this assay, native human CXCL13 was obtained from supernatants collected from human IFN-gamma-stimulated THP-1 cells. Human CXCL13 (1:4 dilution of THP1 supernatant or 0.097 nM (1 ng/ml) rhuCXCL13) was captured with 6.6 nM MAb 801 and detected with 0.66 nM biotin-3C9. For appropriate antigen presentation, the chemokine from tissue culture supernatant (or recombinant human CXCL13 which was used as a control) was captured on the ELISA plate by MAb 801. The plate was then incubated with biotinylated 3C9 in the presence of various amounts of unlabeled 3D2. The competition for binding to human CXCL13 that resulted in reduced binding of biotinylated 3C9 was detected by Streptavidin-HRP. As evident from FIG. 3A, 3D2 strongly bound to both native and recombinant human CXCL13 producing statistically similar EC50 values.

Mouse CXCL13-rich organ extracts from TNF-alpha transgenic mice were used as sources of native mouse CXCL13. Mouse CXCL13 (1:40 dilution of TNF-Tg organ extract or 0.5 nM rmuCXCL13) was captured with 33 nM MAb 470 and detected with 3.3 nM biotin-3D2. The chemokine from the extracts (and recombinant mouse CXCL13 which was used as a control) was captured on the ELISA plate by MAb 470. The plate was then incubated with biotinylated 3D2 in the presence of various amounts of unlabeled 3D2. The competition for the binding to mouse CXCL13 that resulted in reduced binding of biotinylated 3D2 was then detected by Streptavidin-HRP. As can be seen from FIG. 3B, 3D2 was able to compete off the biotinylated version of itself and bind to both native and recombinant mouse CXCL13 with equal potency.

For both FIGS. 3A and 3B, each data point represents an average of duplicate measurements from one of at least three independent experiments. Curves were fitted using four-parameter sigmoidal curve fit ($R^2$=0.99). Differences in EC50 values were analyzed by unpaired t-test and were not significant (P>0.05). These results show that the mouse anti-human 3D2 antibody bound not only the recombinant chemokine against which it had been generated, but also native human and mouse chemokines.

Example 2

Anti-CXCL13 Antibody Inhibition of Human B-Cell Migration

Inhibition of CXCL13 function, e.g., B-cell migration, was evaluated using established models that simulate B-cell migration in both human and mouse systems. Migration towards a non-CXCL13 chemokine, SDF-1α (a.k.a. CXCL12), was used as a control to confirm specificity of anti-CXCL13 antibody on inhibition of B-cell migration. Thus, anti-CXCL13 antibodies were tested for inhibition of human CXCL13-induced migration and the absence of an effect on SDF-1α-induced migration.

Inhibition of human B-cell migration towards human CXCL13. The effect of 3D2, 3C9, and MAb 801 on human CXCL13-induced B-cell migration was tested.

Two clonal cell lines, human pre-B-697-hCXCR5 and human pre-B-697-hCXCR4, were used to assess the effects of anti-CXCL13 antibodies on recombinant human CXCL13-dependent migration and recombinant human SDF-1α-dependent migration, respectively. Transwell tissue culture-treated plates with 8 μm pore size and diameter of 6.5 mm (Corning Costar: 3422) were used. Human pre-B-697-hCXCR5 cells were used for rhCXCL13-induced migration, and human pre-B-697-hCXCR4 for were used for rhSDF-1-induced migration (negative control). Cells were resuspended in chemotaxis buffer ((RPMI 1640 with 1-glutamine, 10 mM HEPES, PennStrep and 0.5% BSA) pre-warmed to RT) at $5\times10^6$/ml and returned to 37° C. for 30 minutes. Diluted chemokine (97 nm (1 μg/ml) rhCXCL13 or 12.5 nM (0.1 μg/ml) rhSDF-1α in chemotaxis buffer)+/−antibodies were added into the lower chamber at 590 Owed and pre-incubated for 30 minutes at RT. The cells were added at 100 μl ($5\times10^5$) cells/upper chamber. Plates were incubated overnight at 37° C. Inserts were then removed and Alamar blue was added at 60 μl per well and the plates were incubated at 37° C. for 4 hours. Fluorescence was measured at wavelengths 530 nm and 590 nm.

Migration index was calculated for each condition as follows: ((Migration Index [Isotype control]—Migration Index [antibody])*100)/(Migration Index [Isotype control]). Percent migration inhibition was plotted against log[nM antibody] to obtain a titration curve using Graphpad Prism 5. The results for human CXCL13-induced migration are shown in FIG. 4A. The results are presented as mean of two hCXCL13-induced migration and three hSDF-1-induced migration independent experiments+/−SEM.

Differences in the degrees of inhibition of human CXCL13-induced migration among 3D2, 3C9 and MAb 801 corresponded to the differences in affinities for human CXCL13 (see Table 2 above). Thus, the antibody with the lowest affinity for the chemokine (3D2) appeared to be the weakest inhibitor of human pre-B-hCXCR5 chemotaxis, whereas antibodies with higher, nearly identical affinities (MAb 801 and 3C9) resulted in a high percent inhibition of cell migration (FIG. 4A). None of the anti-human CXCL13 antibodies (3D2, 3C9, or MAb 801) produced any effect on human SDF-1α-mediated chemotaxis of human pre-B-hCXCR4 (5) cells (FIG. 4B). Whereas, positive control goat anti-human SDF-1α antibody (MAb 87A) strongly inhibited SDF-1α-dependent migration.

Inhibition of mouse CXCL13-dependent migration of mouse splenocytes. Anti-CXCL13 antibodies were tested for their ability to inhibit recombinant mouse CXCL13-mediated chemotaxis of mouse spleenocytes (obtained from mechanically dissociated spleens). The assay was performed using essentially the same protocol as described above for the human CXCL13-dependent B-cell migration assay with minor changes including using 485 nM (5 µg/ml) rmuCXCL13, using transwell plates with smaller pore size (i.e., Transwell tissue culture treated plates with 5 µm pore size and diameter of 6.5 mm (Corning Costar: #3421)), and using higher amounts of cells (10⁶) per well. The effect of the tested antibodies on migration of spleenocytes from two different strains of mice, C57/BL6 and SJL are shown in FIGS. 5A and 5B, respectively. MAb 470 was used as a positive control. Rat and mouse IgG as well as human CXCL13-specific mouse antibody 3C9 were included as negative controls. As shown in FIGS. 5A and 5B, the patterns of inhibition were different between MAb 470 and 3D2. In particular, 3D2 inhibited chemotaxis in a titratable manner, whereas, the effect of MAb 470 was only apparent at the highest antibody concentration of 396 nM. Data comparing the effect of 3D2 on C57Black/6 and SJL/J migration were analyzed by unpaired t-test which produced P value >0.05 indicating an absence of significant differences between two curves. Curves were fitted using four-parameter sigmoidal curve fit ($R^2$=0.99). A comparison of 3D2 effect on SJL/J and C57Black/6 splenocyte migration is shown in FIG. 5C. No significant differences in 3D2 inhibitory profiles between two mouse strains was shown.

Example 3

Anti-CXCL13 Antibody Inhibition of CXCL13-Mediated Endocytosis of Human CXCR5

Inhibition of CXCL13 chemokine function, e.g., CXCL13-mediated endocytosis of CXCR5 receptor, with anti-CXCL13 antibodies was evaluated using an established model for human CXCL13-mediated endocytosis of human CXCR5 receptor (Burke et al., *Blood* 110:2216-3325 (2007)).

Inhibition of CXCL13-mediated endocytosis of human CXCR5 receptor. Binding of a chemokine to its chemokine receptor leads to internalization of the ligand-receptor complex with subsequent activation of intracellular signaling cascade (Neel et al., *Chemokine and Growth Factor Reviews* 16:637-658 (2005)). The flow-based method described in Burkle et al. was adapted to determine the ability of 3D2 to inhibit CXCL13-mediated CXCR5 receptor internalization in both human and mouse cells. For the human CXCL13-mediated endocytosis, hCXCL13 was combined with 3D2, MAb 470 or Mouse IgG (at concentrations 0, 33, 66, 132, 264, and 528 nM) and incubated overnight at 4° C. The next day, the cells were resuspended in diluents (RPMI+0.5% BSA) at 10⁷ cells/ml. The cells were pre-blocked with 10 µg/ml anti-human Fc block for 15 min at 37° C. The cells were then incubated with the CXCL13/antibody mix (50 µl cells:50 µl mix) for 2 hours at 37° C. The cells were then stained with anti-human CXCR5 antibody (BDPharmingen: #558113) for 30 minutes at 4° C. and analyzed by flow cytometry. Similarly, mouse CXCL13-mediated endocytosis was assayed using mCXCL13 combined with 3D2 or Mouse IgG (at concentrations 0, 20, 59, 198, and 528 nM). Inhibition of endocytosis was calculated as follows: % Inhibition=100−[100*(0 CXCL13−geomean)/(0 CXCL13−0 mAB)].

FIG. 6 shows data from representative human and mouse CXCL13 experiments. FIG. 6A shows the effect of 3D2 antibody on human CXCR5 receptor expression on the surface of human pre-B-697-hCXCR5 cells treated with 485 nM (5 µg/ml) of human CXCL13. FIG. 6B shows 3D2-mediated inhibition of mouse CXCR5 receptor internalization in Wehi-231 cells pre-incubated with 1000 nM (10 µg/ml) of mouse CXCL13. In both cases 3D2 efficiently and in a titratable manner interfered with the CXCL13-induced down regulation of CXCR5 receptors. FIG. 6C shows EC50 values which were calculated from sigmoidal dose response curves (shown on the graph) with R2 values equal to 1 (mouse endocytosis) and 0.994 (human endocytosis). The data comparing 3D2 effect on human and mouse receptor endocytosis were analyzed by unpaired t-test which produced a P value >0.05 indicating absence of significant differences between the human CXCL13 and mouse CXCL13 curves.

Example 4

Evaluation of Anti-CXCL13 Antibodies in Mouse Disease Models for Multiple Sclerosis Murine model of Multiple Sclerosis. Experimental Autoimmune Encephalomyelitis (EAE) is a widely accepted animal model of multiple sclerosis. EAE is a demyelinating disease of the CNS that progressively results in escalating degrees of ascending paralysis with inflammation primarily targeting the spinal cord. The disease can assume an acute, chronic or relapsing-remitting course that is dependent upon the method of induction and type of animal used. Thus, EAE can be induced with the components of the CNS, peptides (active induction) and also via cell transfer from one animal to another (passive induction). Complete Freund's Adjuvant (CFA) is used with the extracts or peptides and is often used with pertussis toxin.

RR-EAE-1: 3D2 effect on relapsing-remitting EAE in SJL mice. 3D2 antibody was tested using an active immunization model of EAE. In the "RR-EAE-1" study, relapsing-remitting (RR) disease was induced in SJL/J mice by subcutaneous immunization with proteolipid protein $(PLP)_{139-151}$ peptide epitope (HSLGKWLGHPDKF; SEQ ID NO: 1) in 1 mg/ml CFA enhanced with 5 mg of heat-inactivated *Mycobacterium tuberculosis* strain H37RA. The study included the following treatment groups:

A. Control (mouse IgG) starting at Day 0
B. 3D2 starting at Day 0
C. 3D2 starting at score ≥1

The mice were given intraperitoneal injections of 0.3 mg (15 mg/kg) of antibody twice per week. The treatment started at Day 0 for groups A and B and at the clinical score of ≥1 for group C (the scoring system is described in Table 3 below).

TABLE 3

Summary of Evaluation of the EAE Clinical Signs

| Score | Signs | Description |
|---|---|---|
| 0 | Normal behavior | No neurological signs. |
| 1 | Distal limp tail | The distal part of the tail is limp and droopy. |
| 1.5 | Complete limp tail | The whole tail is loose and droopy. |
| 2 | Righting reflex | Animal has difficulties rolling onto his feet when laid on its back. |
| 3 | Ataxia | Wobbly walk - when the mouse walks the hind legs are unsteady. |
| 4 | Early paralysis | The mouse has difficulties standing on its hind legs, but still has remnants of movement. |
| 5 | Full paralysis | The mouse can't move its legs at all, it looks thinner and emaciated. |
| 6 | Moribund/Death | |

As shown in FIG. 7, treatment with 3D2 resulted in an amelioration of disease. Each data point represents a mean of scores taken from 9 mice. Group means (GMS) were compared by using one-way ANOVA followed by Bonferroni's multiple comparison post test. Statistically significant differences were observed between the control group (mouse IgG) and each 3D2 treated group (P<0.05), but not between two 3D2 treated groups (P>0.05). The disease attenuation was observed even when treatment did not begin until mice had demonstrated active disease (Group C).

RR-EAE-2: 3D2 effect on relapsing-remitting EAE in SJL mice. A second study ("RR-EAE-2") was done using pertussis toxin in the induction protocol to test 3D2 in a more severe disease model. For this second relapsing-remitting EAE study, SJL/J mice were subcutaneously immunized with $PLP_{139-151}$ in 1 mg/ml CFA enhanced with 5 mg of heat-inactivated *Mycobacterium tuberculosis* strain H37RA, and one-hundred nanograms of *Pertussis* toxin *was administered intraperitonealy on Days* 0 and 2 post-immunization. Treatment included bi-weekly intraperitoneal injections of 0.3 mg (15 mg/kg) antibody separated into the following groups:

A. Control (mouse IgG) starting at Day 0

B. 3D2 starting at Day 0

C. 3D2 starting at Day 7

D. 3D2 starting at EAE onset (score ≥2)

The results for RR-EAE-2 are shown in FIG. 8. Each data point represents a mean of scores taken from 9 mice. Group means were compared by using one-way ANOVA followed by Bonferroni's multiple comparison post test. Statistically significant differences were observed between control (mouse IgG) and each 3D2 treated group (P<0.05), but not among the three 3D2 treated groups (P>0.05). Again, treatment with 3D2 had a statistically significant effect on the severity of the disease, even when the treatment was started at the onset of the EAE symptoms, score ≥2 (Group D).

Example 5

Evaluation of Anti-CXCL13 Antibodies in Mouse Disease Model for Lupus

Murine model of Systemic Lupus Erythematosus (SLE). SLE is an autoimmune disease that involves multiple organs and is characterized by the spontaneous formation of ectopic germinal centers and autoantibody production against a number of nuclear antigens. The effect of anti-CXCL13 3D2 antibody was tested in a murine model of lupus. Lupus-prone New Zealand Black X New Zealand White F1 (NZB/NZWF1) mice spontaneously develop high-titer anti-dsDNA antibodies and severe proliferative glomerulonephritis caused by formation of immune complexes in glomeruli of the kidneys.

SLE-1: Treatment of advanced disease. In study "SLE-1," treatment started in twenty-four to thirty-week old NZB/NZWF1 mice with proteinuria of ≥2 (proteinuria scoring system is described in Table 4 below) and the treatment was continued for eight weeks. The treatment included bi-weekly intraperitoneal injections of 0.3 mg (15 mg/kg) of 3D2 or mouse IgG (control).

TABLE 4

Proteinuria Scores

| Proteinuria score | [Protein] in urine, mg/dl |
|---|---|
| 1+ | 30 |
| 2+ | 100 |
| 3+ | 300 |

As shown in FIG. 9A, treatment with 3D2 halted progression of proteinuria. Histological analysis of kidneys using a well-defined scoring system (Table 5) also showed a beneficial effect of anti-CXCL13 treatment as the glomerulonephritis (GN), interstitual nephritis (IN), and vasculitis (VI) pathology scores were lower in the 3D2-treated group compared to control (mouse IgG). See FIG. 9B.

TABLE 5

Kidney Pathology Scores

| Scores | Glomerulonephritis | Interstitial Nephritis | Vessels |
|---|---|---|---|
| 0-1+ | Focal, mild or early proliferative | Occasional, focal or small pockets of MNC (10-15 cells) | Occasional perivascular infiltrate |
| 1-2+ | Moderate or definite proliferative; increased matrix | Focal infiltrates (15-30 cells) | Several foci of perivascular infiltrate; no necrosis |
| 2-3+ | Diffuse and focal or diffuse proliferative | Multifocal extensive infiltrates; with necrosis | Multifocal perivascular; more extensive; +/− necrosis (3+) |
| 3-4+ | Severe diffuse proliferative, with crescent/sclerosis | Severe disease with extensive necrosis | Multifocal or diffuse; extensive with necrosis |

For proteinurea scores (FIG. 9A) and kidney pathology scores (FIG. 9B), each data point represented the mean of ten measurements. No statistically significant differences were observed (P>0.05) in two-way ANOVA followed by Bonferroni's multiple comparison post test to identify statistically significant differences (P<0.05).

SLE-2: Prevention Trial in Mice with Early Disease (post-autoantibody induction, but before significant proteinuria). In study "SLE-2," the treatment started in twenty-week-old NZB/NZWF1 mice and continued for twelve weeks. The treatment included bi-weekly intraperitoneal injections of 0.3 mg (15 mg/kg) of either 3D2 or mouse IgG (control). As shown in FIG. 10A, treatment with 3D2 resulted in statistically significant inhibition of the progression of proteinuria, particularly during the first eight weeks of treatment. After eight weeks, zero out of seven (0%) mice in the 3D2 treatment group and four out of nine (44%) mice in the control group had >2+ proteinuria score. At the end of twelve weeks of treatment, mean urine protein was 2.1+/−0.2 with 3D2 treatment vs. 3.1+/−0.15 with mouse IgG (control) antibody.

Kidney pathology scores were also measured in mice from the 3D2-treated group and mouse IgG-treated group. A summary of the glomerulonephritis (GN) and interstitual nephritis (IN) pathology scores is shown in FIG. 10B.

Proteinuria levels (FIG. 10A) and kidney pathology scores (FIG. 10B) were measured in 7 mice from 3D2-treated group and 9 mice from mouse IgG-treated group. Proteinurea scores were significantly different between groups (P=0.0042; two-way ANOVA with Bonferroni's multiple comparison test). Kidney pathology scores were not significantly different (P>0.05). Although, mean pathology scores were not significantly different, there was histologic evidence of severe kidney disease in two out of seven (29%) mice in the 3D2 treatment group, while four out of nine (44%) mice in the control group showed evidence of severe disease. It was noted that blockade of CXCL13 by 3D2 did not prevent the development of autoantibodies (data not shown).

The effect of 3D2 treatment on the number of Germinal Centers (GC) and primary follicles in the spleen of lupus mice was evaluated. Spleen sections were stained with GL-7 (GC stain), B220 antibody (B cell marker), or antibody against follicular dendritic cells (FDCs) from 3D2-treated and mouse IgG-treated (control) NZB/NZWF1 mice. The effect of CXCL13 inhibition on splenic lymphoid architecture is shown in FIGS. 11A-B. The primary follicles remained intact. Mice treated with 3D2 exhibited a significant decrease in size and frequency of spontaneous germinal centers (GC) in the spleen. Mice treated with 3D2 ("tx") showed a trend towards decreased numbers of GCs when expressed as a ratio of primary:secondary (GC) follicles (p=0.19) (FIG. 12A) and a significant decrease in GC size (p=0.03) (FIG. 12B). Values are shown as mean+/−SEM with 5 mice per group.

The above described SLE results shows that CXCL13 inhibition by 3D2 antibody leads to decreased nephritis in the NZB/NZWF1 mouse model of lupus, particularly at earlier stages of disease, and may affect splenic architecture.

Example 6

Preparation of Chimeric and Humanized Anti-CXCL13 Monoclonal Antibodies

Isolation of 3D2 hybridoma V genes and cloning of chimeric 3D2 antibody. Mouse 3D2 antibody was used as a prototype for generation of a chimeric anti-CXCL13 monoclonal antibody. The variable (V) genes were isolated from a 3D2 hybridoma using standard methods. The polynucleotide and amino acid sequences of the heavy chain (H1609) and the light chain (L0293) of 3D2 are shown in FIG. 13. The VH and VK complementarity determining regions (CDRs) are underlined (SEQ ID NOs: 4, 5, 6, 9, 10, and 11, respectively).

The variable heavy (VH) gene was cloned into a mammalian expression vector that contained the human gamma 1 heavy chain gene, creating a full length chimeric heavy chain. The variable light (VK) gene was cloned into a mammalian expression vector that had the human Kappa constant gene, creating a full length chimeric light chain. In order to make the chimeric antibody, the expression vectors containing the chimeric heavy chain and the chimeric light chain were co-transfected into CHO-S cells. The monoclonal antibody (MAb) that was produced was secreted from the cells and harvested after a 3- to 6-day expression period. The resulting MAb was purified using Protein A chromatography and characterized. The resulting chimeric IgG1 antibody ("MAb 1476") was shown to be specific for human and mouse CXCL13 by ELISA, was shown to have similar affinity on mouse and human CXCL13, and was shown to have similar functional activity as the parental mouse antibody, 3D2 (data not shown). Furthermore, MAb 1476 was able to compete with biotinylated 3D2 and 3C9 for binding on mouse and human CXCL13 in an Epitope Competition ELISA (data not shown).

Humanization of chimeric 3D2 (MAb 1476). Humanization of chimeric 3D2 antibody is summarized below. The modifications that were introduced to framework regions (FWR) of heavy (H1609) and light chains (L0293) from the chimeric MAb 1476 are shown in FIGS. 14A and 14B, respectively. A putative N-linked glycosylation site (Asn-Leu-Thr) in H1609 was replaced with Ser-Leu-Thr (FIG. 14A). The mutation did not affect antibody affinity (see Table 6) and resulted in generation of "MAb 5080." In order to improve affinity and functionality of MAb 5080, a number of variable region mutants were produced and screened by IC50 ELISA on human CXCL13. A single Serine (S) to Methionine (M) mutation at position 31 in the L5055-CDR1 as well as changes to the light chain framework region (see FIGS. 14B and 15) resulted in generation of "MAb 5261," which demonstrated a significant improvement in affinity compared to 3D2 and MAb 5080 (Table 6). A comparison of the amino acid sequences of H1609 (SEQ ID NO: 3) and H2177 (SEQ ID NO: 13) is shown in FIG. 14A, and a comparison of L0293 (SEQ ID NO: 8), L5055 (SEQ ID NO: 17), and L5140 (SEQ ID NO: 15) is shown in FIG. 14B.

TABLE 6

Antibody affinity for recombinant human and mouse CXCL13

| Antibody | Fc | Heavy Chain (VH) | Light Chain (VK) | Affinity (Biacore), nM | |
|---|---|---|---|---|---|
| | | | | Human CXCL13 | Mouse CXCL13 |
| 3D2 | Mouse IgG1 | H1609 | L0293 | 13 | 159 |
| MAb 1476 (chimeric 3D2) | Human IgG1 | H1609 | L0293 | 11.4 | NA |
| MAb 5080 | Human IgG1 | H2177 | L5055 | 14.5 | 59.2 |
| MAb 5261 (affinity improved MAb 5080) | Human IgG1 | H2177 | L5140 (L5055 M31a) | 5.1 | 8.1 |

The polynucleotide and amino acid sequences of MAb 5080 VH and VK: H2177 (Amino Acid SEQ ID NO: 13) and L5055 (Amino Acid SEQ ID NO: 17), respectively; and MAb 5261 VH and VK: H2177 (Amino Acid SEQ ID NO: 13) and L5140 (Amino Acid SEQ ID NO: 15), respectively, are shown in FIG. 15.

MAb 5261 specificity for CXCL13: Similar to 3D2, specificity of MAb 5261 was assessed by specificity ELISA and Capture Epitope Competition ELISA on a panel that included recombinant chemokines (recombinant mouse, human, and cynomolgus monkey CXCL13, human IL-8/CXCL8; human IP-10/CXCL10, human MIG/CXCL9 and human SDF-1alpha/CXCL12); native human and mouse CXCL13; and various non-specific antigens (recombinant human C35, streptavidin, bovine serum albumin (BSA), human serum albumin (HAS), insulin, and hemoglobin).

For specificity ELISA, recombinant human, cynomolgus monkey, and mouse CXCL13 were each coated at 100 nM. MAb 5261 demonstrated multi-species specificity to CXCL13 (FIGS. 16A-C). The binding of MAb 5261 on recombinant human (FIG. 16A) and cynomolgus monkey CXCL13 (FIG. 16B) was comparable to the binding of its direct "parent", MAb 5080, and stronger than the binding of MAb 1476 (chimeric 3D2). MAb 5261 was significantly superior in binding on recombinant mouse CXCL13 compared to both MAb 1476 and MAb 5080 (FIG. 16C). The data points for each chemokine represents the mean of triplicate measurements. EC50 values were calculated from four-parameter sigmoidal curve fit ($R^2$ for the curves that produced EC50 values were 0.99).

MAb 5261 binding to native human and mouse CXCL13 was determined by Capture Epitope Competition ELISA. For human ELISA, human CXCL13 (1:4 dilution of THP1 supernatant or 0.097 nM) was captured with 6.6 nM MAb 801 and detected with 0.66 nM biotin-3C9. For mouse ELISA, mouse CXCL13 (1:40 dilution of TNF-Tg organ extract) was captured with 33 nM MAb 470 and detected with 3.3 nM biotin-3D2. Each data point represents an average of duplicate measurements from one of at least three independent experiments. When tested in Capture Epitope Competition ELISA on native human (FIG. 17A) and mouse CXCL13 (FIG. 17B), MAb 5261 demonstrated superiority to both 3D2 and 5080 antibodies for binding to both human and mouse native CXCL13. Curves shown in FIGS. 17A-B were fitted using four-parameter sigmoidal curve fit ($R^2$=0.99).

Example 7

Functional Characterization of Anti-CXCL13 MAb 5261

Inhibition of human and mouse B-cell migration. The ability of MAb 5261 to inhibit human CXCL13-induced human B-cell chemotaxis was tested on both the stable cell line human pre-B-697-hCXCR5 and primary human tonsillar cells.

MAb 5261 inhibition of human CXCL13-induced human B-cell chemotaxis on stable cell line human pre-B-697-hCXCR5 was tested using the protocol is described in Example 2 above. The human pre-B-697-hCXCR5 cell migration inhibition by MAb 5261 is shown in FIG. 18A. For the human primary tonsillar cell studies, the tonsillar cells were obtained by the mechanical dissociation of the tissue. Cells ($10^6$/upper chamber of 5-μm Transwell plate) were allowed to migrate towards 5 μg/ml human CXCL13 for 2 hours at 37° C.). Inhibition of human primary tonsillar cell migration by MAb 5261 is shown in FIG. 18B. The results shown in FIGS. 18A-B represent an average of triplicate measurements+/−SEM from one of at least three experiments. Curves were fitted using four-parameter sigmoidal curve fit (R2=0.98-0.99).

The effect of MAb 5261 on mouse CXCL13-mediated mouse B-cell chemotaxis was evaluated on mouse splenocytes from C57Black/6 and SJL/J mice as described in Example 2 above. Again, migration towards human or murine SDF-1α (0.1 μg/ml) was used as a negative control to ensure CXCL13 specificity of the antibody effect (data not shown). The splenocyte migration inhibition by MAb 5261 is shown in FIG. 19 (the data from representative experiments are shown as mean of duplicate measurements+/−SD). Migration inhibition values were calculated based on the values obtained with corresponding Isotype controls.

As shown in FIGS. 18 and 19, MAb 5261 inhibited both human and mouse CXCL13-dependent chemotaxis. The differences in EC50 values between cultured and primary cells (see FIG. 18) could likely be attributed to differences in human CXCL13 concentrations, e.g., 97 nM (1 μg/ml) was used in human pre-B-697-hCXCR5 cell migration and 485 nM (5 μg/ml) was used in human tonsillar cell migration.

Inhibition of human CXCL13-mediated endocytosis of human CXCR5 receptor. This experiment was done using human pre-B-697-hCXCR5 cells treated with human CXCL13 to induce endocytosis of human CXCR5 receptor according to the methods described above in Example 3. The amount of human CXCL13 was 2 μM, which was higher than the amount used in the 3D2 endocytosis assay (i.e., 0.485 μM) shown in Example 3, thus differences in EC50 values were observed. Inhibition of CXCR5 receptor endocytosis by MAb 5261 is shown in FIG. 20. The results are shown as an average of triplicate measurements from one of at least three independent experiments. The curve was fitted using four-parameter sigmoidal curve fit (R2=0.99).

Example 8

Generation and Characterization of a Murine Version of Anti-CXCL13 MAb 5261

MAb 5261 contains human heavy and light variable regions and human IgGamma1-F allotype as well as human kappa. A murine counterpart ("MAb 5378") was engineered with mouse IgG2a (Gamma 2a chain). IgG2a isotype has close similarities to human IgG1, including the ability to fix complement and bind to Fc receptor. MAb 5378 contains the same human heavy and light chain variable genes as MAb 5261 along with mouse IgG2a constant and mouse kappa, respectively.

A common restriction site among the heavy and light chain expression plasmids was used to allow for the changing of isotypes. Generation of the isotype species was achieved through restriction digestion, ligation, and transformation. Specifically, for the MAb 5261 heavy chain, the variable region of the gene was digested with restriction endonucleases and ligated into comparable sites in an expression plasmid that contained the mouse IgG2a constant region in order to make the heavy chain for MAb 5378 (H5188). Similarly, for the MAb 5261 light chain, the variable region of the gene was digested with restriction endonucleases and ligated into comparable sites in an expression plasmid that contains the mouse IgKappa constant region to make the light chain for MAb 5378 (L5153). The polypeptide and amino acid sequences of the variable regions of MAb 5378 light and heavy chains are identical to MAb 5261 and are shown in FIG. 21. The VH and VK complementarity determining regions (CDRs) are underlined (SEQ ID NOs: 4, 5, 6, 16, 10, and 11, respectively).

MAb 5378 affinity measurements. Affinity measurements of MAb 5378 for recombinant human and mouse CXCL13 were measured by BIACORE® using methods similar to those described in Example 1. Mab 5378 affinity for recombinant human and mouse CXCL13 was compared to MAb 5261 and 3D2. As shown in Table 7, the affinity measurements (nM) of MAb 5261 and MAb 5378 for both human and mouse chemokines were significantly improved compared to the 3D2.

TABLE 7

Affinities of 5261, 5378, and 3D2 for recombinant human and mouse CXCL13

| | | Affinity, nM | |
|---|---|---|---|
| Antibody | Fc | Human CXCL13 | Mouse CXCL13 |
| 5261 | Human IgG1 | 5.1 | 8.1 |
| 5378 | Mouse IgG2a | 4.5 | 4.2 |
| 3D2 | Mouse IgG1 | 13 | 159 |

MAb 5378 epitope mapping. An Epitope Competition ELISA experiment was performed to determine if MAb 5378 shared a binding epitope on mouse CXCL13 with MAb 5261. Recombinant mouse CXCL13 was captured on the plate with 1 µg/ml of MAb 470, 5378 or 5261 (control). Antibody/chemokine interactions were detected with 0.5 µg/ml (3.3 nM) of biotinylated MAb 5261 followed by Streptavidin-HRP. Commercial rat anti-mouse antibody MAb 470 was also included into the study. The ability of mouse CXCL13, pre-incubated with either MAbs 470 or 5378, to bind biotinylated MAb 5261 was evaluated using Epitope Competition ELISA. It was shown (FIG. 22), that MAb 5378 shared a mouse CXCL13 binding epitope with MAb 5261, but not with MAb 470. Thus, MAb 5378 was shown to retain epitope binding and affinity, which was needed in order for MAb 5378 to be used as a surrogate for MAb 5261 in animal model studies. Furthermore, the epitope binding results described throughout the Examples can be summarized as showing that 3D2, 3C9, MAb 1476, MAb 5080, MAb 5261, and MAb 5378 all bind the same epitope of human CXCL13.

MAb 5378 specificity for CXCL13. Specificity of MAb 5378 was evaluated on recombinant human, mouse and cynomolgus monkey CXCL13 (FIG. 23) and a panel of recombinant chemokines and various antigens (recombinant chemokines (mouse, human and cynomolgus monkey CXCL13, human IL-8/CXCL8, human IP-10/CXCL10, human MIG/CXCL9, and human SDF-1alpha/CXCL12); native human and mouse CCL13; and various non-specific antigens (recombinant human C35, streptavidin, bovine serum albumin (BSA), human serum albumin (HAS), insulin, hemoglobin) (data not shown). Specificity ELISA was performed as described in Example 1. In particular, each chemokine was coated at 100 nM. As shown in FIG. 23, MAb 5378 was compared to mouse antibody 3D2 and control (mouse IgG). MAb 5378 was superior to 3D2, to varying degree, in binding to the chemokines from all three species. The most significant differences in binding were observed on mouse CXCL13 showing the potential advantage of MAb 5378 over 3D2 in animal studies. Each data point represents mean of triplicate measurements. EC50 values were calculated from four-parameter sigmoidal curve fit ($R^2$ for the curves that produced EC50 values were 0.99).

Inhibition of human and mouse B-cell migration was tested for MAb 5378. Ability of MAb 5378 to interfere with CXCL13-dependent chemotaxis of mouse and human B-cells was tested in migration assays involving cultured (human pre-B-697-hCXCR5 cells; FIG. 24A) and primary (human tonsillar cells; FIG. 24B) human cells as well as mouse spleenocytes (FIG. 24C) using the methods described in Examples 2, 7, and 2 respectively. The chemokine concentrations were: 97 nM of huCXCL13 for human pre-B-697-huCXCR5 migration; 485 nM of huCXCL13 for human tonsillar cell migration; and 500 nM of muCXCL13 for mouse spleenocyte migration. Migration towards human or murine SDF-1 alpha was used as a negative control (not shown). Migration inhibition values were calculated based on the values obtained with corresponding Isotype Controls. The results shown in FIGS. 24A-C represent an average of triplicate measurements+/−SEM from one of at least three experiments. Curves were fitted using four-parameter sigmoidal curve fit ($R^2$=0.99). In the human migration assays, MAb 5378 was compared to MAb 5261, and in the mouse migration assays, MAb 5378 was compared to 3D2. In both cases, MAb 5378 successfully inhibited CXCL13-induced human and mouse cell migration to a degree comparable to MAb 5261 and slightly superior to 3D2.

Inhibition of human CXCL13-mediated endocytosis of human CXCR5 receptor. MAb 5378 was compared to its prototype MAb 5261 and mouse anti-human CXCL13 antibody 3D2 in a human CXCL13-mediated human CXCR5 receptor internalization assay using the methods described in Example 3. As shown in FIG. 25, MAb 5378 was identical to MAb 5261 and significantly superior to 3D2 in its ability to inhibit human CXCR5 receptor internalization. The data points for MAb 5261 and MAb 5378 represent average of measurements from two independent experiments. Data points for 3D2 and Isotype Controls represent average of triplicate measurements from a single experiment. Curve was fitted using four-parameter sigmoidal curve fit ($R^2$=0.99).

Example 9

Evaluation of Anti-CXCL13 Antibodies in Mouse Disease Model for Rheumatoid Arthritis Murine Model of Rheumatoid Arthritis. Collagen-induced arthritis (CIA) in mice and rats is a well-established model of human Rheumatoid arthritis (RA). The disease is typically induced by intradermal injection of bovine type II collagen emulsified in Complete Freund's Adjuvant (CFA) and is characterized by production of mouse collagen antibodies and, subsequently, progressive development of arthritis in the paws.

CIA-1: Anti-arthritic efficacy of MAb 5378 in CIA model using DBA1/J mice. The disease was induced in DBA1/J mice by subcutaneous immunization with 100 µg of bovine type II collagen in CFA enhanced with 100 µg of heat-killed *M. tuberculosis* H37Ra, followed by boost immunization on Day 21 with 100 µg of bovine type II collagen in Incomplete Freunds' Adjuvant (IFA). The animals were scored for macroscopic signs of arthritis (see Table 8) three times weekly and the Arthritic Index (AI) was calculated by addition of individual paw scores (the maximum arthritic index that could be achieved in any given animal was 16).

TABLE 8

Macroscopic signs of CIA in mice

| Arthritic Score | Description |
|---|---|
| 0 | No visible effects of arthritis |
| 1 | Edema and/or erythema of 1 digit |
| 2 | Edema and/or erythema of 2 digits |
| 3 | Edema and/or erythema of more than 2 digits |
| 4 | Severe arthritis of entire paw and digits |

Prophylactic treatment started one day before boost immunization, i.e., on Day 20 postinduction in animals with low AI of 2-6, and consisted of the following treatment groups (10 mice per group):
A. Mouse IgG Isotype (control)
B. MAb 5378
C. etenercept (TNF inhibitor; positive control)

The mice had been given either intraperitoneal (Mouse IgG and MAb 5378) or subcutaneous (etenercept) injections of 0.6 mg (30 mg/kg) of antibody twice a week for three weeks. The study was terminated on Day 41 postinduction.

As shown in FIG. 26 prophylactic treatment with MAb 5378 resulted in a decreased rate of disease development and significant inhibition of disease severity, which became evident at the study endpoint. Statistically significant differences were observed at the study endpoint (Day 41) between Mouse IgG and MAb 5378 treated groups ($P<0.05$) and Mouse IgG and etenercept treated groups ($P<0.05$). The inhibitory effect of MAb 5378 was not statistically different from the inhibitory effect of positive control agent etenercept (P>0.05).

CIA-2: Anti-arthritic efficacy of MAb 5378 in CIA model in DBA1/J mice. A second CIA study with MAb 5378, "CIA-2," was performed. In this study, the disease was induced in DBA1/J mice as described above for CIA-1. Again, prophylactic treatment started one day before boost immunization, on Day 20 postinductions in animals with low AI of 2-6. In addition to etenercept, commercial rat anti-murine CXCL13 antibody MAb 470 was used as a control. The study therefore included the following groups:
A. Mouse IgG Isotype control
B. MAb 5378
C. etenercept (TNF inhibitor; positive control)
D. MAb 470

The mice were given either intraperitoneal (Mouse IgG, MAb 470 and MAb 5378) or subcutaneous (etenercept) injections of 0.6 mg (30 mg/kg) of antibody twice a week for three weeks. The study was terminated on Day 42 postinduction.

As evident from FIG. 27, prophylactic treatment with MAb 5378 again resulted in a decreased rate of disease development and significant inhibition of disease severity throughout the study as well as at the endpoint (Day 42). Statistically significant differences were observed between Mouse IgG and MAb 5378 treated groups (P<0.05) and Mouse IgG and MAb 470 treated groups (P<0.05). The inhibitory effect of MAb 5378 was not statistically different from the inhibitory effects of positive control agent etenercept and rat anti-murine CXCL13 antibody MAb 470 (P>0.05).

GC-1: Effect of MAb 5378 on germinal center formation in immunized BALB/c mice. Given the successful performance of our anti-CXCL13 antibodies in animal models of autoimmunity, the possible mechanism of action involving disruption of ectopic germinal center formation was tested. Germinal centers in MAb 5378-treated BALB/C mice immunized with 100 μg 4-hydroxy-3-nitrophenylacetyl-chicken-g-globulin (NP-CGG) precipitated in 100 ul of alum were examined. The animals were injected intraperitoneally with total of 0.6 mg (30 mg/kg) a week of either Mouse isotype control (0.6-mg weekly injections) or MAb 5378 (0.3-mg bi-weekly injections). The injections started one week before and continued through one week after NP-GCC immunization. Germinal center formation was evaluated on day 10 post-challenge. Single cell suspensions from spleens and lymph nodes were analyzed by flow cytometry for the presence of various B-cell (activated GC B-cells; follicular and marginal zone B-cells) and T-cell (CD4+ and CD8+) subsets. Although MAb 5378 produced no effect on T-cells or follicular and marginal zone B-cells (data not shown), germinal center B-cells (B220+/CD38low/PNA+) were reduced in spleens and lymph nodes by 43% and 41%, respectively (FIG. 28). Spleen group means were compared by using unpaired student t-test. The reduction in GC-B cells was statistically significant in MAb 5378-treated spleens compared to Mouse IgG treated group (P<0.05). The cells recovered from lymph nodes were very low in numbers and therefore were pooled (as a result, no statistical analysis was performed with the data from the lymph nodes).

Example 10

Evaluation of Anti-CXCL13 Antibodies in Mouse Model for *Helicobacter* Infection Murine Model of *Helicobacter* infection. *Heliobacter* species such as *H. heilmannii* and *H. Pylori* induce gastric MALT lymphoma in patients. A mouse model of *Heliobacter* induced gastric lymphoid follicles was described in Nobutani et al., *FEMS Immunol Med Microbiol* 60:156-164 (2010), which is incorporated herein by reference in its entirety. The Nobutani et al. mouse model was used herein to test the effect of anti-CXCL13 antibody in reducing gastric lymphoid follicles. The treatment schedule for *H. heilmannii* infection of mice and antibody administration used in this Example is shown in FIG. 29.

In particular, C57BL/6J mice were infected with *H. heilmannii*. Starting one-week post-infection, the mice were administered either Isotype antibody control or anti-CXCL13 antibody (MAb 5378) weekly for twelve weeks. Anti-CXCL13 MAb 5378 (a mouse IgG2a isotype) was formulated in PBS, pH 7.2 at 3 mg/ml. Mice were injected with 200 microliters (600 micrograms) intraperitoneally starting day 7 post-infection and weekly thereafter. The Isotype control was an independent monoclonal mouse IgG2a antibody.

Gastric samples from the mice were evaluated by PCR for expression of *H. heilmannii* specific 16s rRNA genes to confirm infection. PCR amplification reactions involved 1× reaction buffer [20 mM Tris/HCl (pH8.0), 100 mM KCl, 0.1 mM EDTA, 1 mM DTT, 0.5% Tween-20, 0.5% Nonidet P40, and 50% glycerol] containing 1 unit of Taq DNA polymerase (TOYOBO, Osaka, Japan); 10 nmols of each deoxynucleotide triphosphate; 10 pmols of each oligonucleotide primer; and 1 μl of the diluted DNA, which was prepared by 1:10 dilution of the original samples with a DNA concentration of approximately 20-100 ng/μl, in a final volume of 50 μl. Cycling conditions for the 16s rRNA reactions involved 35 cycles of 94° C. for 30 seconds, 56° C. for 30 seconds, and 72° C. for 30 seconds.

The *H. heilmannil* specific 16s rRNA gene PCR primers are shown below:
F: 5'-TTGGGAGGCTTTGTCTTTCCA-3' (SEQ ID NO: 24)
R: 5'-GATTAGCTCTGCCTCGCGGCT-3' (SEQ ID NO: 25)

The results for expression of *H. heilmannil* specific 16s rRNA genes amplified in all gastric samples obtained from *H. heilmannil* infected mice are shown in FIG. 30. These results show that all of the treated mice were positive for *H. heilmannil* infection.

CXCL13 expression in gastric mucosa of *Helicobacter* infected mice. The mRNA expression levels of CXCL13 in the gastric mucosa of *H. heilmannil* infected and noninfected mice was determined by real-time quantitative PCR. The mRNA expression of CXCL13 in the gastric mucosa of *H. heilmannil* infected mice compared to noninfected wild-type control mice one month and three months after infection is shown in FIGS. 31A and 31B, respectively. These results show an increase in CXCL13 expression in *H. heilmannil* infected mice.

CXCL13 expression in gastric mucosa of antibody treated *Helicobacter* infected mice. The mRNA expression levels of CXCL13 in the gastric mucosa of *H. heilmannil* infected mice after treatment with Isotype control or anti-CXCL13 antibody was determined by reverse transcription PCR. The mucosal and submucosal layers of the stomach were removed from the muscularis and serosa, and then homogenized with 1 ml of TRIZOL Regent (Invitrogen). RNA was extracted from the homogenates according to the manufacturer's instructions. RNA was subjected to the reverse transcription reaction using a High Capacity cDNA Reverse Transcription Kit (Applied Biosystems, Foster City, Calif.) according to the manufacturer's protocol. PCR amplification reactions involved 1× reaction buffer [20 mM Tris/HCl (pH8.0), 100 mM KCl, 0.1 mM EDTA, 1 mM DTT, 0.5% Tween-20, 0.5% Nonidet P40, and 50% glycerol] containing 1 unit of Taq DNA polymerase (TOYOBO, Osaka, Japan); 10 nmols of each deoxynucleotide triphosphate 10 pmols of each oligonucleotide primer; and 1 µl of the diluted DNA, which was prepared by 1:10 dilution of the original samples with a DNA concentration of approximately 100 ng/µl, in a final volume of 50 µl. Cycling conditions for the CXCL13 and β-actin reactions involved 94° C. for 2 min, 35 cycles of 94° C. for 30 seconds, 55° C. for 30 seconds, and 72° C. for 1 min.

FIG. 32 shows expression of CXCL13 and β-actin control mRNA in the stomach of H. heilmannil infected mice after Isotype control or anti-CXCL13 antibody treatment. These results show that CXCL13 was not expressed in noninfected wild-type mice but was expressed in all H. heilmannil infected mice.

Anti-CXCL13 antibody treatment reduces gastric lymphoid follicles in Helicobacter infected mice. The stomachs of mice three months after H. heilmannil infection were resected and opened at the greater curvature. Half of the stomach was embedded in paraffin wax, and the paraffin-embedded tissues were sliced and stained with hematoxylin and eosin (H&E). FIG. 33 shows H&E stained images of stomach from the Isotype control (left panel) and anti-CXCL13 antibody (right panel) treated mice. The number of gastric lymphoid follicles were counted for Isotype control and anti-CXCL13 antibody samples. The results are depicted in the lower panel of FIG. 33. These results show a reduction in gastric follicles in H. heilmannil infected mice treated with anti-CXCL13 antibody relative to control treatment.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments but should be defined only in accordance with the following claims and their equivalents.

What is claimed is:

1. A method for treating an autoimmune disease or an inflammatory disease, comprising administering to a mammal in need of treatment an isolated antibody or antigen-binding fragment thereof that specifically binds to human, murine and cynomolgus monkey CXCL13, wherein the antibody or antigen-binding fragment comprises a heavy chain variable region (VH) and a light chain variable region (VL), wherein the VH comprises the three complementarity determining regions HCDR1, HCDR2, HCDR3 of SEQ ID NO: 4, SEQ ID NO: 5, and SEA ID NO:6, respectively, and wherein the VL comprises the LCDR1, LCDR2, and LCDR3 regions of SEQ ID NO: 9, SEQ ID NO: 10, and SEQ ID NO: 11, respectively, or the LCDR1, LCDR2, and LCDR3 regions of SEQ ID NO: 16, SEQ ID NO: 10, and SEQ ID NO: 11, respectively, wherein the autoimmune disease or inflammatory disease is multiple sclerosis (MS), Systemic Lupus Erythematosis (SLE) or arthritis or wherein the inflammatory disease is associated with a *Helicobacter* bacterial infection.

2. The method of claim 1, wherein the autoimmune disease or the inflammatory disease is Systemic Lupus Erythematosis (SLE).

3. The method of claim 1, wherein the autoimmune or inflammatory disease is rheumatoid arthritis or MS.

4. A method of treating cancer in a subject having a cancer selected from leukemia, lymphoma, mucosa-associated lymphoid tissue (MALT) lymphoma, colon, pancreatic, prostate, stomach, esophageal, and breast cancer, comprising administering to the subject an isolated antibody or antigen-binding fragment thereof that specifically binds to human, murine and cynomolgus monkey CXCL13, wherein the antibody or antigen-binding fragment comprises a heavy chain variable region (VH) and a light chain variable region (VL), wherein the VH comprises the three complementarity determining regions HCDR1, HCDR2, HCDR3 of SEQ ID NO: 4, SEQ ID NO. 5, and SEA ID NO:6, respectively, and wherein the VL comprises the LCDR1, LCDR2, and LCDR3 regions of SEQ ID NO: 9, SEQ ID NO: 10, and SEQ ID NO: 11, respectively, or the LCDR1, LCDR2, and LCDR3 regions of SEQ ID NO: 16, SEQ ID NO: 10, and SEQ ID NO: 11, respectively.

5. The method of claim 1, wherein the inflammatory disease associated with a *Helicobacter* bacterial infection is MALT lymphoma, gastric cancer, gastric or duodenal ulcer, gastritis, or a gastric lesion.

6. The method of claim 5, wherein the gastric cancer is esophageal or stomach cancer.

7. The method of claim 1, wherein the mammal is a human.

8. A method for inhibiting gastric lymphoid follicles or treating a gastric or duodenal ulcer in a mammal infected with a *Helicobacter* bacterium, comprising administering to the mammal an isolated antibody or antigen-binding fragment thereof that specifically binds to human, murine and cynomolgus monkey CXCL13, wherein the antibody or antigen-binding fragment comprises a heavy chain variable region (VH) and a light chain variable region (VL), wherein the VH comprises the three complementarity determining regions HCDRI, HCDR2, HCDR3 of SEQ ID NO: 4, SEQ ID NO. 5, and SEA ID NO:6, respectively, and wherein the VL comprises the LCDRI, LCDR2, and LCDR3 regions of SEQ ID NO: 9, SEQ ID NO: 10, and SEQ ID NO: 11, respectively, or the LCDRI, LCDR2, and LCDR3 regions of SEQ ID NO: 16, SEQ ID NO: 10, and SEQ ID NO: 11, respectively.

9. The method of claim 8 wherein the *Helicobacter* bacterium is *H. pylori* or *H. heilmannii*.

10. The method of claim 8, wherein the mammal is a human.

11. The method of claim 3, wherein the autoimmune disease is MS.

12. The method of claim 11, wherein the treatment decreases symptoms associated with the MS.

* * * * *

SEQUENCE LISTING

```
<160> NUMBER OF SEQ ID NOS: 25

<210> SEQ ID NO 1
<211> LENGTH: 13
<212> TYPE: PRT
<213> ORGANISM: Artificial Sequence
<220> FEATURE:
<223> OTHER INFORMATION: PLP139-151

<400> SEQUENCE: 1

His Ser Leu Gly Lys Trp Leu Gly His Pro Asp Lys Phe
1               5                   10

<210> SEQ ID NO 2
<211> LENGTH: 369
<212> TYPE: DNA
<213> ORGANISM: Artificial Sequence
<220> FEATURE:
<223> OTHER INFORMATION: H1609

<400> SEQUENCE: 2
gaggtgcagc ttcaggagtc tggccctggg atattgcagc cctcccagac cctcaatctg      60
acttgttctt tctctggatt ttcactgagc acttttggta tgggtgtagg ctggattcgt     120
cagccttcag ggaagggtct ggagtggctg gcacacattt ggtgggatga tgataggagg     180
tataacccag ccctgaagag tcggctcaca atctccaagg aaacctccaa aaaccaggtg     240
ttcctcaaga tcgccaatgt ggacactgca gatactgcca catactactg tactcgaata     300
gcggggtatt atggtagtag agactggttt gcttactggg gccaagggac cacggtcacc     360
gtctcctca                                                              369

<210> SEQ ID NO 3
<211> LENGTH: 123
<212> TYPE: PRT
<213> ORGANISM: Artificial Sequence
<220> FEATURE:
<223> OTHER INFORMATION: H1609
```

<400> SEQUENCE: 3

Glu Val Gln Leu Gln Glu Ser Gly Pro Gly Ile Leu Gln Pro Ser Gln
1               5                   10                  15

Thr Leu Asn Leu Thr Cys Ser Phe Ser Gly Phe Ser Leu Ser Thr Phe
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Arg Arg Tyr Asn Pro Ala
    50                  55                  60

Leu Lys Ser Arg Leu Thr Ile Ser Lys Glu Thr Ser Lys Asn Gln Val
65                  70                  75                  80

Phe Leu Lys Ile Ala Asn Val Asp Thr Ala Asp Thr Ala Thr Tyr Tyr
                85                  90                  95

Cys Thr Arg Ile Ala Gly Tyr Tyr Gly Ser Arg Asp Trp Phe Ala Tyr
                100                 105                 110

Trp Gly Gln Gly Thr Thr Val Thr Val Ser Ser
        115                 120

<210> SEQ ID NO 4
<211> LENGTH: 7
<212> TYPE: PRT
<213> ORGANISM: Artificial Sequence
<220> FEATURE:
<223> OTHER INFORMATION: H1609-CDR1

<400> SEQUENCE: 4

Thr Phe Gly Met Gly Val Gly
1               5

<210> SEQ ID NO 5
<211> LENGTH: 16
<212> TYPE: PRT
<213> ORGANISM: Artificial Sequence
<220> FEATURE:
<223> OTHER INFORMATION: H1609-CDR2

<400> SEQUENCE: 5

His Ile Trp Trp Asp Asp Arg Arg Tyr Asn Pro Ala Leu Lys Ser
1               5                   10                  15

<210> SEQ ID NO 6
<211> LENGTH: 13
<212> TYPE: PRT
<213> ORGANISM: Artificial Sequence
<220> FEATURE:
<223> OTHER INFORMATION: H1609-CDR3

<400> SEQUENCE: 6

Ile Ala Gly Tyr Tyr Gly Ser Arg Asp Trp Phe Ala Tyr
1               5                   10

<210> SEQ ID NO 7
<211> LENGTH: 333
<212> TYPE: DNA
<213> ORGANISM: Artificial Sequence
<220> FEATURE:
<223> OTHER INFORMATION: L0293

<400> SEQUENCE: 7
gacattgtgc tgacccagtc tccagcttct ttggctgtgt ctctagggca gagggccacc        60
atctcctgca gagccagcga aagtgttgat aattctggca ttagttttat gcactggtac       120

```
cagcagaaac caggacagcc acccaaactc ctcatctttc gtgcatccga cctagaatct      180
gggatccctg ccaggttcag tggcagtggg tctaggacag acttcaccct caccgttaat      240
cctgtggaga ctgatgatgt tgcaacctat ttctgtcagc aaagtaataa ggatccgtgg      300
acgttcggtg gaggcaccaa gctcgagatc aaa                                   333
```

```
<210> SEQ ID NO 8
<211> LENGTH: 111
<212> TYPE: PRT
<213> ORGANISM: Artificial Sequence
<220> FEATURE:
<223> OTHER INFORMATION: L0293

<400> SEQUENCE: 8
```

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Ser
            20                  25                  30

Gly Ile Ser Phe Met His Trp Tyr Gln Gln Lys Pro Gly Gln Pro Pro
        35                  40                  45

Lys Leu Leu Ile Phe Arg Ala Ser Asp Leu Glu Ser Gly Ile Pro Ala
    50                  55                  60

Arg Phe Ser Gly Ser Gly Ser Arg Thr Asp Phe Thr Leu Thr Val Asn
65                  70                  75                  80

Pro Val Glu Thr Asp Asp Val Ala Thr Tyr Phe Cys Gln Gln Ser Asn
                85                  90                  95

Lys Asp Pro Trp Thr Phe Gly Gly Gly Thr Lys Leu Glu Ile Lys
            100                 105                 110

```
<210> SEQ ID NO 9
<211> LENGTH: 15
<212> TYPE: PRT
<213> ORGANISM: Artificial Sequence
<220> FEATURE:
<223> OTHER INFORMATION: L0293-CDR1

<400> SEQUENCE: 9
```

Arg Ala Ser Glu Ser Val Asp Asn Ser Gly Ile Ser Phe Met His
1               5                   10                  15

```
<210> SEQ ID NO 10
<211> LENGTH: 7
<212> TYPE: PRT
<213> ORGANISM: Artificial Sequence
<220> FEATURE:
<223> OTHER INFORMATION: L0293-CDR2

<400> SEQUENCE: 10
```

Arg Ala Ser Asp Leu Glu Ser
1               5

```
<210> SEQ ID NO 11
<211> LENGTH: 9
<212> TYPE: PRT
<213> ORGANISM: Artificial Sequence
<220> FEATURE:
<223> OTHER INFORMATION: L0293-CDR3

<400> SEQUENCE: 11
```

Gln Gln Ser Asn Lys Asp Pro Trp Thr
1               5

<210> SEQ ID NO 12
<211> LENGTH: 369
<212> TYPE: DNA
<213> ORGANISM: Artificial sequence
<220> FEATURE:
<223> OTHER INFORMATION: H5188

<400> SEQUENCE: 12

```
caggtgcagc tgcaggagag cggcccaggc ctggtgaagc ctagcgagac cctgagcctc    60
acctgcaccg tcagcggctt tagcctgagc acctttggca tgggcgtggg ctggattaga   120
cagcctccag gcaagggcct ggagtggatt gcacacattt ggtgggatga tgataggaga   180
tataacccag ccctgaagag cagagtgacc atcagcaagg acaccagcaa gaaccagttc   240
agcctgaagc tgagcagcgt gaccgctgcc gacaccgccg tgtattactg tgccagaatc   300
gccggctatt atggcagcag agactggttt gcctactggg gccaaggcac cacggtcacc   360
gtctcctca                                                           369
```

<210> SEQ ID NO 13
<211> LENGTH: 123
<212> TYPE: PRT
<213> ORGANISM: Artificial Sequence
<220> FEATURE:
<223> OTHER INFORMATION: H5188/H2177

<400> SEQUENCE: 13

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Thr Phe
            20                  25                  30

Gly Met Gly Val Gly Trp Ile Arg Gln Pro Pro Gly Lys Gly Leu Glu
        35                  40                  45

Trp Ile Ala His Ile Trp Trp Asp Asp Asp Arg Arg Tyr Asn Pro Ala
    50                  55                  60

Leu Lys Ser Arg Val Thr Ile Ser Lys Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ile Ala Gly Tyr Tyr Gly Ser Arg Asp Trp Phe Ala Tyr
            100                 105                 110

Trp Gly Gln Gly Thr Thr Val Thr Val Ser Ser
        115                 120

<210> SEQ ID NO 14
<211> LENGTH: 333
<212> TYPE: DNA
<213> ORGANISM: Artificial Sequence
<220> FEATURE:
<223> OTHER INFORMATION: L5153

<400> SEQUENCE: 14

```
gacatccaga tgacccagtc tccatcctcc ctgtctgcat ctgtgggaga cagagtcacc    60
atcacttgca gagccagcga aagtgttgat aatatgggca ttagtttat gcactggtat   120
cagcagaaac cagggaaagc ccctaagctc ctgatctta gagcatccga cctggaatct   180
ggggtcccat caaggttcag tggcagtgga tctgggacag atttcactct caccatcagc   240
agtctgcaac tgaagatt tgcaacttac tactgtcagc aaagtaataa ggatccctgg   300
accttcggcc aagggaccaa gctcgagatc aaa                                333
```

```
<210> SEQ ID NO 15
<211> LENGTH: 111
<212> TYPE: PRT
<213> ORGANISM: Artificial Sequence
<220> FEATURE:
<223> OTHER INFORMATION: L5153/L5140

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Met
            20                  25                  30

Gly Ile Ser Phe Met His Trp Tyr Gln Gln Lys Pro Gly Lys Ala Pro
        35                  40                  45

Lys Leu Leu Ile Phe Arg Ala Ser Asp Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Lys Asp Pro Trp Thr Phe Gly Gln Gly Thr Lys Leu Glu Ile Lys
            100                 105                 110

<210> SEQ ID NO 16
<211> LENGTH: 15
<212> TYPE: PRT
<213> ORGANISM: Artificial Sequence
<220> FEATURE:
<223> OTHER INFORMATION: L5153-CDR1

<400> SEQUENCE: 16

Arg Ala Ser Glu Ser Val Asp Asn Met Gly Ile Ser Phe Met His
1               5                   10                  15

<210> SEQ ID NO 17
<211> LENGTH: 111
<212> TYPE: PRT
<213> ORGANISM: Artificial Sequence
<220> FEATURE:
<223> OTHER INFORMATION: L5055

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Val Asp Asn Ser
            20                  25                  30

Gly Ile Ser Phe Met His Trp Tyr Gln Gln Lys Pro Gly Lys Ala Pro
        35                  40                  45

Lys Leu Leu Ile Phe Arg Ala Ser Asp Leu Glu Ser Gly Val Pro Ser
    50                  55                  60

Gly Phe Ser Gly Ser Gly Ser Arg Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Lys Asp Pro Trp Thr Phe Gly Gln Gly Thr Lys Leu Glu Ile Lys
            100                 105                 110

<210> SEQ ID NO 18
<211> LENGTH: 333
```

```
<212> TYPE: DNA
<213> ORGANISM: Artificial Sequence
<220> FEATURE:
<223> OTHER INFORMATION: L5055

<400> SEQUENCE: 18
gacatccaga tgacccagtc tccatcctcc ctgtctgcat ctgtgggaga cagagtcacc    60
atcacttgca gagccagcga aagtgttgat aattctggca ttagttttat gcactggtat   120
cagcagaaac cagggaaagc ccctaagctc ctgatcttta gagcatccga cctggaatct   180
ggggtcccat cagggttcag tggcagtgga tctaggacag atttcactct caccatcagc   240
agtctgcaac ctgaagattt tgcaacttac tactgtcagc aaagtaataa ggatccctgg   300
accttcggcc aagggaccaa gctcgagatc aaa                                 333

<210> SEQ ID NO 19
<211> LENGTH: 109
<212> TYPE: PRT
<213> ORGANISM: Homo sapiens

<400> SEQUENCE: 19

Met Lys Phe Ile Ser Thr Ser Leu Leu Leu Met Leu Leu Val Ser Ser
1               5                   10                  15

Leu Ser Pro Val Gln Gly Val Leu Glu Val Tyr Tyr Thr Ser Leu Arg
                20                  25                  30

Cys Arg Cys Val Gln Glu Ser Ser Val Phe Ile Pro Arg Arg Phe Ile
            35                  40                  45

Asp Arg Ile Gln Ile Leu Pro Arg Gly Asn Gly Cys Pro Arg Lys Glu
        50                  55                  60

Ile Ile Val Trp Lys Lys Asn Lys Ser Ile Val Cys Val Asp Pro Gln
65                  70                  75                  80

Ala Glu Trp Ile Gln Arg Met Met Glu Val Leu Arg Lys Arg Ser Ser
                85                  90                  95

Ser Thr Leu Pro Val Pro Val Phe Lys Arg Lys Ile Pro
            100                 105

<210> SEQ ID NO 20
<211> LENGTH: 1219
<212> TYPE: DNA
<213> ORGANISM: Homo sapiens

<400> SEQUENCE: 20
gagaagatgt ttgaaaaaac tgactctgct aatgagcctg gactcagagc tcaagtctga    60
actctacctc cagacagaat gaagttcatc tcgacatctc tgcttctcat gctgctggtc   120
agcagcctct ctccagtcca aggtgttctg gaggtctatt acacaagctt gaggtgtaga   180
tgtgtccaag agagctcagt ctttatccct agacgcttca ttgatcgaat tcaaatcttg   240
ccccgtggga tggttgtcc aagaaaagaa atcatagtct ggaagaagaa caagtcaatt   300
gtgtgtgtgg accctcaagc tgaatggata caaagaatga tggaagtatt gagaaaaaga   360
agttcttcaa ctctaccagt tccagtgttt aagagaaaga ttccctgatg ctgatatttc   420
cactaagaac acctgcattc ttcccttatc cctgctctgg attttagttt tgtgcttagt   480
taaatctttt ccaggaaaaa gaacttcccc atacaaataa gcatgagact atgtaaaaat   540
aaccttgcag aagctgatgg ggcaaactca agcttcttca ctcacagcac cctatataca   600
cttggagttt gcattcttat tcatcaggga ggaaagtttc tttgaaaata gttattcagt   660
tataagtaat acaggattat tttgattata tacttgttgt ttaatgttta aaatttctta   720
```

```
gaaaacaatg gaatgagaat ttaagcctca aatttgaaca tgtggcttga attaagaaga        780
aaattatggc atatattaaa agcaggcttc tatgaaagac tcaaaaagct gcctgggagg        840
cagatggaac ttgagcctgt caagaggcaa aggaatccat gtagtagata tcctctgctt        900
aaaaactcac tacggaggag aattaagtcc tactttaaa  gaatttcttt ataaaattta        960
ctgtctaaga ttaatagcat tcgaagatcc ccagacttca tagaatactc agggaaagca       1020 tttaagggt  gatgtacaca tgtatccttt cacacatttg ccttgacaaa cttctttcac       1080
tcacatcttt ttcactgact ttttttgtgg ggggcggggc cggggggact ctggtatcta       1140 attcttaat  gattcctata aatctaatga cattcaataa agttgagcaa acattttact       1200
taaaaaaaaa aaaaaaaaa                                                     1219
```

<210> SEQ ID NO 21
<211> LENGTH: 109
<212> TYPE: PRT
<213> ORGANISM: Mus musculus

<400> SEQUENCE: 21

```
Met Arg Leu Ser Thr Ala Thr Leu Leu Leu Leu Ala Ser Cys Leu
1               5                   10                  15

Ser Pro Gly His Gly Ile Leu Glu Ala His Tyr Thr Asn Leu Lys Cys
            20                  25                  30

Arg Cys Ser Gly Val Ile Ser Thr Val Val Gly Leu Asn Ile Ile Asp
        35                  40                  45

Arg Ile Gln Val Thr Pro Pro Gly Asn Gly Cys Pro Lys Thr Glu Val
    50                  55                  60

Val Ile Trp Thr Lys Met Lys Lys Val Ile Cys Val Asn Pro Arg Ala
65                  70                  75                  80

Lys Trp Leu Gln Arg Leu Leu Arg His Val Gln Ser Lys Ser Leu Ser
                85                  90                  95

Ser Thr Pro Gln Ala Pro Val Ser Lys Arg Arg Ala Ala
            100                 105
```

<210> SEQ ID NO 22
<211> LENGTH: 1162
<212> TYPE: DNA
<213> ORGANISM: Mus musculus

<400> SEQUENCE: 22

```
gagctaaagg ttgaactcca cctccaggca gaatgaggct cagcacagca acgctgcttc         60
tcctcctggc cagctgcctc tctccaggcc acggtattct ggaagcccat tacacaaact        120
taaaatgtag gtgttctgga gtgatttcaa ctgttgtcgg tctaaacatc atagatcgga        180
ttcaagttac gcccctggg  aatggctgcc ccaaaactga agttgtgatc tggaccaaga        240
tgaagaaagt tatatgtgtg aatcctcgtg ccaaatggtt acaagagatt attaagacatg       300 tccaaagcaa aagtctgtct tcaactcccc aagctccagt gagtaagaga agagctgcct        360
gaagccacta tcatctcaaa agacacacct gcaccttttt ttttatccct gctctgaatt        420
ttagatatgt tcttagttaa agaatttcca agaaaataac tcccctctac aaacaaacat        480
gactgtaggt aaaacaaagc aaaaacaaac aagcaaacaa acaaactaaa aaaaacccaa        540
tcctgcagga gctgagaggg aatgctcaag ctccgttgca tacccaaccc acatccttgt        600
tccttaagaa aggctatttg agaacaggca tttagtgaca acccacttca gatgcatgtg        660
gtaatagatc tgttgtttaa tgttaaacta tcctagattg tcgaggaatg aaaaacctac        720
```

```
atgtcaaatg tgaacttgta gctcgtacta acaagaggtt tgcgagatgg acttcagtta    780
ttttgcaccc ttgtaaaacg caggcttcca aaatagtctc cagaaggttc ctgggaagct    840
ggtgcaatgc catcatgagg tggtgcaaag caggtctcct ttagagaaaa gcttcctggg    900
ggaaacagtc ctactttgaa aggttgcttg tataagattt attgtcttgc attaaaacca    960
gtaacaattg aaagatcctc agcttaaagg tccaggctct tcagcagtat acaaatatat   1020
tcctttgcac tgtgaccctg atgatctatt tttattattc atatctttca cacagacaaa   1080
ataccagcct cttgtatcag attctttaat gtttcctatt catctggtgt cattcaataa   1140
atgtaatcaa atgttttgct ta                                            1162

<210> SEQ ID NO 23
<211> LENGTH: 82
<212> TYPE: PRT
<213> ORGANISM: Macaca fascicularis

<400> SEQUENCE: 23

Val Leu Glu Val Tyr Tyr Thr His Leu Arg Cys Arg Cys Val Gln Glu
1               5                   10                  15

Ser Ser Val Phe Ile Pro Arg Arg Phe Ile Asp Arg Ile Gln Ile Ser
            20                  25                  30

Pro Arg Gly Asn Gly Cys Pro Arg Lys Glu Ile Ile Val Trp Lys Lys
        35                  40                  45

Asn Lys Ser Val Val Cys Val Asp Pro Gln Ala Glu Trp Ile Gln Arg
    50                  55                  60

Ile Met Glu Met Leu Arg Lys Lys Ser Ser Ser Thr Pro Pro Val Pro
65                  70                  75                  80

Val Phe

<210> SEQ ID NO 24
<211> LENGTH: 21
<212> TYPE: DNA
<213> ORGANISM: Artificial Sequence
<220> FEATURE:
<223> OTHER INFORMATION: 16s Forward primer

<400> SEQUENCE: 24
ttgggaggct ttgtctttcc a                                               21

<210> SEQ ID NO 25
<211> LENGTH: 21
<212> TYPE: DNA
<213> ORGANISM: Artificial Sequence
<220> FEATURE:
<223> OTHER INFORMATION: 16s Reverse primer

<400> SEQUENCE: 25
gattagctct gcctcgcggc t                                               21
```